US012054479B1

(12) United States Patent
Paliwal et al.

(10) Patent No.: US 12,054,479 B1
(45) Date of Patent: Aug. 6, 2024

(54) MULTICYCLIC COMPOUNDS

(71) Applicant: SLAP Pharmaceuticals LLC, Brighton, MA (US)

(72) Inventors: Sunil Paliwal, Monroe Township, NJ (US); Ahmed Abdi Samatar, West Windsor, NJ (US); Lawrence Saunders Cripe, Boston, MA (US)

(73) Assignee: SLAP Pharmaceuticals LLC, Brighton, MA (US)

( * ) Notice: Subject to any disclaimer, the term of this patent is extended or adjusted under 35 U.S.C. 154(b) by 0 days.

(21) Appl. No.: 18/596,024

(22) Filed: Mar. 5, 2024

Related U.S. Application Data

(63) Continuation of application No. PCT/US2023/064231, filed on Mar. 13, 2023.

(60) Provisional application No. 63/363,144, filed on Apr. 18, 2022, provisional application No. 63/269,329, filed on Mar. 14, 2022.

(51) Int. Cl.
*C07D 413/12* (2006.01)
*A61K 31/538* (2006.01)

(52) U.S. Cl.
CPC .......... *C07D 413/12* (2013.01); *A61K 31/538* (2013.01)

(58) Field of Classification Search
CPC .............................. C07D 413/12; A61K 31/538
USPC ....................................................... 514/230.5
See application file for complete search history.

(56) References Cited

U.S. PATENT DOCUMENTS

| | | | |
|---|---|---|---|
| 5,919,784 | A | 7/1999 | Lesieur et al. |
| 6,545,000 | B1 | 4/2003 | Shimada et al. |
| 7,582,634 | B2 | 9/2009 | Pelletier et al. |
| 8,669,249 | B2 | 3/2014 | Brown et al. |
| 2006/0019969 | A1 | 1/2006 | Cabrera |
| 2006/0205719 | A1 | 9/2006 | Surivet et al. |
| 2006/0287309 | A1 | 12/2006 | Clark et al. |
| 2006/0287310 | A1 | 12/2006 | Clark et al. |
| 2010/0063040 | A1 | 3/2010 | Kugimiya |
| 2010/0216783 | A1 | 8/2010 | Bhat et al. |
| 2010/0324030 | A1 | 12/2010 | Dale et al. |
| 2012/0108566 | A1 | 5/2012 | Bauer et al. |
| 2014/0128603 | A1 | 5/2014 | Chaudhari et al. |
| 2015/0148342 | A1 | 5/2015 | Yue et al. |
| 2015/0148372 | A1 | 5/2015 | Yue et al. |
| 2015/0148375 | A1 | 5/2015 | Yue et al. |
| 2016/0318933 | A1 | 11/2016 | Yoshinaga et al. |
| 2017/0294582 | A1 | 10/2017 | Martynova et al. |
| 2019/0142838 | A1 | 5/2019 | Bhat et al. |
| 2020/0331868 | A1 | 10/2020 | Zhang et al. |

FOREIGN PATENT DOCUMENTS

| | | |
|---|---|---|
| AU | 2003261756 A1 | 3/2004 |
| CN | 108250058 A | 7/2018 |
| CN | 113429410 A | 9/2021 |
| CN | 113999232 A | 2/2022 |
| CN | 114634479 A | 6/2022 |
| CN | 115232129 A | 10/2022 |
| CN | 115232154 A | 10/2022 |
| CN | 116496271 A | 7/2023 |
| CN | 116693501 A | 9/2023 |
| CN | 116891456 A | 10/2023 |
| DE | 10316081 A1 | 10/2004 |
| EP | 841330 A1 | 5/1998 |
| EP | 1086104 A1 | 3/2001 |
| EP | 1201268 A2 | 5/2002 |
| EP | 1213031 A2 | 6/2002 |
| EP | 1707202 A1 | 10/2006 |
| EP | 1707206 A1 | 10/2006 |
| EP | 2163245 A1 | 3/2010 |
| EP | 2511273 A1 | 10/2012 |
| IN | 2005DE03142 A | 3/2010 |
| JP | 55027158 A | 2/1980 |
| JP | 2016204374 A | 12/2016 |
| WO | WO 97/23216 A1 | 7/1997 |
| WO | WO 97/45419 A1 | 12/1997 |
| WO | WO 1999/062907 A1 | 12/1999 |
| WO | WO 2000/017201 A1 | 3/2000 |
| WO | WO 2000/021926 A2 | 4/2000 |
| WO | WO 2001/077100 A2 | 1/2001 |
| WO | WO 2001/057003 A1 | 8/2001 |
| WO | WO 2002/020020 A1 | 3/2002 |
| WO | WO 2003/076438 A1 | 9/2003 |
| WO | WO 2003/084948 A1 | 10/2003 |
| WO | WO 2004/022535 A1 | 3/2004 |
| WO | WO 2004/100954 A1 | 11/2004 |
| WO | WO 2004/100955 A1 | 11/2004 |
| WO | WO 2004/100956 A1 | 11/2004 |

(Continued)

OTHER PUBLICATIONS

Belliotti et al., "A Series of 6- and 7-Piperazinyl- and -Piperidinylmethylbenzoxazinones with Dopamine D4 Antagonist Activity: Discovery of a Potential Atypical Antipsychotic Agent" Journal of Medicinal Chemistry (1999) 42(25):5181-5187.

Bi et al., "Mixed-mechanism ionization to enhance sensitivity in atmospheric pressure ionization LC/MS" Journal of Pharmaceutical and Biomedical Analysis (2000) 22(5):861-867.

(Continued)

*Primary Examiner* — Kahsay Habte

(74) *Attorney, Agent, or Firm* — Knobbe Martens Olson & Bear LLP

(57) ABSTRACT

Provided herein are compounds of Formula (I), or pharmaceutically acceptable salts thereof, pharmaceutical compositions that include a compound described herein (including pharmaceutically acceptable salts of a compound described herein) and methods of synthesizing the same. Also provided herein are methods of treating diseases and/or conditions with a compound of Formula (I), or a pharmaceutically acceptable salt thereof.

4 Claims, No Drawings

(56) References Cited

FOREIGN PATENT DOCUMENTS

| | | |
|---|---|---|
| WO | WO 2004/100957 A1 | 11/2004 |
| WO | WO 2005/019215 A1 | 3/2005 |
| WO | WO 2005/037803 A1 | 4/2005 |
| WO | WO 2005/061457 A1 | 7/2005 |
| WO | WO 2005/102342 A1 | 11/2005 |
| WO | WO 2006/005741 A2 | 1/2006 |
| WO | WO 2006/012396 A1 | 2/2006 |
| WO | WO 2006/014580 A1 | 2/2006 |
| WO | WO 2006/015259 A1 | 2/2006 |
| WO | WO 2007/037187 A1 | 4/2007 |
| WO | WO 2007/042325 A1 | 4/2007 |
| WO | WO 2007/093624 A1 | 8/2007 |
| WO | WO 2008/068266 A1 | 6/2008 |
| WO | WO 2008/068267 A1 | 6/2008 |
| WO | WO 2008/068269 A1 | 6/2008 |
| WO | WO 2008/068270 A1 | 6/2008 |
| WO | WO 2008/068272 A2 | 6/2008 |
| WO | WO 2008/107478 A1 | 9/2008 |
| WO | WO 2009/006437 A1 | 1/2009 |
| WO | WO 2009/053373 A1 | 4/2009 |
| WO | WO 2009/053715 A1 | 4/2009 |
| WO | WO 2009/076404 A1 | 6/2009 |
| WO | WO 2009/076512 A1 | 6/2009 |
| WO | WO 2010/009195 A1 | 1/2010 |
| WO | WO 2010/056038 A2 | 5/2010 |
| WO | WO 2010/080537 A1 | 7/2010 |
| WO | WO 2010/111626 A2 | 9/2010 |
| WO | WO 2010/129843 A1 | 11/2010 |
| WO | WO 2010/151711 A1 | 12/2010 |
| WO | WO 2011/073378 A1 | 6/2011 |
| WO | WO 2011/091840 A2 | 8/2011 |
| WO | WO 2012/020738 A1 | 2/2012 |
| WO | WO 2012/033144 A1 | 3/2012 |
| WO | WO 2012/140243 A1 | 10/2012 |
| WO | WO 2012/149236 A1 | 11/2012 |
| WO | WO 2013/024895 A1 | 2/2013 |
| WO | WO 2013/050438 A1 | 4/2013 |
| WO | WO 2013/068785 A1 | 5/2013 |
| WO | WO 2013/160431 A1 | 10/2013 |
| WO | WO 2013/160435 A1 | 10/2013 |
| WO | WO 2013/192423 A2 | 12/2013 |
| WO | WO 2004/046124 A1 | 6/2014 |
| WO | WO 2015/048633 A2 | 4/2015 |
| WO | WO 2015/048641 A2 | 4/2015 |
| WO | WO 2015/060348 A1 | 4/2015 |
| WO | WO 2015/076353 A1 | 5/2015 |
| WO | WO 2015/131856 A1 | 9/2015 |
| WO | WO 2015/157451 A1 | 10/2015 |
| WO | WO 2015/161142 A1 | 10/2015 |
| WO | WO 2016/008011 A1 | 1/2016 |
| WO | WO 2016/034262 A1 | 3/2016 |
| WO | WO 2016/115039 A1 | 7/2016 |
| WO | WO 2016/115144 A1 | 7/2016 |
| WO | WO 2016/115150 A1 | 7/2016 |
| WO | WO 2016/200101 A2 | 12/2016 |
| WO | WO 2017/029602 A2 | 2/2017 |
| WO | WO 2017/070796 A1 | 5/2017 |
| WO | WO 2017/212010 A1 | 12/2017 |
| WO | WO 2017/214367 A1 | 12/2017 |
| WO | WO 2018014802 A1 | 1/2018 |
| WO | WO 2018/053588 A1 | 3/2018 |
| WO | WO 2018/099952 A1 | 6/2018 |
| WO | WO 2018/106646 A1 | 6/2018 |
| WO | WO 2018/175746 A1 | 9/2018 |
| WO | WO 2019/105915 A1 | 6/2019 |
| WO | WO 2019/115660 A1 | 6/2019 |
| WO | WO 2019/133901 A1 | 7/2019 |
| WO | WO 2019/135259 A1 | 7/2019 |
| WO | WO 2019/141229 A1 | 7/2019 |
| WO | WO 2019/243526 A1 | 12/2019 |
| WO | WO 2019/243527 A1 | 12/2019 |
| WO | WO 2020/006018 A1 | 1/2020 |
| WO | WO 2020/039027 A1 | 2/2020 |
| WO | WO 2020/069027 A1 | 4/2020 |
| WO | WO 2020/205501 A1 | 10/2020 |
| WO | WO 2021/013735 A1 | 1/2021 |
| WO | WO 2021/161230 A1 | 8/2021 |
| WO | WO 2021/208963 A1 | 10/2021 |
| WO | WO 2021/231933 A1 | 11/2021 |
| WO | WO 2021/260092 A1 | 12/2021 |
| WO | WO 2022/028507 A1 | 2/2022 |
| WO | WO 2022/2247816 | 3/2022 |
| WO | WO 2022/074617 A1 | 4/2022 |
| WO | WO 2022/081976 A1 | 4/2022 |
| WO | WO 2022/086986 A1 | 4/2022 |
| WO | WO 2002/058695 A1 | 8/2022 |
| WO | WO 2022/199662 A1 | 9/2022 |
| WO | WO 2022/222921 A1 | 10/2022 |
| WO | WO 2022/222964 A1 | 10/2022 |
| WO | WO 2022/222965 A1 | 10/2022 |
| WO | WO 2022/222966 A1 | 10/2022 |
| WO | WO 2022/222995 A1 | 10/2022 |
| WO | WO 2022/223025 A1 | 10/2022 |
| WO | WO 2022/225934 A1 | 10/2022 |
| WO | WO 2022/228387 A1 | 11/2022 |
| WO | WO 2022/235585 A1 | 11/2022 |
| WO | WO 2022/261777 A1 | 12/2022 |
| WO | WO 2023/011608 A1 | 2/2023 |
| WO | WO 2023/025307 A1 | 3/2023 |
| WO | WO 2023/036285 A1 | 3/2023 |
| WO | WO 2023/046034 A1 | 3/2023 |
| WO | WO 2023/046149 A1 | 3/2023 |
| WO | WO 2023/046158 A1 | 3/2023 |
| WO | WO 2023/051716 A1 | 4/2023 |
| WO | WO 2023/051807 A1 | 4/2023 |
| WO | WO 2023/051812 A1 | 4/2023 |
| WO | WO 2023/056039 A1 | 4/2023 |
| WO | WO 2023/061406 A1 | 4/2023 |
| WO | WO 2023/066363 A1 | 4/2023 |
| WO | WO 2023/088408 A1 | 5/2023 |
| WO | WO 2023/089527 A1 | 5/2023 |
| WO | WO 2023/109521 A1 | 6/2023 |
| WO | WO 2023/118085 A1 | 6/2023 |
| WO | WO 2023/122140 A1 | 6/2023 |
| WO | WO 2023/133413 A1 | 7/2023 |
| WO | WO 2023/134647 A1 | 7/2023 |
| WO | WO 2023/138541 A1 | 7/2023 |
| WO | WO 2023/141290 A1 | 7/2023 |
| WO | WO 2023/146957 A1 | 8/2023 |
| WO | WO 2023/146960 A1 | 8/2023 |
| WO | WO 2023/169226 A1 | 9/2023 |
| WO | WO 2023/178035 A1 | 9/2023 |
| WO | WO 2023/201338 A1 | 10/2023 |
| WO | WO 2023/207283 A1 | 11/2023 |
| WO | WO 2023/207284 A1 | 11/2023 |
| WO | WO 2023/212219 A1 | 11/2023 |
| WO | WO 2023/217045 A1 | 11/2023 |

OTHER PUBLICATIONS

Carato et al., "Synthesis and binding studies on a new series of arylpiperazino benzazol-2-one and benzoxazin-3-one derivatives as selective D4 ligands" Drug Design and Discovery (2000) 17(2):173-181.
CAS Reg. No. 2818705-15-4, Entered Sep. 5, 2022.
CAS Reg. No. 2818665-36-8, Entered Sep. 5, 2022.
CAS Reg. No. 2818360-53-9, Entered Sep. 5, 2022.
CAS Reg. No. 2816389-77-0, Entered Sep. 1, 2022.
CAS Reg. No. 2816200-71-0, Entered Sep. 1, 2022.
CAS Reg. No. 2814572-77-3, Entered Aug. 29, 2022.
CAS Reg. No. 2812952-93-3, Entered Aug. 26, 2022.
CAS Reg. No. 2812907-36-9, Entered Aug. 26, 2022.
CAS Reg. No. 2811378-58-0, Entered Aug. 24, 2022.
CAS Reg. No. 2811257-14-2, Entered Aug. 24, 2022.
CAS Reg. No. 2811061-11-5, Entered Aug. 24, 2022.
CAS Reg. No. 2808639-27-0, Entered Aug. 21, 2022.
CAS Reg. No. 2808377-20-8, Entered Aug. 19, 2022.
CAS Reg. No. 2807976-15-2, Entered Aug. 19, 2022.
CAS Reg. No. 2806880-21-5, Entered Aug. 18, 2022.
CAS Reg. No. 2805064-17-7, Entered Aug. 15, 2022.
CAS Reg. No. 2805060-07-3, Entered Aug. 15, 2022.

(56) References Cited

OTHER PUBLICATIONS

CAS Reg. No. 2804605-33-0, Entered Aug. 15, 2022.
CAS Reg. No. 2802571-39-5, Entered Aug. 4, 2022.
CAS Reg. No. 2802039-84-3, Entered Aug. 3, 2022.
CAS Reg. No. 2801340-76-9, Entered Aug. 2, 2022.
CAS Reg. No. 2800171-08-6, Entered Jul. 31, 2022.
CAS Reg. No. 2800023-56-5, Entered Jul. 31, 2022.
CAS Reg. No. 2799966-10-0, Entered Jul. 31, 2022.
CAS Reg. No. 2799133-15-4, Entered Jul. 29, 2022.
CAS Reg. No. 2798500-61-3, Entered Jul. 28, 2022.
CAS Reg. No. 2798395-05-6, Entered Jul. 28, 2022.
CAS Reg. No. 2797860-14-9, Entered Jul. 27, 2022.
CAS Reg. No. 2471549-95-6, Entered Sep. 3, 2020.
CAS Reg. No. 2467831-57-6, Entered Aug. 28, 2020.
CAS Reg. No. 2466477-04-1, Entered Aug. 28, 2020.
CAS Reg. No. 2466426-08-2, Entered Aug. 28, 2020.
CAS Reg. No. 2465058-60-8, Entered Aug. 27, 2020.
CAS Reg. No. 2462993-03-7, Entered Aug. 27, 2020.
CAS Reg. No. 2461336-88-7, Entered Aug. 26, 2020.
CAS Reg. No. 2454148-37-7, Entered Aug. 6, 2020.
CAS Reg. No. 2451441-63-5, Entered Jul. 30, 2020.
CAS Reg. No. 2451259-71-3, Entered Jul. 29, 2020.
CAS Reg. No. 2450726-00-6, Entered Jul. 28, 2020.
CAS Reg. No. 2432543-41-2, Entered Jun. 23, 2020.
CAS Reg. No. 2427659-32-1, Entered Jun. 18, 2020.
CAS Reg. No. 2424935-49-7, Entered Jun. 15, 2020.
CAS Reg. No. 2423550-50-7, Entered Jun. 12, 2020.
CAS Reg. No. 2423020-28-2, Entered Jun. 11, 2020.
CAS Reg. No. 2422710-04-9, Entered Jun. 11, 2020.
CAS Reg. No. 2422406-61-7, Entered Jun. 11, 2020.
CAS Reg. No. 2421553-76-4, Entered Jun. 10, 2020.
CAS Reg. No. 2391836-05-6, Entered De. 16, 2019.
CAS Reg. No. 2373551-05-2, Entered Sep. 4, 2019.
CAS Reg. No. 2372934-15-9, Entered Sep. 3, 2019.
CAS Reg. No. 2372798-80-4, Entered Sep. 3, 2019.
CAS Reg. No. 2372733-29-2, Entered Sep. 3, 2019.
CAS Reg. No. 2371808-72-7, Entered Sep. 2, 2019.
CAS Reg. No. 2371324-85-3, Entered Sep. 1, 2019.
CAS Reg. No. 2370875-02-6, Entered Aug. 30, 2019.
CAS Reg. No. 2370826-58-5, Entered Aug. 30, 2019.
CAS Reg. No. 2324260-52-6, Entered Jun. 5, 2019.
CAS Reg. No. 2248994-35-4, Entered Nov. 18, 2018.
CAS Reg. No. 2224518-69-6, Entered May 21, 2018.
CAS Reg. No. 2224183-87-1, Entered May 20, 2018.
CAS Reg. No. 2224159-31-1, Entered May 20, 2018.
CAS Reg. No. 2224155-00-2, Entered May 20, 2018.
CAS Reg. No. 2224148-48-3, Entered May 20, 2018.
CAS Reg. No. 2223302-69-8, Entered May 18, 2018.
CAS Reg. No. 2223302-05-2, Entered May 18, 2018.
CAS Reg. No. 2223280-83-7, Entered May 18, 2018.
CAS Reg. No. 2223250-68-6, Entered May 18, 2018.
CAS Reg. No. 2192977-79-8, Entered Mar. 16, 2018.
CAS Reg. No. 1026052-88-9, Entered Jun. 6, 2008.
Egnash et al. "Comparison of heterogeneous and homogeneous radioactivity flow detectors for simultaneous profiling and LC-MS/MS characterization of metabolites" Journal of Pharmaceutical and Biomedical Analysis (2002) 27(1-2):271-284.
Gangloff et al., "Discovery of novel benzo[b][1,4]oxazin-3(4H)-ones as poly(ADP-ribose)polymerase inhibitors" Bioorganic & Medicinal Chemistry Letters (2013) 23(16):4501-4505.
Kim et al., "Classification of dopamine antagonists using functional feature hypothesis and topological descriptors" Bioorganic & Medicinal Chemistry (2006) 14(5):1454-1461.
PubChem SID 378965184, modified Jun. 3, 2019, available Jan. 24, 2019.
Xia et al., "The synthesis of 4,7-disubstituted-2H-benzo[b][1,4]-oxazin-3(4H)-ones using Smiles rearrangement and their in vitro evaluation as platelet aggregation inhibitors" Bioorganic & Medicinal Chemistry Letters (2014) 24(6):1479-1483.
Zuo et al., "Systematic inhibitor selectivity between PARP1 and PARP2 enzymes: Molecular implications for ovarian cancer personalized therapy" Journal of Molecular Recognition (2021) 34(7):e2891.
International Search Report and Written Opinion mailed Aug. 9, 2023 for PCT Application No. PCT/US2023/064231, filed Mar. 13, 2023.
229 Answers as of Jun. 28, 2022.

MULTICYCLIC COMPOUNDS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including PCT Application No. PCT/US2023/064231, filed Mar. 13, 2023, and U.S. Provisional Application Nos. 63/269,329, filed Mar. 14, 2022 and 63/363,144, filed Apr. 18, 2022, each of which is incorporated by reference in their entireties. This application is a continuation of PCT Application No. PCT/US2023/064231, filed Mar. 13, 2023, which claims priority to U.S. Provisional Application Nos. 63/269,329, filed Mar. 14, 2022 and 63/363,144, filed Apr. 18, 2022.

BACKGROUND

Field

The present application relates to the fields of chemistry, biochemistry and medicine. Disclosed herein are compounds of Formula (I), or pharmaceutically acceptable salt thereof, pharmaceutical compositions that include a compound described herein (including pharmaceutically acceptable salts of a compound described herein) and methods of synthesizing the same. Also disclosed herein are methods of treating diseases and/or conditions with a compound of Formula (I), or a pharmaceutically acceptable salt thereof.

Description

According to the National Cancer Institute, an estimated 1,806,590 new cases of cancer will be diagnosed in the United States and 606,520 people will die from the disease in 2020. The most common cancers are breast cancer, lung and bronchus cancer, prostate cancer, colon and rectum cancer, melanoma of the skin, bladder cancer, non-Hodgkin lymphoma, kidney and renal pelvis cancer, endometrial cancer, leukemia, pancreatic cancer, thyroid cancer, and liver cancer.

SUMMARY

Some embodiments disclosed herein relate to a compound of Formula (I), or a pharmaceutically acceptable salt thereof.

Some embodiments disclosed herein relate to a pharmaceutical composition that can contain an effective amount of a compound of Formula (I), or a pharmaceutically acceptable salt thereof.

Some embodiments described herein relate to a method of treating a cancer described herein that can include administering an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for treating a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for treating a cancer described herein.

Some embodiments described herein relate to a method for inhibiting growth of a malignant growth or a tumor that can include contacting the growth or the tumor with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof), wherein the malignant growth or tumor is due to a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for inhibiting growth of a malignant growth or a tumor, wherein the malignant growth or tumor is due to a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for inhibiting growth of a malignant growth or a tumor, wherein the malignant growth or tumor is due to a cancer described herein.

Some embodiments described herein relate to a method for treating a cancer described herein that can include contacting a malignant growth or a tumor with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for treating a cancer described herein that can include contacting a malignant growth or a tumor, wherein the malignant growth or tumor is due to a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for treating a cancer described herein that can include contacting a malignant growth or a tumor, wherein the malignant growth or tumor is due to a cancer described herein.

Some embodiments described herein relate to a method for inhibiting the activity of PARP1 in a cell that can include providing an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a cancer cell from a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for inhibiting the activity of PARP1. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for inhibiting the activity of PARP1.

Some embodiments described herein relate to a method for treating a cancer described herein that can include inhibiting the activity of PARP1 using an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof). Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for treating a cancer described herein by inhibiting the activity of PARP1. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for treating a cancer described herein by inhibiting the activity of PARP1.

These are other embodiments are described in greater detail below.

DETAILED DESCRIPTION

Accumulation of DNA damage without repair over a period can lead to the development of cancer. Poly (ADP-ribose) polymerases (PARP1/2) are enzymes that sense DNA damage and add branched PAR chains to facilitate DNA repair. PARP inhibitors are a class of small molecules that inhibit both PARP1 and PARP2, and have been approved as cancer drugs for tumors with BRCA1/2 mutations.

Although PARP1 is considered the major target of PARP inhibitors, the currently approved PARP inhibitors also inhibit PARP2 and PARP3. Beyond its DNA repair role, PARP1 has additional biological roles which include the regulation of transcription of several genes implicated in several cancers. Inhibition of PARP1 with a PARP1 selective small molecule could potentially overcome some of the major toxicities observed with the current PARP1/2 inhibitors and bring meaningful benefit to cancer patients.

Poly (ADP-ribose) polymerases (PARP) 1/2 Poly inhibitors selectively kill cancer cells that have defect in the homologous recombination repair pathway and have been approved for use in ovarian cancer, metastatic breast cancer and prostate cancer. Although clinical studies have shown that the PARP1/2 inhibitors have antitumor activity in tumors with BRCA1/2 mutations, cancer patients with alterations in DNA damage repair pathway may be able to benefit from PARP inhibitors. Mutations in DNA damage repair pathway is observed in a broad range of tumor types suggesting that the PARP1/2 inhibitors could potentially have antitumor activity in several cancer types.

Although PARP inhibitors have demonstrated antitumor activity, the adverse events seen in patients treated with the PARP1/2 inhibitors have necessitated dose reductions and discontinuation of the PARP1/2 inhibitors. The adverse events of the PARP1/2 inhibitors are thought to arise from inhibition of PARP2, hence small molecules that are potent and selective for PARP1 could retain the antitumor activity and potentially minimize the adverse events observed with the current PARP1/2 inhibitors.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) (such as 1, 2 or 3) individually and independently selected from deuterium, alkyl, alkenyl, alkynyl, cycloalkyl, cycloalkenyl, aryl, heteroaryl, heterocyclyl, aryl(alkyl), heteroaryl(alkyl), heterocyclyl(alkyl), hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, C-amido(alkyl), isocyanato, thiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amine and a di-substituted amine.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused- or spiro-fashion. Cycloalkyl groups can contain 3 to 10 atoms in the ring(s). 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused- or spiro-fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "cycloalkyl(alkyl)" refer to a cycloalkyl group connected, as a substituent, via a lower alkylene group. The lower alkylene and aryl group of a cycloalkyl (alkyl) may be substituted or unsubstituted. Examples include but are not limited to cyclopropyl-$CH_2$—, cyclobutyl-CH$_2$—, cyclopentyl-CH$_2$—, cyclohexyl-CH$_2$—, cyclopropyl-CH$_2$CH$_2$—, cyclobutyl-CH$_2$CH$_2$—, cyclopentyl-CH$_2$CH$_2$—, cyclohexyl-CH$_2$CH$_2$—, cyclopropyl-CH$_2$CH$_2$CH$_2$—, cyclobutyl-CH$_2$CH$_2$CH$_2$—, cyclopentyl-CH$_2$CH$_2$CH$_2$—, cyclohexyl-CH$_2$CH$_2$CH$_2$—, cyclopropyl-CH$_2$CH$_2$CH$_2$CH$_2$—, cyclobutyl-CH$_2$CH$_2$CH$_2$CH$_2$—, cyclopentyl-CH$_2$CH$_2$CH$_2$CH$_2$— and cyclohexyl-CH$_2$CH$_2$CH$_2$CH$_2$—.

As used herein, "aryl(alkyl)" refers to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

A "heterocyclyl(alkyl)" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—) and butylene (—CH$_2$CH$_2$CH$_2$CH$_2$—). A lower alkylene group can be substituted by replacing one or more hydrogen of the lower alkylene group with a substituent(s) listed under the definition of "substituted." Further, when a lower alkylene group is substituted, the lower alkylene can be substituted by replacing both hydrogens on the same carbon with a cycloalkyl group (e.g.,

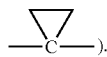

).

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzyloxy. In some instances, an alkoxy can be —OR, wherein R is an unsubstituted C$_{1-4}$ alkyl. An alkoxy may be substituted or unsubstituted.

As used herein, "acyl" refers to a hydrogen, an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) connected, as substituents, via a carbonyl group. Examples include formyl, acetyl, propanoyl, benzoyl and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group and O-monocyclic cycloalkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy, 2-fluoroisobutoxy, chloro-substituted cyclopropyl, fluoro-substituted cyclopropyl, chloro-substituted cyclobutyl and fluoro-substituted cyclobutyl. In some instances, a haloalkoxy can be —OR, wherein R is a C$_{1-4}$ alkyl substituted by 1, 2 or 3 halogens. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$_A$)—" group wherein each X is a halogen, and R$_A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a —C(=O)— group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(=S)—N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(=S)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

A "mono-substituted amine" refers to a "—NHR$_A$" in which R$_A$ can be independently alkyl, alkenyl, alkynyl, cycloalkyl, cycloalkenyl, aryl, heteroaryl, heterocyclyl, aryl(alkyl), heteroaryl(alkyl) or heterocyclyl(alkyl). A mono-substituted amine may be substituted or unsubstituted. In some instances, a mono-substituted amine can be —NHR$_A$, wherein R$_A$ can be an unsubstituted C$_{1-6}$ alkyl or an unsubstituted or a substituted benzyl.

A "di-substituted amine" refers to a "—NR$_A$R$_B$" in which R$_A$ and R$_B$ can be independently alkyl, alkenyl, alkynyl, cycloalkyl, cycloalkenyl, aryl, heteroaryl, heterocyclyl, aryl(alkyl), heteroaryl(alkyl) or heterocyclyl(alkyl). A mono-substituted amine may be substituted or unsubstituted. In some instances, a mono-substituted amine can be —NR$_A$R$_B$, wherein R$_A$ and R$_B$ can be independently an unsubstituted C$_{1-6}$ alkyl or an unsubstituted or a substituted benzyl.

A "ketoamide" group refers to a —C(=O)—C(=O)N(R$_A$R$_B$) group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A ketoamide may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the number of substituents is not specified (e.g., haloalkyl), there may be one or more substituents present. For example, "haloalkyl" may include one or more of the same or different halogens. As another example, "C$_1$-C$_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, C$_1$-C$_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

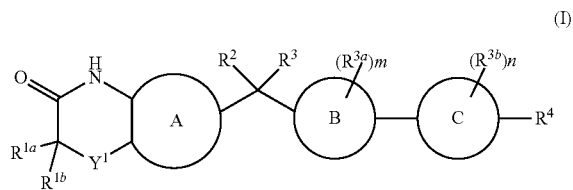

(I)

wherein: $Y^1$ can be O (oxygen), $CH_2$ or $CR^{Y1}R^{Y2}$, wherein $R^{Y1}$ and $R^{Y2}$ can be independently deuterium, halogen or an unsubstituted $C_{1-4}$ alkyl; Ring A can be selected from a pyrrole, a thiophene, a pyridine and a phenyl, wherein the pyrrole, the thiophene, the pyridine and the phenyl can be optionally substituted, and when substituted, each can be substituted 1 or more times with a moiety independently selected from deuterium, halogen, an unsubstituted $C_{1-4}$ alkyl, an unsubstituted $C_{1-4}$ alkoxy, an unsubstituted $C_{1-4}$ haloalkyl and an unsubstituted $C_{1-4}$ haloalkoxy; Ring B can be selected from an unsubstituted or a substituted 6-membered monocyclic nitrogen-containing heterocyclyl, an unsubstituted or a substituted 7-membered bicyclic nitrogen-containing heterocyclyl and an unsubstituted or a substituted 8-membered bicyclic nitrogen-containing heterocyclyl; Ring C can be selected from a pyrrole, a thiophene, a thiazole, a pyridine, a pyridazine, a pyrimidine, a pyrazine and a phenyl; $R^{1a}$ can be selected from hydrogen, deuterium, an unsubstituted $C_{2-4}$ alkyl, a substituted $C_{1-4}$ alkyl an unsubstituted $C_{2-4}$ alkenyl, an unsubstituted $C_{1-4}$ haloalkyl, an unsubstituted $C_{1-4}$ hydroxyalkyl, an unsubstituted monocyclic $C_{3-6}$ cycloalkyl, a substituted monocyclic $C_{3-6}$ cycloalkyl, an unsubstituted bicyclic $C_{5-8}$ cycloalkyl, a substituted bicyclic $C_{5-8}$ cycloalkyl, an unsubstituted monocyclic $C_{3-6}$ cycloalkyl(an unsubstituted $C_{1-4}$ alkyl), a substituted monocyclic $C_{3-6}$ cycloalkyl(an unsubstituted $C_{1-4}$ alkyl), an unsubstituted monocyclic $C_{3-6}$ cycloalkyl(an unsubstituted $C_{2-4}$ alkenyl) and a substituted monocyclic $C_{3-6}$ cycloalkyl(an unsubstituted $C_{2-4}$ alkenyl), wherein the substituted $C_{1-4}$ alkyl is substituted by 1 or more deuteriums, and wherein the monocyclic $C_{3-6}$ cycloalkyl, the substituted bicyclic $C_{5-8}$ cycloalkyl, the substituted monocyclic $C_{3-6}$ cycloalkyl(an unsubstituted $C_{1-4}$ alkyl) and the substituted monocyclic $C_{3-6}$ cycloalkyl(an unsubstituted $C_{2-4}$ alkenyl) are independently substituted by 1 or more substituents selected from deuterium and halogen; $R^{1b}$ can be hydrogen, an unsubstituted $C_{1-4}$ alkyl or an unsubstituted $C_{1-4}$ haloalkyl; or $R^{1a}$ and $R^{1b}$ can be taken together along with the carbon to which $R^{1a}$ and $R^{1b}$ are attached to form an unsubstituted or a substituted monocyclic 3-4-membered cycloalkyl or an unsubstituted or a substituted monocyclic 4-5 membered heterocyclyl, wherein the substituted monocyclic 3-4-membered cycloalkyl and the substituted monocyclic 4-5 membered heterocyclyl can be each substituted with one or more moieties independently selected from halogen, an unsubstituted $C_{1-3}$ alkyl and an unsubstituted $C_{1-3}$ haloalkyl; provided that when $R^{1b}$ is hydrogen, then $R^{1a}$ can be selected from deuterium, an unsubstituted $C_{2-4}$ alkyl, a substituted $C_{1-4}$ alkyl an unsubstituted $C_{2-4}$ alkenyl, an unsubstituted $C_{1-4}$ haloalkyl, an unsubstituted $C_{1-4}$ hydroxyalkyl, an unsubstituted monocyclic $C_{3-6}$ cycloalkyl, a substituted monocyclic $C_{3-6}$ cycloalkyl, an unsubstituted bicyclic $C_{5-8}$ cycloalkyl, a substituted bicyclic $C_{5-8}$ cycloalkyl, an unsubstituted monocyclic $C_{3-6}$ cycloalkyl(an unsubstituted $C_{1-4}$ alkyl), a substituted monocyclic $C_{3-6}$ cycloalkyl (an unsubstituted $C_{1-4}$ alkyl), an unsubstituted monocyclic $C_{3-6}$ cycloalkyl(an unsubstituted $C_{2-4}$ alkenyl) and a substituted monocyclic $C_{3-6}$ cycloalkyl(an unsubstituted $C_{2-4}$ alkenyl), wherein the substituted $C_{1-4}$ alkyl can be substituted by 1 or more deuteriums, and wherein the monocyclic $C_{3-6}$ cycloalkyl, the substituted bicyclic $C_{5-8}$ cycloalkyl, the substituted monocyclic $C_{3-6}$ cycloalkyl(an unsubstituted $C_{1-4}$ alkyl) and the substituted monocyclic $C_{3-6}$ cycloalkyl(an unsubstituted $C_{2-4}$ alkenyl) can be independently substituted by 1 or more substituents selected from deuterium and halogen; $R^2$ and $R^3$ can be independently hydrogen, deuterium or an unsubstituted $C_{1-4}$ alkyl; or $R^2$ and $R^3$ can be taken together along with the carbon to which $R^2$ and $R^3$ are attached to form an unsubstituted or a substituted monocyclic $C_{3-6}$ cycloalkyl; m can be 0, 1 or 2; n can be 0, 1 or 2; each $R^{3a}$ can be independently selected from deuterium, halogen, an unsubstituted $C_{1-4}$ alkyl, an unsubstituted $C_{1-4}$ haloalkyl, a cyano-substituted $C_{1-4}$ alkyl and an unsubstituted monocyclic $C_{3-6}$ cycloalkyl; each $R^{3b}$ can be independently selected from deuterium, halogen, an unsubstituted $C_{1-4}$ alkyl, a deuterium-substituted $C_{1-4}$ alkyl, an unsubstituted $C_{2-4}$ alkenyl, an unsubstituted $C_{1-4}$ haloalkyl, an unsubstituted monocyclic $C_{3-6}$ cycloalkyl and an unsubstituted monocyclic $C_{3-6}$ cycloalkyl(an unsubstituted $C_{1-4}$ alkyl); $R^4$ can be $-C(=O)NR^5R^6$; $R^5$ can be hydrogen or an unsubstituted $C_{1-4}$ alkyl; and $R^6$ can be hydrogen, an unsubstituted $C_{1-4}$ alkyl, a substituted $C_{1-4}$ alkyl, an unsubstituted monocyclic $C_{3-6}$ cycloalkyl, an unsubstituted bicyclic $C_{5-8}$ cycloalkyl, an unsubstituted monocyclic $C_{3-6}$ cycloalkyl(an unsubstituted $C_{1-4}$ alkyl) or an unsubstituted bicyclic $C_{5-8}$ cycloalkyl(an unsubstituted $C_{1-4}$ alkyl), wherein the substituted $C_{1-4}$ alkyl is substituted by 1 or more deuteriums.

In some embodiments, Ring A can be a pyrrole. In other embodiments, Ring A can be a thiophene. In still other embodiments, Ring A can be a pyridine. In yet still other embodiments, Ring A can be a phenyl. Each of the pyrrole, the thiophene, the pyridine and the phenyl can substituted with 1 or more times with a moiety (such as 1, 2 or 3 moieties) independently selected from deuterium, halogen (for example, F, Cl or Br), an unsubstituted $C_{1-4}$ alkyl (such as methyl, ethyl, n-propyl, iso-propyl, n-butyl, iso-butyl, sec-butyl and tert-butyl), an unsubstituted $C_{1-4}$ alkoxy (for example, methoxy, ethoxy, n-propoxy, iso-propoxy, n-butoxy, iso-butoxy, sec-butoxy and tert-butoxy), an unsubstituted $C_{1-4}$ haloalkyl (including —$CF_3$, —$CCl_3$, —$CHF_2$, —$C(CH_3)F_2$, —$CHCl_2$, —$CH_2F$, —$CH(CH_3)F$, —$CH_2CF_3$, —$CH_2Cl$, —$CH_2CH_2F$, —$CH_2CH_2Cl$, —$CH_2CH_2CH_2F$ and —$CH_2CH_2CH_2Cl$) and an unsubstituted $C_{1-4}$ haloalkoxy (such as —$OCF_3$, —$OCCl_3$, —$OCHF_2$, —$OC(CH_3)F_2$, —$OCHCl_2$, —$OCH_2F$, —$OCH(CH_3)F$, —$OCH_2CF_3$, —$OCH_2Cl$, —$OCH_2CH_2F$, —$OCH_2CH_2Cl$, —$OCH_2CH_2CH_2F$ and —$OCH_2CH_2CH_2Cl$). Examples of rings for Ring A include the following:

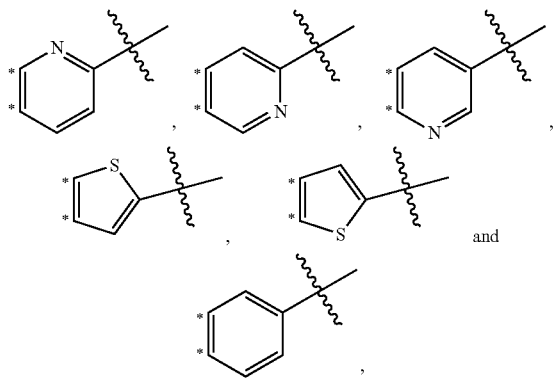

wherein the asterisks indicate the points of attachment to the morpholinone ring of Formula (I). For example, when Ring A is

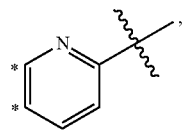 [SMILES: *c1ccccn1]

a compound of Formula (I), or a pharmaceutically acceptable salt thereof, can have the structure:

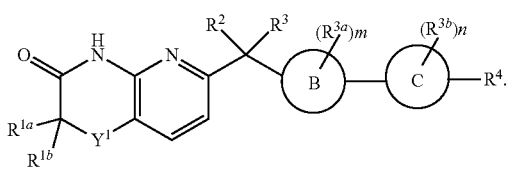

In some embodiments, Ring A can be

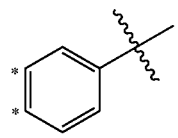

In other embodiments, Ring A can be

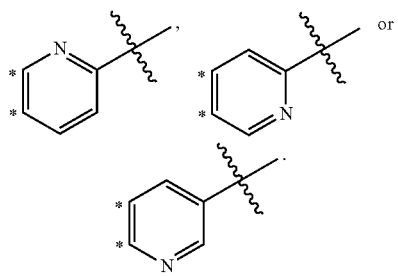

In some embodiments, $Y^1$ can be O such that Formula (I) can have the structure of Formula (Ia) (including pharmaceutically acceptable salts thereof). In other embodiments, $Y^1$ can be $CH_2$ such that Formula (I) can have the structure of Formula (Ib) (including pharmaceutically acceptable salts thereof). In still other embodiments, $Y^1$ can be $CR^{Y1}R^{Y2}$, wherein $R^{Y1}$ and $R^{Y2}$ can be independently deuterium, halogen (such as fluoro or chloro), an unsubstituted $C_{1-4}$ alkyl (for example, methyl, ethyl, n-propyl, iso-propyl, n-butyl, iso-butyl, sec-butyl and tert-butyl), an unsubstituted $C_{1-4}$ haloalkyl (such as —$CF_3$, —$CCl_3$, —$CHF_2$, —$C(CH_3)F_2$, —$CHCl_2$, —$CH_2F$, —$CH(CH_3)F$, —$CH_2CF_3$, —$CH_2Cl$, —$CH_2CH_2F$, —$CH_2CH_2Cl$, —$CH_2CH_2CH_2F$ and —$CH_2CH_2CH_2Cl$) or an unsubstituted monocyclic $C_{3-6}$ cycloalkyl (for example, cyclopropyl, cyclobutyl, cyclopentyl and cyclohexyl), such that Formula (I) can have the structure of Formula (Ic) (including pharmaceutically acceptable salts thereof) or the structure of Formula (Id) (including pharmaceutically acceptable salts thereof).

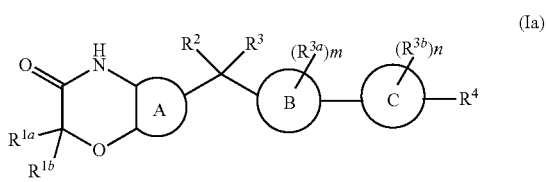

(Ia)

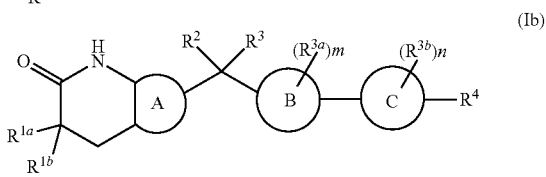

(Ib)

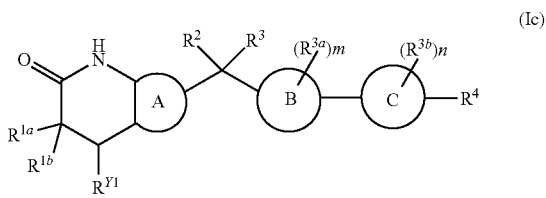

(Ic)

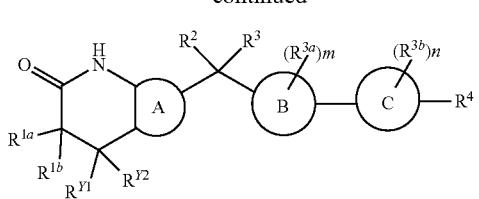

(Id)

A variety or heterocyclic ring(s) can be present for Ring B. The heterocyclyl for Ring B can be a monocyclic or a bicyclic ring. When Ring B is a bicyclic ring, the rings can be connected in a fused-fashion. In other instances, when Ring B is a bicyclic ring, the rings can be connected in a spiro-fashion. As provided herein, Ring B can include a ring nitrogen. Additional ring heteroatoms, such as an additional nitrogen, oxygen and/or sulfur, can be present in Ring B. In some embodiments, Ring B can be an unsubstituted 6-membered monocyclic nitrogen-containing heterocyclyl. In other embodiments, Ring B can be a substituted 6-membered monocyclic nitrogen-containing heterocyclyl. In still other embodiments, Ring B can be an unsubstituted 7-membered bicyclic nitrogen-containing heterocyclyl. In yet still other embodiments, Ring B can be a substituted 7-membered bicyclic nitrogen-containing heterocyclyl. In some embodiments, Ring B can be an unsubstituted 8-membered bicyclic nitrogen-containing heterocyclyl. In other embodiments, Ring B can be a substituted 8-membered bicyclic nitrogen-containing heterocyclyl. Exemplary Ring B groups include, but are not limited to, the following:

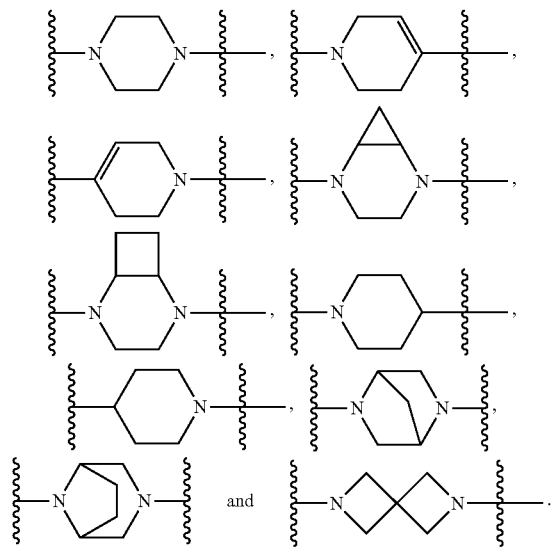

In some embodiments, Ring B can be

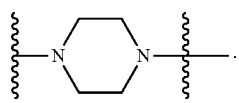

In some embodiments, Ring B can be unsubstituted when m is 0. In other embodiments, Ring B can be substituted with $R^{3a}$ when m is 1. In still other embodiments, Ring B can be substituted with $R^{3a}$ when m is 2. For example, each $R^{3a}$ can be independently deuterium, halogen, an unsubstituted $C_{1-4}$ alkyl, an unsubstituted $C_{1-4}$ haloalkyl, a cyano-substituted $C_{1-4}$ alkyl or an unsubstituted monocyclic $C_{3-6}$ cycloalkyl. Suitable halogens, unsubstituted $C_{1-4}$ alkyls, unsubstituted $C_{1-4}$ haloalkyls, cyano-substituted $C_{1-4}$ alkyls and an unsubstituted monocyclic $C_{3-6}$ cycloalkyls are described herein, and include chloro, fluoro, methyl, ethyl, n-propyl, isopropyl, n-butyl, iso-butyl, sec-butyl, tert-butyl, —$CF_3$, —$CHF_2$, —$C(CH_3)F_2$, —$CHCl_2$, —$CH_2F$, —$CH(CH_3)F$, —$CH_2CF_3$, —$CH_2Cl$, —$CH_2CH_2F$, —$CH_2CH_2Cl$, —$CH_2CH_2CH_2F$, —$CH_2CH_2CH_2Cl$, —$CH_2CN$, —$CH_2CH_2CN$, —$CH_2CH_2CH_2CN$, —$CH_2CH_2CH_2CH_2CN$, —$CH(CN)CH_3$, cyclopropyl, cyclobutyl, cyclopentyl and cyclohexyl.

In some embodiments, $R^4$ can be a C-amido. In some embodiments, Ring C can be pyrrole. In other embodiments, Ring C can be thiophene. In still other embodiments, Ring C can be thiazole. In yet still other embodiments, Ring C can be pyridine. In some embodiments, Ring C can be pyridazine. In other embodiments, Ring C can be pyrimidine. In still other embodiments, Ring C can be pyrazine. Exemplary rings for Ring C are as follows:

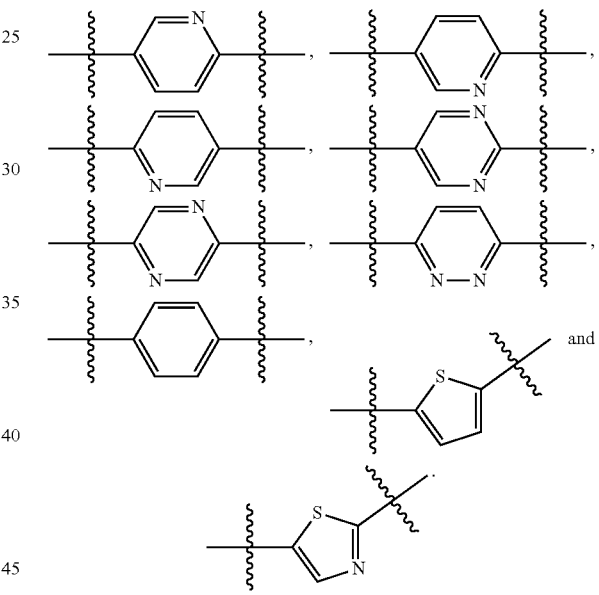

In some embodiments, Ring C can be

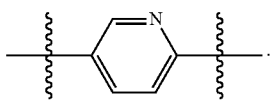

For the structures shown for Ring C, the bond on the right of the ring connects to $R^4$, for example,

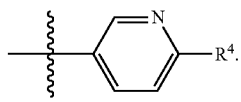

Additionally moieties can be present on Ring C. In some embodiments, Ring C can be substituted 1 or more times (such as 1 or 2 times) with $R^{3b}$, wherein each $R^{3b}$ can be independently selected from deuterium, halogen, an unsubstituted $C_{1-4}$ alkyl, a deuterium-substituted $C_{1-4}$ alkyl, an unsubstituted $C_{2-4}$ alkenyl, an unsubstituted $C_{1-4}$ haloalkyl, an unsubstituted monocyclic $C_{3-6}$ cycloalkyl and an unsubstituted monocyclic $C_{3-6}$ cycloalkyl(an unsubstituted $C_{1-4}$ alkyl). In some embodiments, Ring C can be substituted 1 or more times (such as 1, 2 or 3 times) with a moiety independently selected from deuterium, F, Cl, Br, methyl, ethyl, n-propyl, iso-propyl, n-butyl, iso-butyl, sec-butyl, tert-butyl, ethenyl, propenyl, butenyl, —$CF_3$, —$CHF_2$, —$C(CH_3)F_2$, —$CHCl_2$, —$CH_2F$, —$CH(CH_3)F$, —$CH_2CF_3$, —$CH_2Cl$, —$CH_2CH_2F$, —$CH_2CH_2Cl$, —$CH_2CH_2CH_2F$, —$CH_2CH_2CH_2Cl$, —$CD_3$, —$CD_2H$, —$CDH_2$, —$CHDCH_3$, —$CH_2CHD_2$, —$CH_2CH_2D$,
  —$CHDCHD_2$, —$CHDCH_2D$, —$CD_2CHD_2$, —$CD_2CH_2D$, —$CH_2CD_3$, —$CD_2CH_3$—$CD_2CD_3$, cyclopropyl, cyclobutyl, cyclopentyl, cyclohexyl, cyclopropyl-$CH_2$—, cyclobutyl-$CH_2$—, cyclopentyl-$CH_2$—, cyclohexyl-$CH_2$—, cyclopropyl-$CH_2CH_2$—, cyclobutyl-$CH_2CH_2$—, cyclopentyl-$CH_2CH_2$—, cyclohexyl-$CH_2CH_2$—, cyclopropyl-$CH_2CH_2CH_2$—, cyclobutyl-$CH_2CH_2CH_2$—, cyclopentyl-$CH_2CH_2CH_2$—, cyclohexyl-$CH_2CH_2CH_2$—, cyclopropyl-$CH_2CH_2CH_2CH_2$—, cyclobutyl-$CH_2CH_2CH_2CH_2$—, cyclopentyl-$CH_2CH_2CH_2CH_2$— and cyclohexyl-$CH_2CH_2CH_2CH_2$—.

As provided herein Ring A and Ring C can be substituted. In some embodiments, both Ring A and Ring C can be substituted. For example, both Ring A and Ring C can be mono-substituted. In some embodiments, Ring A can be substituted (such as mono-substituted) with deuterium, halogen, an unsubstituted $C_{1-4}$ alkyl, an unsubstituted $C_{1-4}$ alkoxy, an unsubstituted $C_{1-4}$ haloalkyl or an unsubstituted $C_{1-4}$ haloalkoxy; and Ring C can be substituted (such as mono-substituted) with deuterium, halogen, an unsubstituted $C_{1-4}$ alkyl, a deuterium-substituted $C_{1-4}$ alkyl, an unsubstituted $C_{2-4}$ alkenyl, an unsubstituted $C_{1-4}$ haloalkyl, an unsubstituted monocyclic $C_{3-6}$ cycloalkyl or an unsubstituted monocyclic $C_{3-6}$ cycloalkyl(an unsubstituted $C_{1-4}$ alkyl). In some embodiments, Ring A can be substituted (such as mono-substituted) with deuterium, halogen or an unsubstituted $C_{1-4}$ alkyl; and Ring C can be substituted (such as mono-substituted) with deuterium, halogen, an unsubstituted $C_{1-4}$ alkyl or a deuterium-substituted $C_{1-4}$ alkyl. In some embodiments, Ring A can be substituted (such as mono-substituted) with halogen or an unsubstituted $C_{1-4}$ alkyl; and Ring C can be substituted (such as mono-substituted) with halogen or an unsubstituted $C_{1-4}$ alkyl. In some embodiments, Ring A can be a substituted phenyl substituted 1 or more times with a moiety independently selected from deuterium, halogen, an unsubstituted $C_{1-4}$ alkyl and an unsubstituted $C_{1-4}$ alkoxy; Ring C can be pyridine; n can be 1 or 2; and each $R^{3b}$ can be independently selected from deuterium, halogen, an unsubstituted $C_{1-4}$ alkyl, a deuterium-substituted $C_{1-4}$ alkyl and an unsubstituted $C_{1-4}$ haloalkyl. In other embodiments, Ring A can be a substituted phenyl substituted 1 or more times with a moiety independently selected from deuterium, halogen, an unsubstituted $C_{1-4}$ alkyl and an unsubstituted $C_{1-4}$ alkoxy; Ring C can be pyridine; n can be 1 or 2; and each $R^{3b}$ can be independently selected from deuterium, halogen, an unsubstituted $C_{1-4}$ alkyl, a deuterium-substituted $C_{1-4}$ alkyl and an unsubstituted $C_{1-4}$ haloalkyl. In some embodiments, Ring A can be

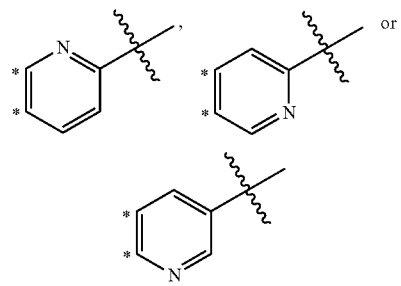

substituted 1 or more times with a moiety independently selected from deuterium, halogen, an unsubstituted $C_{1-4}$ alkyl and an unsubstituted $C_{1-4}$ alkoxy; Ring C can be pyridine; n can be 1 or 2; and each $R^{3b}$ can be independently selected from deuterium, halogen, an unsubstituted $C_{1-4}$ alkyl, a deuterium-substituted $C_{1-4}$ alkyl and an unsubstituted $C_{1-4}$ haloalkyl. Examples of halogens, unsubstituted $C_{1-4}$ alkyls, unsubstituted $C_{1-4}$ alkoxys, unsubstituted $C_{14}$ haloalkyls, unsubstituted $C_{1-4}$ haloalkoxys, deuterium-substituted $C_{1-4}$ alkyls, unsubstituted $C_{2-4}$ alkenyls, unsubstituted monocyclic $C_{3-6}$ cycloalkyls and unsubstituted monocyclic $C_{3-6}$ cycloalkyl(an unsubstituted $C_{1-4}$ alkyl)s are described herein and include deuterium, F, Cl, Br, methyl, ethyl, n-propyl, iso-propyl, n-butyl, iso-butyl, sec-butyl, tert-butyl, ethenyl, propenyl, butenyl, methoxy, ethoxy, n-propoxy, iso-propoxy, n-butoxy, iso-butoxy, sec-butoxy, tert-butoxy, —$CF_3$, —$CHF_2$, —$C(CH_3)F_2$, —$CHCl_2$, —$CH_2F$, —$CH(CH_3)F$, —$CH_2CF_3$, —$CH_2Cl$, —$CH_2CH_2F$, —$CH_2CH_2Cl$, —$CH_2CH_2CH_2F$, —$CH_2CH_2CH_2Cl$, —$OCF_3$, —$OCCl_3$, —$OCHF_2$, —$OC(CH_3)F_2$, —$OCHCl_2$, —$OCH_2F$, —$OCH(CH_3)F$, —$OCH_2CF_3$, —$OCH_2Cl$, —$OCH_2CH_2F$, —$OCH_2CH_2Cl$, —$OCH_2CH_2CH_2F$, —$OCH_2CH_2CH_2Cl$, —$CD_3$, —$CD_2H$, —$CDH_2$, —$CHDCH_3$, —$CH_2CHD_2$, —$CH_2CH_2D$, —$CHDCHD_2$, —$CHDCH_2D$, —$CD_2CHD_2$, —$CD_2CH_2D$, —$CH_2CD_3$, —$CD_2CH_3$—$CD_2CD_3$, cyclopropyl, cyclobutyl, cyclopentyl, cyclohexyl, cyclopropyl-$CH_2$—, cyclobutyl-$CH_2$—, cyclopentyl-$CH_2$—, cyclohexyl-$CH_2$—, cyclopropyl-$CH_2CH_2$—, cyclobutyl-$CH_2CH_2$—, cyclopentyl-$CH_2CH_2$—, cyclohexyl-$CH_2CH_2$—, cyclopropyl-$CH_2CH_2CH_2$—, cyclobutyl-$CH_2CH_2CH_2$—, cyclopentyl-$CH_2CH_2CH_2$—, cyclohexyl-$CH_2CH_2CH_2$—, cyclopropyl-$CH_2CH_2CH_2CH_2$—, cyclobutyl-$CH_2CH_2CH_2CH_2$—, cyclopentyl-$CH_2CH_2CH_2CH_2$— and cyclohexyl-$CH_2CH_2CH_2CH_2$—. In some embodiments, Ring A can be mono-substituted with F, Cl, Br, methyl, ethyl, n-propyl, iso-propyl, n-butyl, iso-butyl, sec-butyl or tert-butyl; and Ring C can be mono-substituted with F, Cl, Br, methyl, ethyl, n-propyl, iso-propyl, n-butyl, iso-butyl, sec-butyl or tert-butyl.

In some embodiments, Ring A can be

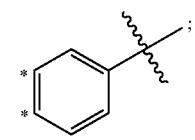

Ring B can be

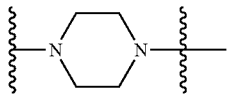

Ring C can be

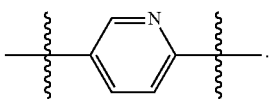 [SMILES: *c1ccc(*)nc1]

In other embodiments, Ring A can be

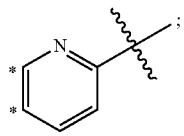 [SMILES: *c1ccccn1]

Ring B can be

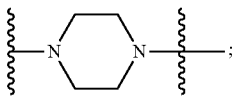 [SMILES: *N1CCN(*)CC1]

and Ring C can be

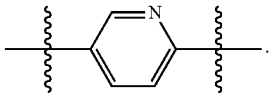 [SMILES: *c1ccc(*)nc1]

In still other embodiments, Ring A can be

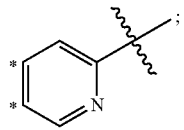 [SMILES: *c1ccccn1]

Ring B can be

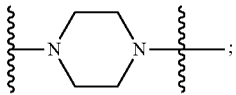

and Ring C can be

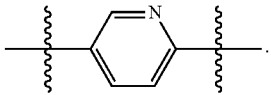 [SMILES: *c1ccc(*)nc1]

In yet still other embodiments, Ring A can be

Ring B can be

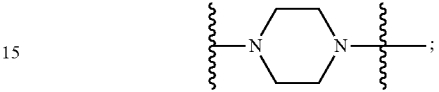

and Ring C can be

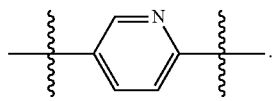

As provided herein, a —C(=O)NR$^5$R$^6$ group is attached to Ring C. In some embodiments, R$^5$ can be hydrogen, such that Ring C can be substituted with —C(=O)NHR$^6$. In other embodiments, R$^5$ can be an unsubstituted $C_{1-4}$ alkyl, for example, methyl, ethyl, n-propyl, iso-propyl, n-butyl, iso-butyl, sec-butyl and tert-butyl. In some embodiments, Ring C can be substituted with —C(=O)N(CH$_3$)R$^6$.

In addition to —C(=O)NR$^5$R$^6$, Ring C can include one or two other groups, such as R$^{3b}$. In some embodiments, when n is 0, Ring B can be unsubstituted except for —C(=O)NR$^5$R$^6$. In other embodiments, when n is 1, Ring B can be substituted with one R$^{3b}$ group. In still other embodiments, when n is 2, Ring B can be substituted with two R$^{3b}$ groups. As provided herein, each R$^{3b}$ can be independently selected from deuterium, halogen, an unsubstituted $C_{1-4}$ alkyl, an unsubstituted $C_{1-4}$ haloalkyl or an unsubstituted monocyclic $C_{3-6}$ cycloalkyl. Exemplary moieties for each R$^{3b}$ can be deuterium, chloro, fluoro, methyl, ethyl, n-propyl, isopropyl, n-butyl, iso-butyl, sec-butyl, tert-butyl, —CF$_3$, —CHF$_2$, —C(CH$_3$)F$_2$, —CHCl$_2$, —CH$_2$F, —CH(CH$_3$)F, —CH$_2$CF$_3$, —CH$_2$Cl, —CH$_2$CH$_2$F, —CH$_2$CH$_2$Cl, —CH$_2$CH$_2$CH$_2$F, —CH$_2$CH$_2$CH$_2$Cl, cyclopropyl, cyclobutyl, cyclopentyl and cyclohexyl.

In some embodiments, R$^6$ can be an unsubstituted monocyclic $C_{3-6}$ cycloalkyl. In other embodiments, R$^6$ can be an unsubstituted bicyclic $C_{5-8}$ cycloalkyl. In still other embodiments, R$^6$ can be an unsubstituted monocyclic $C_{3-6}$ cycloalkyl(an unsubstituted $C_{1-4}$ alkyl). In yet still other embodiments, R$^6$ can be an unsubstituted bicyclic $C_{5-8}$ cycloalkyl (an unsubstituted $C_{1-4}$ alkyl). The monocyclic $C_{3-6}$ cycloalkyl that can be present for R$^6$ and/or part of an unsubstituted monocyclic $C_{3-6}$ cycloalkyl(an unsubstituted $C_{1-4}$ alkyl) for R$^6$ can be cyclopropyl, cyclobutyl, cyclopentyl and cyclohexyl. Examples of bicyclic $C_{5-8}$ cycloalkyls for R$^6$ and/or part of an unsubstituted bicyclic $C_{5-8}$ cycloalkyl for R$^6$ include bicyclo[1.1.1]pentyl, bicyclo[2.2.1]heptane, bicyclo[3.1.1]heptane, bicyclo[3.2.1]octane and bicyclo[2.2.2]octane. In some embodiments, R$^6$ can be an unsubstituted bicyclic $C_{5-8}$ cycloalkyl-CH$_3$—, where examples of bicyclic $C_{5-8}$ cycloalkyls are described herein.

As provided herein, the morpholinone ring of Formula (I) can be unsubstituted or substituted. In some embodiments, $R^{1a}$ can be hydrogen. In some embodiments, $R^{1a}$ can be deuterium. In still other embodiments, $R^{1a}$ can be an unsubstituted $C_{2-4}$ alkyl, such as ethyl, n-propyl, iso-propyl, n-butyl, iso-butyl, sec-butyl and tert-butyl. In yet still other embodiments, $R^{1a}$ can be a substituted $C_{1-4}$ alkyl that can be substituted by 1 or more deuteriums. For example, Ria can be —$CD_3$, —$CD_2H$, —$CDH_2$, —$CHDCH_3$, —$CH_2CHD_2$, —$CH_2CH_2D$, —$CHDCHD_2$, —$CHDCH_2D$, —$CD_2CHD_2$, —$CD_2CH_2D$, —$CH_2CD_3$, —$CD_2CH_3$—$CD_2CD_3$, —$CD_2CD_2CD_3$ or —$CD_2CD_2CD_2CD_3$. In some embodiments, $R^{1a}$ can be an unsubstituted $C_{2-4}$ alkenyl. Exemplary an unsubstituted $C_{2-4}$ alkenyls, include ethenyl, propenyl, 2-methyl-propenyl and butenyl. In other embodiments, $R^{1a}$ can be $C_{1-4}$ haloalkyl. For example, when $R^{1a}$ is an unsubstituted $C_{1-4}$ haloalkyl, $R^{1a}$ can be —$CF_3$, —$CHF_2$, —$C(CH_3)F_2$, —$CHCl_2$, —$CH_2F$, —$CH(CH_3)F$, —$CH_2CF_3$, —$CH_2CHF_2$, —$CH_2Cl$, —$CH_2CH_2F$, —$CH_2CH_2Cl$, —$CH_2CH_2CH_2F$ and —$CH_2CH_2CH_2Cl$. In still other embodiments, $R^{1a}$ can be an unsubstituted $C_{1-4}$ hydroxyalkyl, such as —$CH_2$—OH, —$CH_2CH_2$—OH, —$CH_2CH_2CH_2$—OH and —$CH_2CH_2CH_2CH_2$—OH. In yet still other embodiments, $R^{1a}$ can be an unsubstituted monocyclic $C_{3-6}$ cycloalkyl. In some embodiments, $R^{1a}$ can be a monocyclic $C_{3-6}$ cycloalkyl substituted by 1 or more substituents (such as 1, 2, 3, 4, 5 or 6 substituents) selected from deuterium and halogen. In other embodiments, $R^{1a}$ can be an unsubstituted bicyclic $C_{5-8}$ cycloalkyl. In still other embodiments, $R^{1a}$ can be a bicyclic $C_{5-8}$ cycloalkyl substituted by 1 or more substituents selected from deuterium and halogen. In yet still other embodiments, $R^{1a}$ can be an unsubstituted monocyclic $C_{3-6}$ cycloalkyl(an unsubstituted $C_{1-4}$ alkyl). In some embodiments, $R^{1a}$ can be an unsubstituted monocyclic $C_{3-6}$ cycloalkyl(an unsubstituted $C_{2-4}$ alkenyl). In other embodiments, $R^{1a}$ can be a substituted monocyclic $C_{3-6}$ cycloalkyl(an unsubstituted $C_{2-4}$ alkenyl). In some embodiments, $R^{1a}$ can be a deuterium-substituted monocyclic $C_{3-6}$ cycloalkyl. In other embodiments, $R^{1a}$ can be a deuterium-substituted monocyclic $C_{3-6}$ cycloalkyl(an unsubstituted $C_{14}$ alkyl). In still other embodiments, $R^{1a}$ can be a deuterium-substituted monocyclic $C_{3-6}$ cycloalkyl(an unsubstituted $C_{2-4}$ alkenyl). When $R^{1a}$ is a deuterium-substituted monocyclic $C_{3-6}$ cycloalkyl, a deuterium-substituted monocyclic $C_{3-6}$ cycloalkyl(an unsubstituted $C_{1-4}$ alkyl) or be a deuterium-substituted monocyclic $C_{3-6}$ cycloalkyl(an unsubstituted $C_{2-4}$ alkenyl), one or more hydrogens (for example, 1, 2, 3, 4, 5 or 6 hydrogen) can be placed with deuteriums. In other embodiments, $R^{1a}$ can be a halogen-substituted monocyclic $C_{3-6}$ cycloalkyl. In other embodiments, $R^{1a}$ can be a halogen-substituted monocyclic $C_{3-6}$ cycloalkyl(an unsubstituted $C_{1-4}$ alkyl). In still other embodiments, $R^{1a}$ can be a halogen-substituted monocyclic $C_{3-6}$ cycloalkyl(an unsubstituted $C_{2-4}$ alkenyl). When $R^{1a}$ is a halogen-substituted monocyclic $C_{3-6}$ cycloalkyl, a halogen-substituted monocyclic $C_{3-6}$ cycloalkyl(an unsubstituted $C_{1-4}$ alkyl) or be a halogen-substituted monocyclic $C_{3-6}$ cycloalkyl(an unsubstituted $C_{2-4}$ alkenyl), one or more hydrogens (for example, 1, 2, 3, 4, 5 or 6 hydrogen) can be placed with halogens. In some embodiments, $R^{1a}$ can be a monocyclic $C_{3-6}$ cycloalkyl substituted with both deuterium(s) and halogen(s). In other embodiments, $R^{1a}$ can be a monocyclic $C_{3-6}$ cycloalkyl(an unsubstituted $C_{1-4}$ alkyl) substituted with both deuterium(s) and halogen(s). In still other embodiments, $R^{1a}$ can be a monocyclic $C_{3-6}$ cycloalkyl(an unsubstituted $C_{2-4}$ alkenyl) substituted with both deuterium(s) and halogen(s). Possible cycloalkyls that can be present for a monocyclic $C_{3-6}$ cycloalkyl, a monocyclic $C_{3-6}$ cycloalkyl(an unsubstituted $C_{1-4}$ alkyl) and a monocyclic $C_{3-6}$ cycloalkyl(an unsubstituted $C_{2-4}$ alkenyl) include cyclopropyl, cyclobutyl, cyclopentyl and cyclohexyl. Exemplary bicyclic $C_{5-8}$ cycloalkyls that can be present for a bicyclic $C_{5-8}$ cycloalkyl include, but are not limited to, bicyclo[1.1.1]pentyl, bicyclo[2.2.1]heptane, bicyclo[3.1.1]heptane, bicyclo[3.2.1]octane and bicyclo[2.2.2]octane. The $C_{1-4}$ alkyl of a monocyclic $C_{3-6}$ cycloalkyl(an unsubstituted $C_{1-4}$ alkyl) and the $C_{2-4}$ alkenyl of a monocyclic $C_{3-6}$ cycloalkyl(an unsubstituted $C_{2-4}$ alkenyl) of can be straight-chained or branched. Exemplary $C_{14}$ alkyls of a monocyclic $C_{3-6}$ cycloalkyl(an unsubstituted $C_{1-4}$ alkyl) include —$CH_2$—, —$CH_2CH_2$—, —$CH_2CH_2CH_2$— and —$CH_2CH_2CH_2CH_2$—. Exemplary $C_{2-4}$ alkenyls of a monocyclic $C_{3-6}$ cycloalkyl(an unsubstituted $C_{2-4}$ alkenyl) include —$CH$=$CH_2$—, —$CH$=$CHCH_2$—, —$CH_2CH$=$CH_2$— —$CH$=$C$=$CH_2$—, —$CH$=$CHCH_2CH_2$—, —$CH_2CH$=$CHCH_2$— and —$CH_2CH_2CH$=$CH$—.

In some embodiments, $R^{1b}$ can be hydrogen. In other embodiments, Rib can be an unsubstituted $C_{1-4}$ alkyl such as methyl, ethyl, n-propyl, iso-propyl, n-butyl, iso-butyl, sec-butyl and tert-butyl. In still other embodiments, $R^{1b}$ can be an unsubstituted $C_{1-4}$ haloalkyl, including those described herein. Examples of unsubstituted $C_{1-4}$ haloalkyls for $R^{1b}$ include —$CF_3$, —$CCl_3$, —$CHF_2$, —$C(CH_3)F_2$, —$CHCl_2$, —$CH_2F$, —$CH(CH_3)F$, —$CH_2CF_3$, —$CH_2Cl$, —$CH_2CH_2F$, —$CH_2CH_2Cl$, —$CH_2CH_2CH_2F$ and —$CH_2CH_2CH_2Cl$. In some embodiments, when $R^{1a}$ is hydrogen, then $R^{1b}$ can be hydrogen, an unsubstituted $C_{2-4}$ alkyl or an unsubstituted $C_{1-4}$ haloalkyl.

When $R^{1a}$ is a non-hydrogen moiety, the carbon to which $R^{1a}$ and $R^{1b}$ are attached can be a chiral center. For example, when $R^{1a}$ is an unsubstituted $C_{2-4}$ alkyl and $R^{1b}$ can be hydrogen, the carbon to which $R^{1a}$ and $R^{1b}$ are attached can be in the (R)-configuration or the (S)-configuration. In some embodiments, $R^{1a}$ can be a hydrogen moiety; $R^{1b}$ can be a non-hydrogen; and the carbon to which $R^{1a}$ and $R^{1b}$ are attached can be in the (R)-configuration such that a compound of Formula (I) has the structure of a compound of Formula (Id). In some embodiments, $R^{1a}$ can be a hydrogen moiety; $R^{1b}$ can be a non-hydrogen; and the carbon to which $R^{1a}$ and $R^{1b}$ are attached can be in the (S)-configuration such that a compound of Formula (I) has the structure of a compound of Formula (Ie). In some embodiments, when $R^{1b}$ is hydrogen, then $R^{1a}$ can be selected from deuterium, an unsubstituted $C_{2-4}$ alkyl, a substituted $C_{1-4}$ alkyl an unsubstituted $C_{2-4}$ alkenyl, an unsubstituted $C_{1-4}$ haloalkyl, an unsubstituted $C_{1-4}$ hydroxyalkyl, an unsubstituted monocyclic $C_{3-6}$ cycloalkyl, a substituted monocyclic $C_{3-6}$ cycloalkyl, an unsubstituted bicyclic $C_{5-8}$ cycloalkyl, a substituted bicyclic $C_{5-8}$ cycloalkyl, an unsubstituted monocyclic $C_{3-6}$ cycloalkyl(an unsubstituted $C_{1-4}$ alkyl), a substituted monocyclic $C_{3-6}$ cycloalkyl(an unsubstituted $C_{1-4}$ alkyl), an unsubstituted monocyclic $C_{3-6}$ cycloalkyl(an unsubstituted $C_{2-4}$ alkenyl) and a substituted monocyclic $C_{3-6}$ cycloalkyl(an unsubstituted $C_{2-4}$ alkenyl). ). In other embodiments, when $R^{1b}$ is hydrogen, then $R^{1a}$ can be selected from deuterium, an unsubstituted $C_{2-4}$ alkyl, a substituted $C_{1-4}$ alkyl an unsubstituted $C_{2-4}$ alkenyl, an unsubstituted $C_{1-4}$ haloalkyl, an unsubstituted $C_{1-4}$ hydroxyalkyl, an unsubstituted bicyclic $C_{5-8}$ cycloalkyl, a substituted bicyclic $C_{5-8}$ cycloalkyl, an unsubstituted monocyclic $C_{3-6}$ cycloalkyl(an unsubstituted $C_{1-4}$ alkyl), a substituted monocyclic $C_{3-6}$ cycloalkyl(an unsubstituted $C_{1-4}$ alkyl), an unsubstituted monocyclic $C_{3-6}$ cycloalkyl(an unsubstituted $C_{2-4}$ alkenyl) and a substituted monocyclic $C_{3-6}$ cycloalkyl(an unsubstituted $C_{2-4}$ alkenyl). ). In still other embodiments, when $R^{1b}$ is hydrogen, then $R^{1a}$ can be selected from deuterium, an unsubstituted $C_{2-4}$ alkyl, a substituted $C_{1-4}$ alkyl an unsubstituted $C_{2-4}$ alkenyl, an unsubstituted $C_{1-4}$ haloalkyl and an unsubstituted $C_{1-4}$ hydroxyalkyl. In yet still other embodiments, when $R^{1b}$ is hydrogen, then $R^{1a}$ can be an unsubstituted $C_{2-4}$ alkyl. In some embodiments, when $R^{1b}$ is hydrogen, then $R^{1a}$ can be an unsubstituted $C_{1-4}$ haloalkyl. In some embodiments, when $R^{1b}$ is hydrogen, then $R^{1a}$ can be an unsubstituted monocyclic $C_{3-6}$ cycloalkyl. In other embodiments, when $R^{1b}$ is hydrogen, then $R^{1a}$ can be a substituted monocyclic $C_{3-6}$ cycloalkyl. In still other embodiments, when $R^{1b}$ is hydrogen, then $R^{1a}$ can be an unsubstituted monocyclic $C_{3-6}$ cycloalkyl(an unsubstituted $C_{1-4}$ alkyl). In yet still other embodiments, when $R^{1b}$ is hydrogen, then $R^{1a}$ can be a substituted monocyclic $C_{3-6}$ cycloalkyl(an unsubstituted $C_{1-4}$ alkyl).

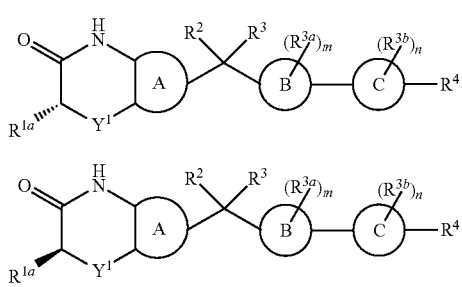

As provided herein, $R^{1a}$ and $R^{1b}$ can be taken together along with the carbon to which $R^{1a}$ and $R^{1b}$ are attached to form an unsubstituted or a substituted monocyclic 3-4-membered cycloalkyl or an unsubstituted or a substituted monocyclic 4-5 membered heterocyclyl, such that the formed monocyclic ring is spiro-connected to the morpholinone ring of Formula (I). In some embodiments, $R^{1a}$ and $R^{1b}$ can be taken together along with the carbon to which $R^{1a}$ and $R^{1b}$ are attached to form an unsubstituted monocyclic 3-4-membered cycloalkyl. In other embodiments, $R^{1a}$ and $R^{1b}$ can be taken together along with the carbon to which $R^{1a}$ and $R^{1b}$ are attached to form a substituted monocyclic 3-4-membered cycloalkyl where the monocyclic 3-4-membered cycloalkyl can be substituted with one or more (such as 1, 2 or 3) moieties independently selected from halogen, an unsubstituted $C_{1-3}$ alkyl and an unsubstituted $C_{1-3}$ haloalkyl. In still other embodiments, $R^{1a}$ and $R^{1b}$ can be taken together along with the carbon to which $R^{1a}$ and $R^{1b}$ are attached to form an unsubstituted 4-membered heterocyclyl. In yet still other embodiments, Ria and $R^{1b}$ can be taken together along with the carbon to which $R^{1a}$ and $R^{1b}$ are attached to form a substituted 4-membered heterocyclyl substituted with one or more (such as 1, 2 or 3) moieties independently selected from halogen, an unsubstituted $C_{1-3}$ alkyl and an unsubstituted $C_{1-3}$ haloalkyl.

Exemplary moieties that can be present on a substituted 3-4-membered cycloalkyl and/or a substituted monocyclic 4-5 membered heterocyclyl include fluoro, chloro, methyl, ethyl, n-propyl, iso-propyl, $-CF_3$, $-CCl_3$, $-CHF_2$, $-C(CH_3)F_2$, $-CHCl_2$, $-CH_2F$, $CH(CH_3)F$, $-CH_2CF_3$, $-CH_2Cl$, $-CH_2CH_2F$, $-CH_2CH_2Cl$, $-CH_2CH_2CH_2F$ and $-CH_2CH_2CH_2Cl$. A non-limiting list of 3-4-membered cycloalkyls and monocyclic 4-5 membered heterocyclyls include the following: cyclopropyl, cyclobutyl, oxetane, thietane, azetidine, tetrahydrofuran, tetrahydrothiophene and pyrrolidine. In some embodiments, $R^{1a}$ and $R^{1b}$ can be taken together along with the carbon to which $R^{1a}$ and $R^{1b}$ are attached to form cyclic group selected from

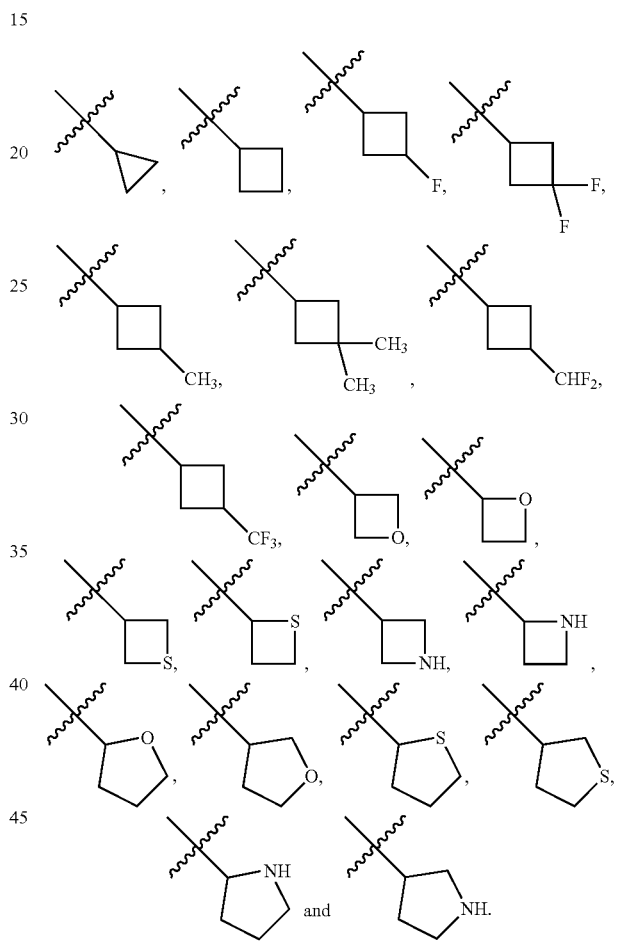

In some embodiments, $R^2$ and $R^3$ can be each hydrogen. In other embodiments, $R^2$ and $R^3$ can be each deuterium. In other embodiments, $R^2$ and $R^3$ can be each an unsubstituted $C_{1-4}$ alkyl. For example, $R^2$ and $R^3$ can be independently selected from methyl, ethyl, n-propyl, iso-propyl, n-butyl, iso-butyl, sec-butyl and tert-butyl. In still other embodiments, one of $R^2$ and $R^3$ can be deuterium; and the other of $R^2$ and $R^3$ can be hydrogen or an unsubstituted $C_{1-4}$ alkyl. In some embodiments, $R^2$ and $R^3$ can be taken together along with the carbon to which $R^2$ and $R^3$ are attached to form an unsubstituted or a substituted monocyclic $C_{3-6}$ cycloalkyl. For example, $R^2$ and $R^3$ can be taken together along with the carbon to which $R^2$ and $R^3$ are attached to form an unsubstituted or a substituted cyclopropyl, an unsubstituted or a substituted cyclobutyl, an unsubstituted or a substituted cyclopentyl or an unsubstituted or a substituted cyclohexyl.

In some embodiments, a compound of Formula (I), or a pharmaceutically acceptable salt thereof, can be where $Y^1$ can be O (oxygen), $CH_2$ or $CHR^{Y1}$, wherein $R^{Y1}$ is deuterium, halogen or an unsubstituted $C_{1-4}$ alkyl; Ring A can be selected from a pyrrole, a thiophene, a pyridine and a phenyl, wherein the pyrrole, the thiophene, the pyridine and the phenyl can be optionally substituted, and when substituted, each can be substituted 1 or more times with a moiety independently selected from deuterium, halogen, an unsubstituted $C_{1-4}$ alkyl and an unsubstituted $C_{1-4}$ haloalkyl; Ring B can be selected from an unsubstituted or a substituted 6-membered monocyclic nitrogen-containing heterocyclyl, an unsubstituted or a substituted 7-membered bicyclic nitrogen-containing heterocyclyl and an unsubstituted or a substituted 8-membered bicyclic nitrogen-containing heterocyclyl; Ring C can be selected from a pyrrole, a thiophene, a thiazole, a pyridine, a pyridazine, a pyrimidine, a pyrazine and a phenyl, wherein the pyrrole, the thiophene, the thiazole, the pyridine, the pyridazine, the pyrimidine, the pyrazine and the phenyl can be optionally substituted, and when substituted, each can be substituted 1 or more times with a moiety independently selected from deuterium, halogen, an unsubstituted $C_{1-4}$ alkyl, an unsubstituted $C_{2-4}$ alkenyl, an unsubstituted monocyclic $C_{3-6}$ cycloalkyl(an unsubstituted $C_{14}$ alkyl) and an unsubstituted $C_{1-4}$ haloalkyl; $R^{1a}$ can be selected from hydrogen, an unsubstituted $C_{2-4}$ alkyl, an unsubstituted $C_{2-4}$ alkenyl, an unsubstituted $C_{1-4}$ haloalkyl, an unsubstituted $C_{14}$ hydroxyalkyl, an unsubstituted monocyclic $C_{3-6}$ cycloalkyl, an unsubstituted bicyclic $C_{5-8}$ cycloalkyl, an unsubstituted monocyclic $C_{3-6}$ cycloalkyl(an unsubstituted $C_{1-4}$ alkyl), a substituted monocyclic $C_{3-6}$ cycloalkyl(an unsubstituted $C_{1-4}$ alkyl), an unsubstituted monocyclic $C_{3-6}$ cycloalkyl(an unsubstituted $C_{1-4}$ alkenyl) and a substituted monocyclic $C_{3-6}$ cycloalkyl(an unsubstituted $C_{1-4}$ alkenyl), wherein the substituted monocyclic $C_{3-6}$ cycloalkyl(an unsubstituted $C_{1-4}$ alkyl) can be substituted by 1 or more deuteriums; $R^{1b}$ can be hydrogen, an unsubstituted $C_{14}$ alkyl or an unsubstituted $C_{1-4}$ haloalkyl; or $R^{1a}$ and $R^{1b}$ can be taken together along with the carbon to which $R^{1a}$ and $R^{1b}$ are attached to form an unsubstituted or a substituted monocyclic 3-4-membered cycloalkyl or an unsubstituted or a substituted monocyclic 4-5 membered heterocyclyl, wherein the substituted monocyclic 3-4-membered cycloalkyl and the substituted monocyclic 4-5 membered heterocyclyl can be each substituted with one or more moieties independently selected from halogen, an unsubstituted $C_{1-3}$ alkyl and an unsubstituted $C_{1-3}$ haloalkyl; provided that when $R^{1a}$ is hydrogen, then $R^{1b}$ can be hydrogen, an unsubstituted $C_{2-4}$ alkyl or an unsubstituted $C_{1-4}$ haloalkyl; $R^2$ and $R^3$ can be independently hydrogen, deuterium or an unsubstituted $C_{1-4}$ alkyl; or $R^2$ and $R^3$ can be taken together along with the carbon to which $R^2$ and $R^3$ are attached to form an unsubstituted or a substituted monocyclic $C_{3-6}$ cycloalkyl; m can be 0 or 1; n can be 0, 1 or 2; $R^{3a}$ can be deuterium, halogen, an unsubstituted $C_{1-4}$ alkyl, an unsubstituted $C_{1-4}$ haloalkyl or an unsubstituted monocyclic $C_{3-6}$ cycloalkyl; $R^{3b}$ can be deuterium, halogen, an unsubstituted $C_{1-4}$ alkyl, an unsubstituted $C_{1-4}$ haloalkyl or an unsubstituted monocyclic $C_{3-6}$ cycloalkyl; $R^4$ can be $-C(=O)NR^5R^6$; $R^5$ can be hydrogen or an unsubstituted $C_{14}$ alkyl; and $R^6$ can be hydrogen, an unsubstituted $C_{1-4}$ alkyl, a substituted $C_{1-4}$ alkyl, an unsubstituted monocyclic $C_{3-6}$ cycloalkyl, an unsubstituted bicyclic $C_{5-8}$ cycloalkyl, an unsubstituted monocyclic $C_{3-6}$ cycloalkyl(an unsubstituted $C_{1-4}$ alkyl) or an unsubstituted bicyclic $C_{5-8}$ cycloalkyl(an unsubstituted $C_{1-4}$ alkyl), wherein the substituted $C_{1-4}$ alkyl is substituted by 1 or more deuteriums.

In some embodiments, a compound of Formula (I), or a pharmaceutically acceptable salt thereof, can be where $Y^1$ can be O (oxygen), $CH_2$ or $CHR^{Y1}$, wherein $R^{Y1}$ is deuterium, halogen or an unsubstituted $C_{1-4}$ alkyl; Ring A can be selected from a pyrrole, a thiophene, a pyridine and a phenyl, wherein the pyrrole, the thiophene, the pyridine and the phenyl can be optionally substituted, and when substituted, each can be substituted 1 or more times with a moiety independently selected from deuterium, halogen, an unsubstituted $C_{1-4}$ alkyl and an unsubstituted $C_{1-4}$ haloalkyl; Ring B can be selected from an unsubstituted or a substituted 6-membered monocyclic nitrogen-containing heterocyclyl, an unsubstituted or a substituted 7-membered bicyclic nitrogen-containing heterocyclyl and an unsubstituted or a substituted 8-membered bicyclic nitrogen-containing heterocyclyl; Ring C can be selected from a pyrrole, a thiophene, a thiazole, a pyridine, a pyridazine, a pyrimidine, a pyrazine and a phenyl, wherein the pyrrole, the thiophene, the thiazole, the pyridine, the pyridazine, the pyrimidine, the pyrazine and the phenyl can be optionally substituted, and when substituted, each can be substituted 1 or more times with a moiety independently selected from deuterium, halogen, an unsubstituted $C_{1-4}$ alkyl, an unsubstituted $C_{2-4}$ alkenyl, an unsubstituted monocyclic $C_{3-6}$ cycloalkyl(an unsubstituted $C_{14}$ alkyl) and an unsubstituted $C_{1-4}$ haloalkyl; $R^{1a}$ can be selected from hydrogen, an unsubstituted $C_{2-4}$ alkyl, an unsubstituted $C_{2-4}$ alkenyl, an unsubstituted $C_{1-4}$ haloalkyl, an unsubstituted $C_{14}$ hydroxyalkyl, an unsubstituted monocyclic $C_{3-6}$ cycloalkyl, an unsubstituted bicyclic $C_{5-8}$ cycloalkyl, an unsubstituted monocyclic $C_{3-6}$ cycloalkyl(an unsubstituted $C_{1-4}$ alkyl), a substituted monocyclic $C_{3-6}$ cycloalkyl(an unsubstituted $C_{1-4}$ alkyl), an unsubstituted monocyclic $C_{3-6}$ cycloalkyl(an unsubstituted $C_{1-4}$ alkenyl) and a substituted monocyclic $C_{3-6}$ cycloalkyl(an unsubstituted $C_{1-4}$ alkenyl), wherein the substituted monocyclic $C_{3-6}$ cycloalkyl(an unsubstituted $C_{1-4}$ alkyl) can be substituted by 1 or more deuteriums; $R^{1b}$ can be hydrogen, an unsubstituted $C_{14}$ alkyl or an unsubstituted $C_{1-4}$ haloalkyl; or $R^{1a}$ and $R^{1b}$ can be taken together along with the carbon to which $R^{1a}$ and $R^{1b}$ are attached to form an unsubstituted or a substituted monocyclic 3-4-membered cycloalkyl or an unsubstituted or a substituted monocyclic 4-5 membered heterocyclyl, wherein the substituted monocyclic 3-4-membered cycloalkyl and the substituted monocyclic 4-5 membered heterocyclyl can be each substituted with one or more moieties independently selected from halogen, an unsubstituted $C_{1-3}$ alkyl and an unsubstituted $C_{1-3}$ haloalkyl; provided that when $R^{1a}$ is hydrogen, then $R^{1b}$ can be hydrogen, an unsubstituted $C_{2-4}$ alkyl or an unsubstituted $C_{1-4}$ haloalkyl; $R^2$ and $R^3$ can be independently hydrogen, deuterium or an unsubstituted $C_{1-4}$ alkyl; or $R^2$ and $R^3$ can be taken together along with the carbon to which $R^2$ and $R^3$ are attached to form an unsubstituted or a substituted monocyclic $C_{3-6}$ cycloalkyl; m can be 0 or 1; n can be 0, 1 or 2; $R^{3a}$ can be deuterium, halogen, an unsubstituted $C_{1-4}$ alkyl, an unsubstituted $C_{1-4}$ haloalkyl or an unsubstituted monocyclic $C_{3-6}$ cycloalkyl; $R^{3b}$ can be deuterium, halogen, an unsubstituted $C_{1-4}$ alkyl, an unsubstituted $C_{1-4}$ haloalkyl or an unsubstituted monocyclic $C_{3-6}$ cycloalkyl; $R^4$ can be $-C(=O)NR^5R^6$; $R^5$ can be hydrogen or an unsubstituted $C_{14}$ alkyl; and $R^6$ can be hydrogen, an unsubstituted $C_{1-4}$ alkyl, a substituted $C_{1-4}$ alkyl, an unsubstituted monocyclic $C_{3-6}$ cycloalkyl, an unsubstituted bicyclic $C_{5-8}$ cycloalkyl, an unsubstituted monocyclic $C_{3-6}$ cycloalkyl(an unsubstituted $C_{1-4}$ alkyl) or an unsubstituted bicyclic $C_{5-8}$ cycloalkyl(an unsubstituted $C_{1-4}$ alkyl), wherein the substituted $C_{1-4}$ alkyl is substituted by 1 or more deuteriums.

Examples of compounds of Formula (I), include the following:
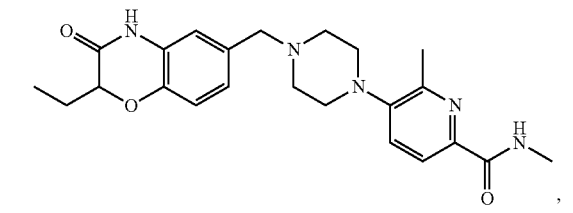
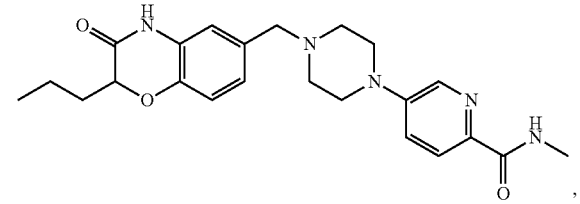
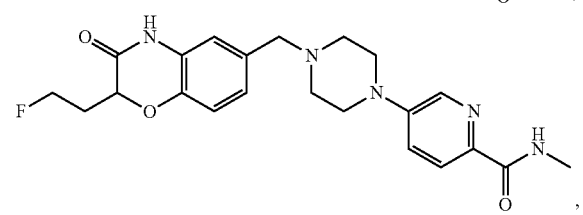
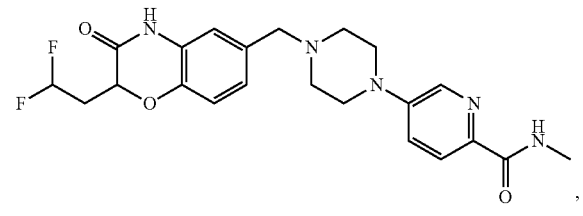
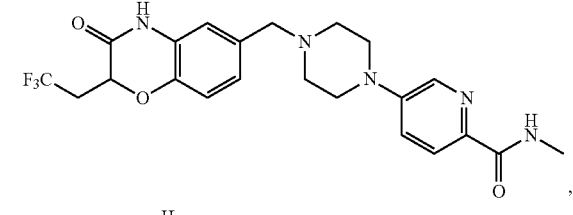
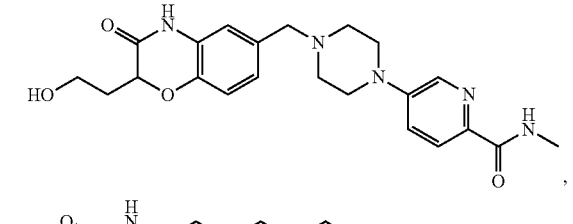
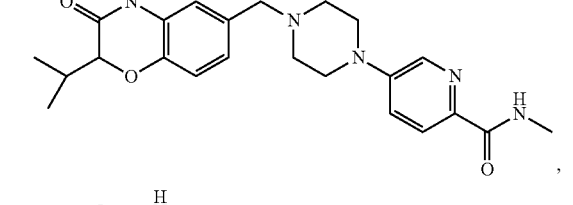
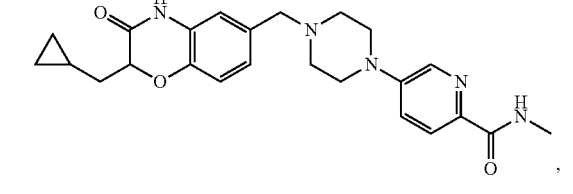
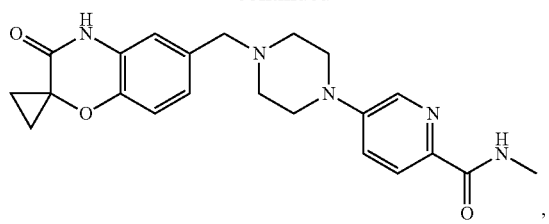
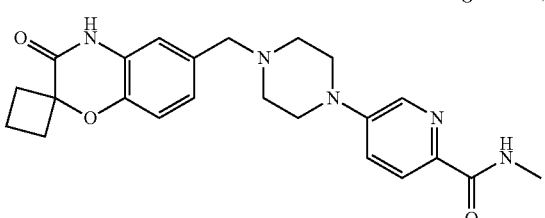
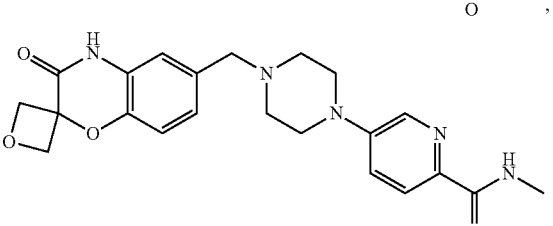
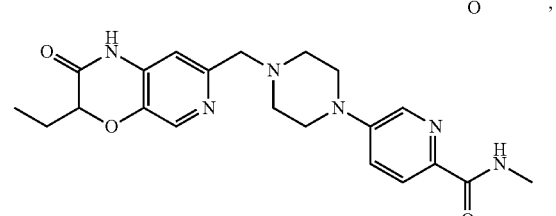
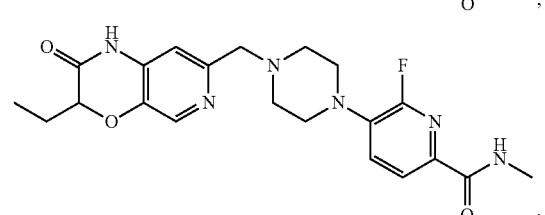
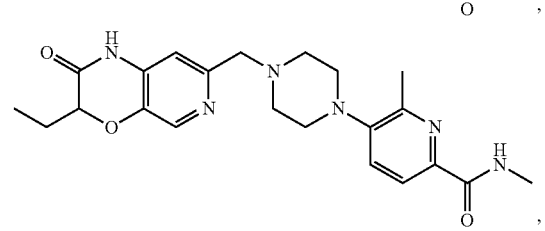
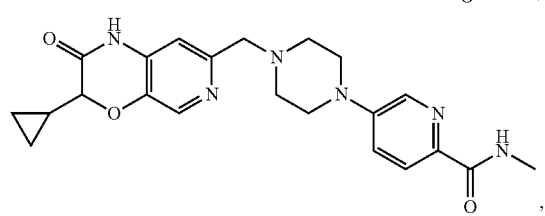
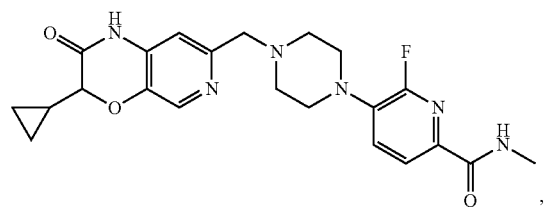

29
-continued
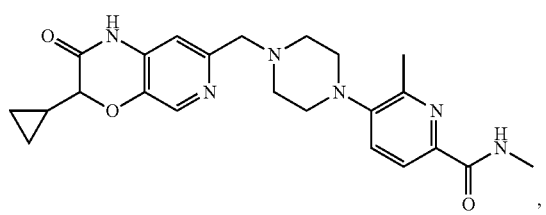,
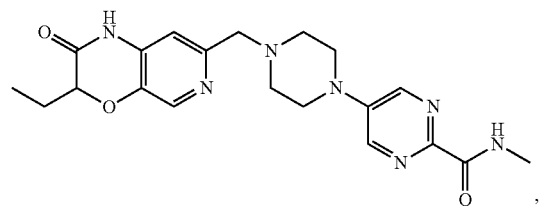,
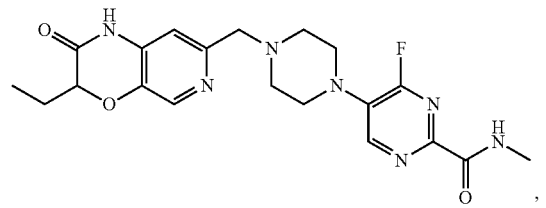,
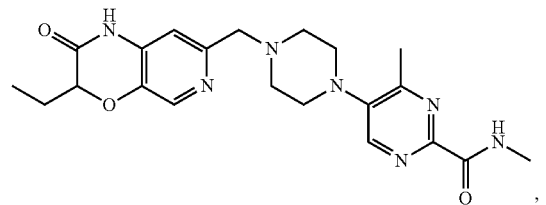,
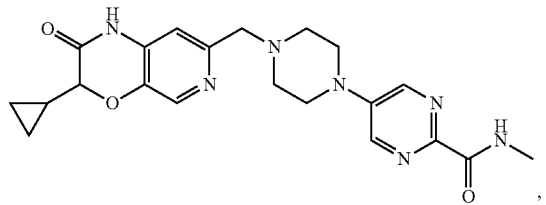,
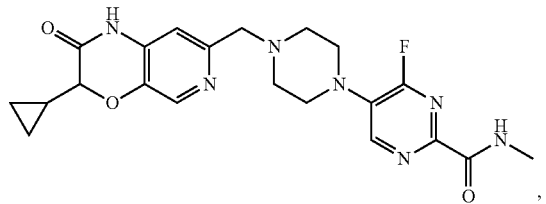,
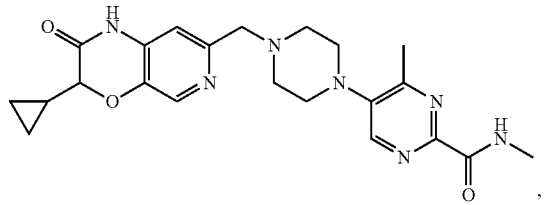,
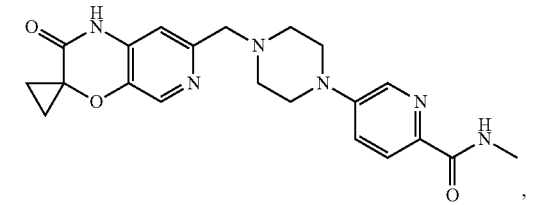,
30
-continued
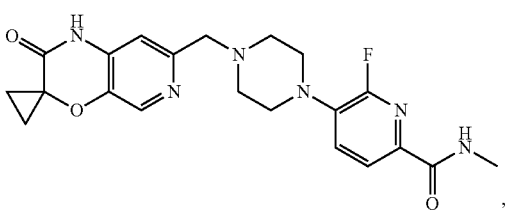,
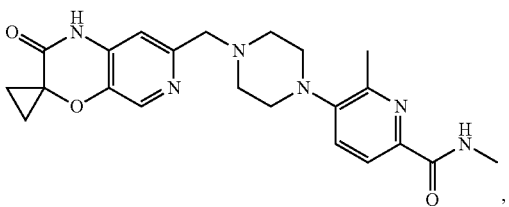,
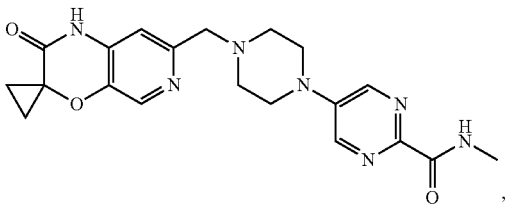,
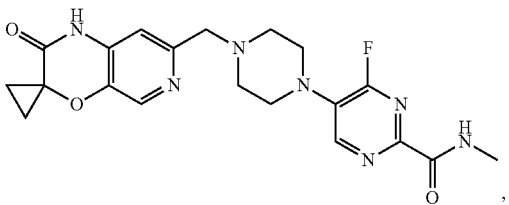,
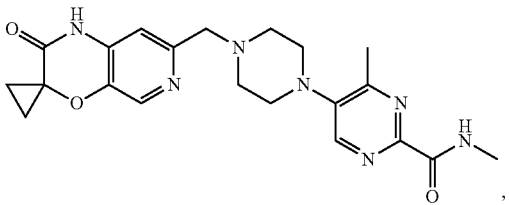,
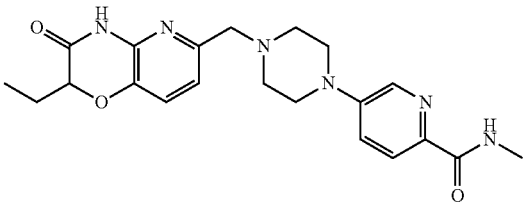,
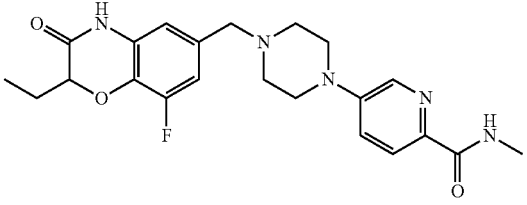,
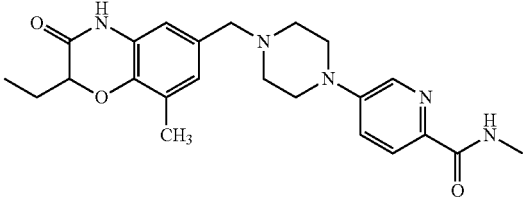, -continued

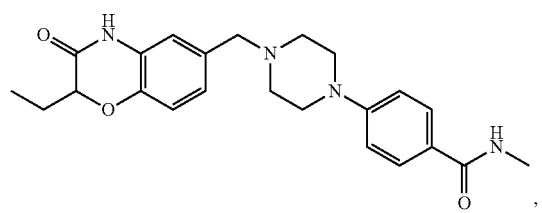
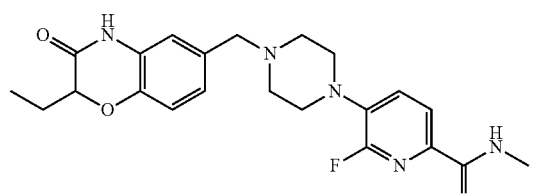
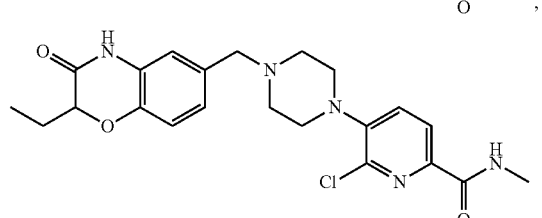
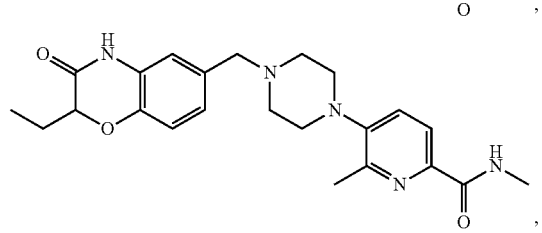
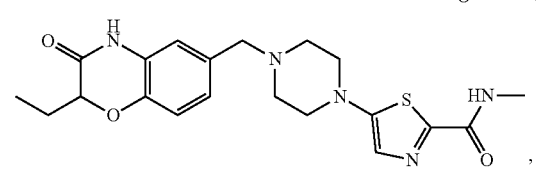
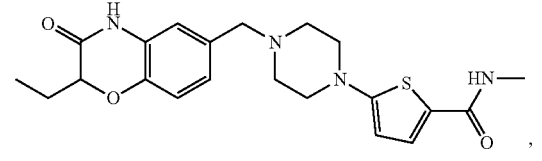
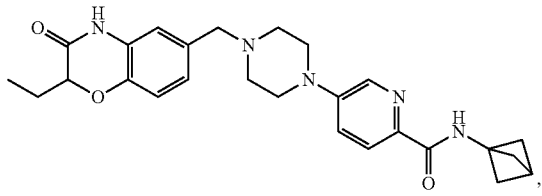
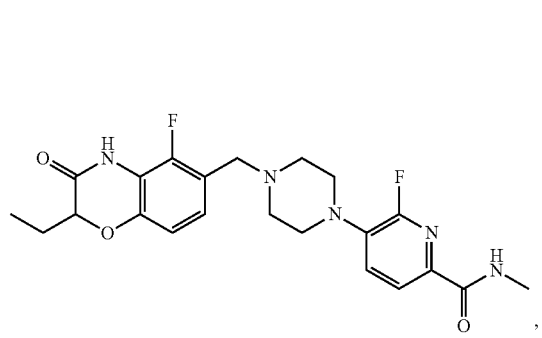
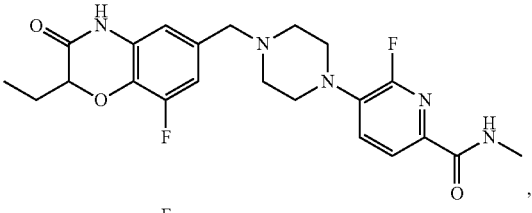
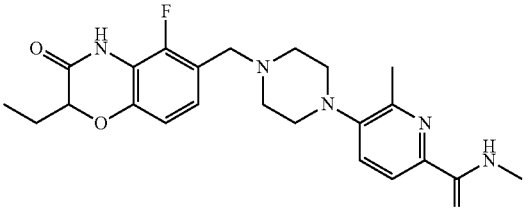
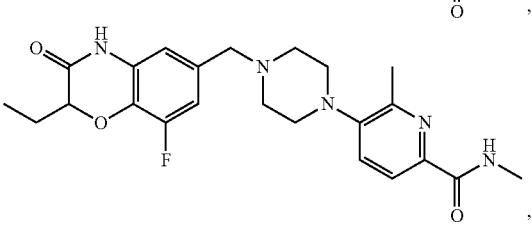
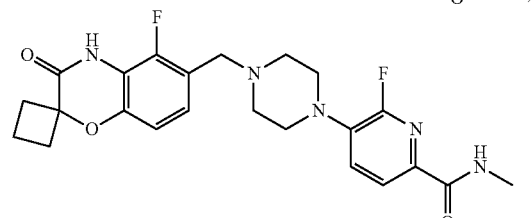
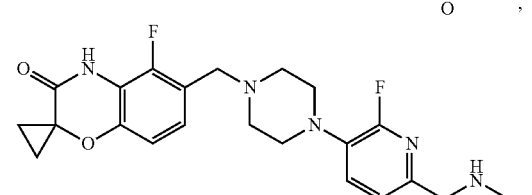
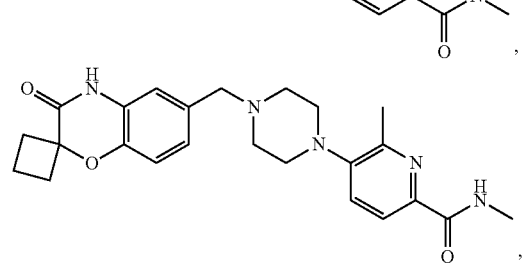
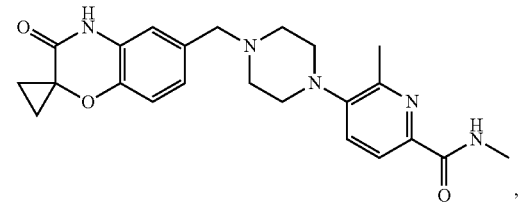
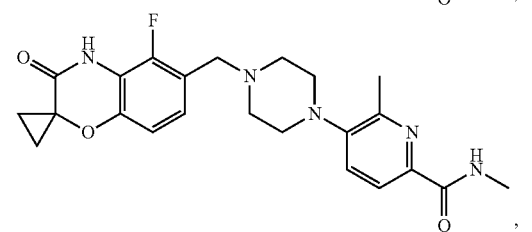

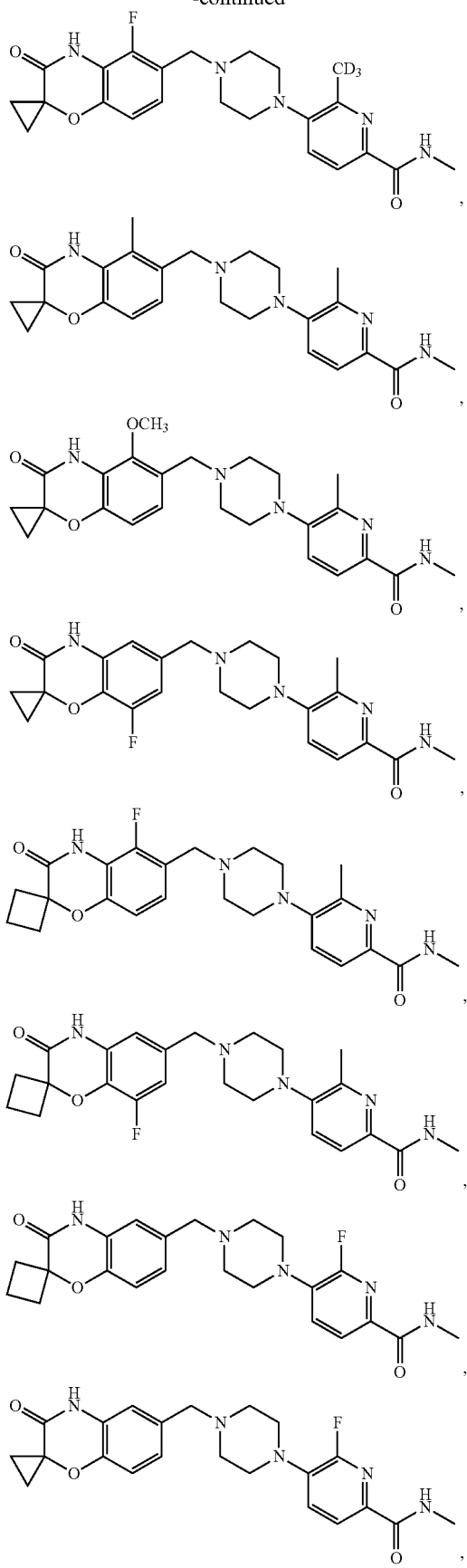
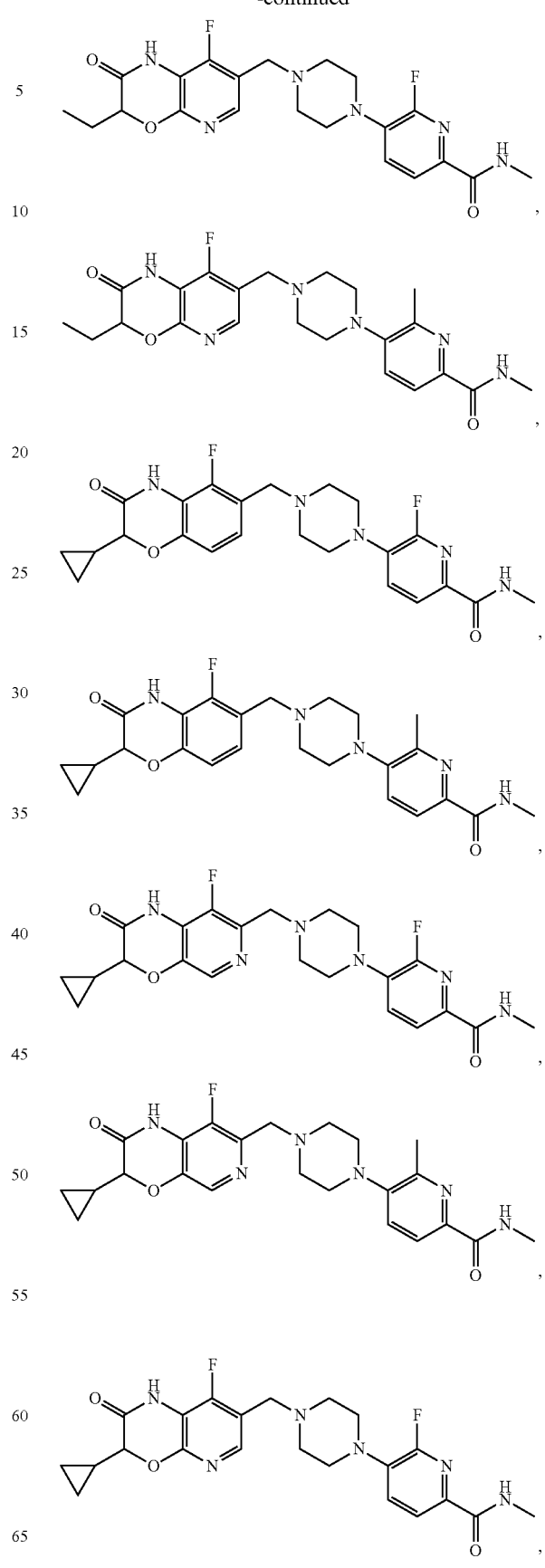

-continued
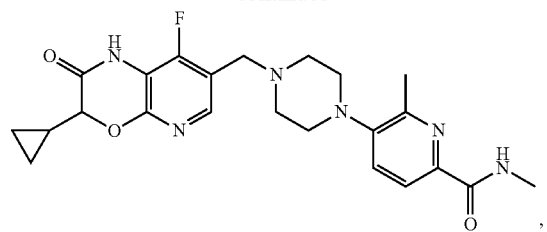
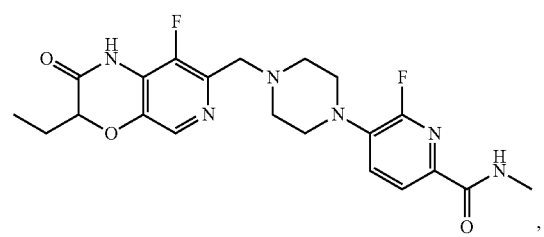
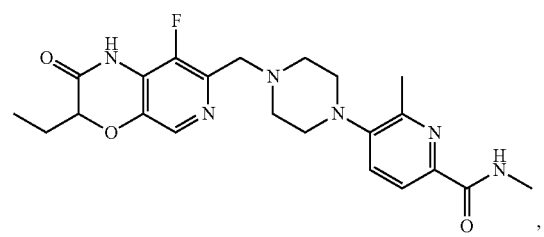
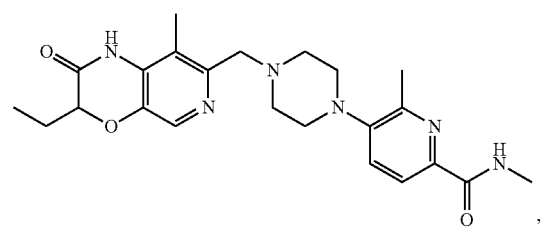
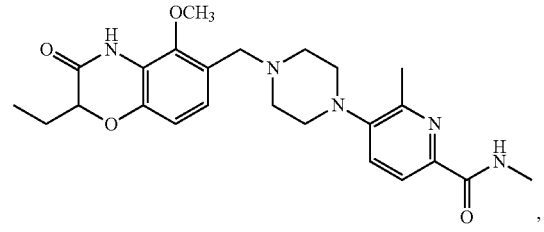
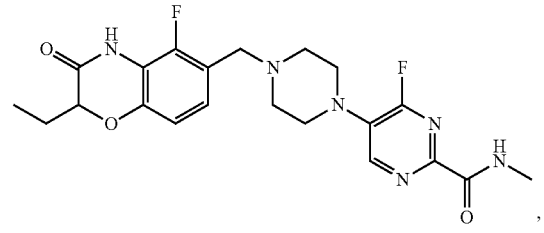
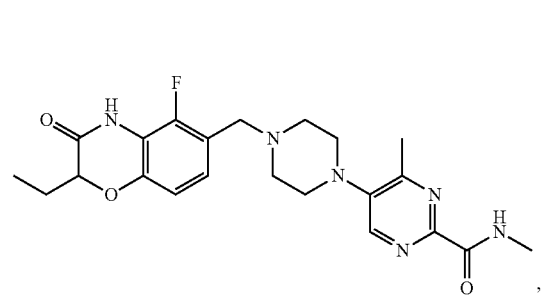
-continued
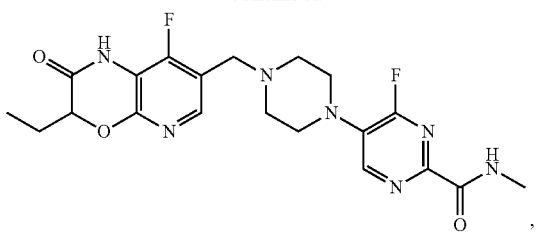
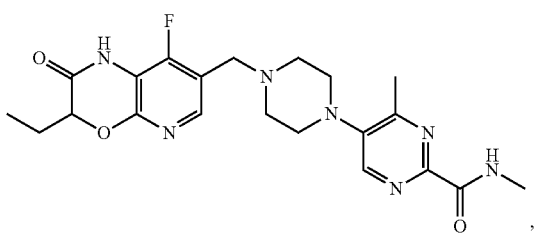
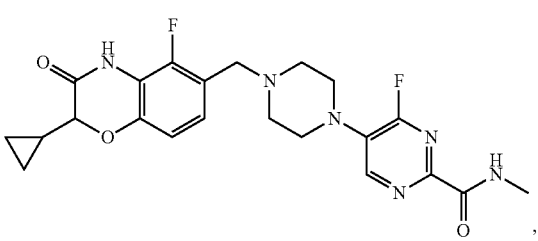
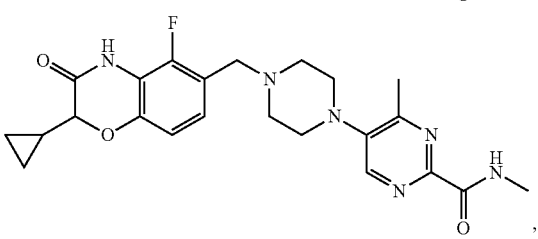
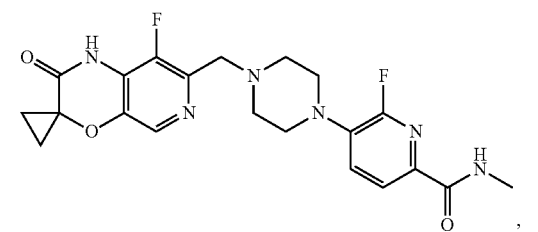
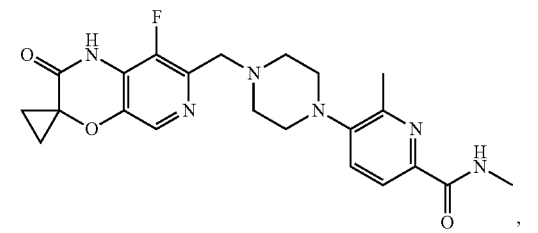
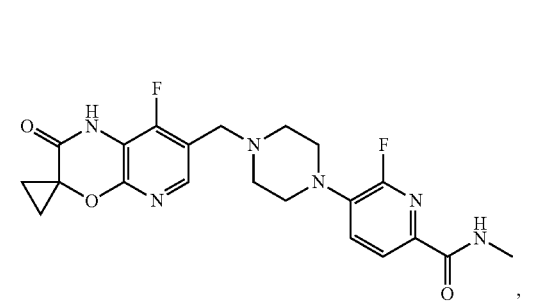

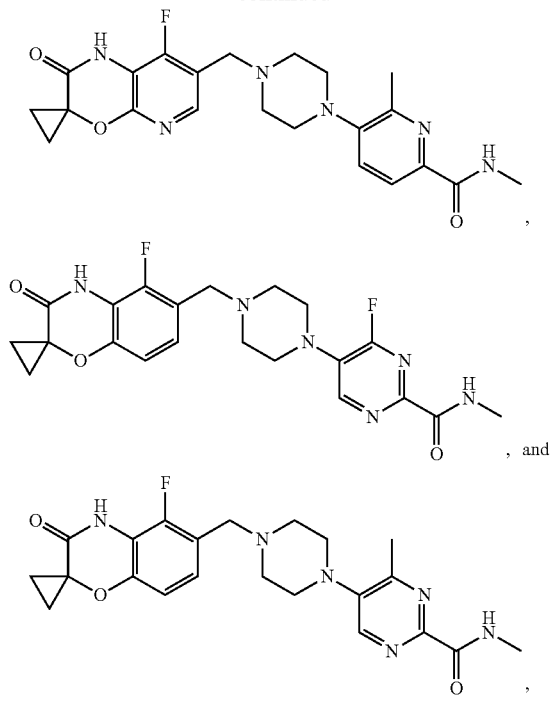
or a pharmaceutically acceptable salt of any of the foregoing.
Further examples of compounds of Formula (I), include the following:
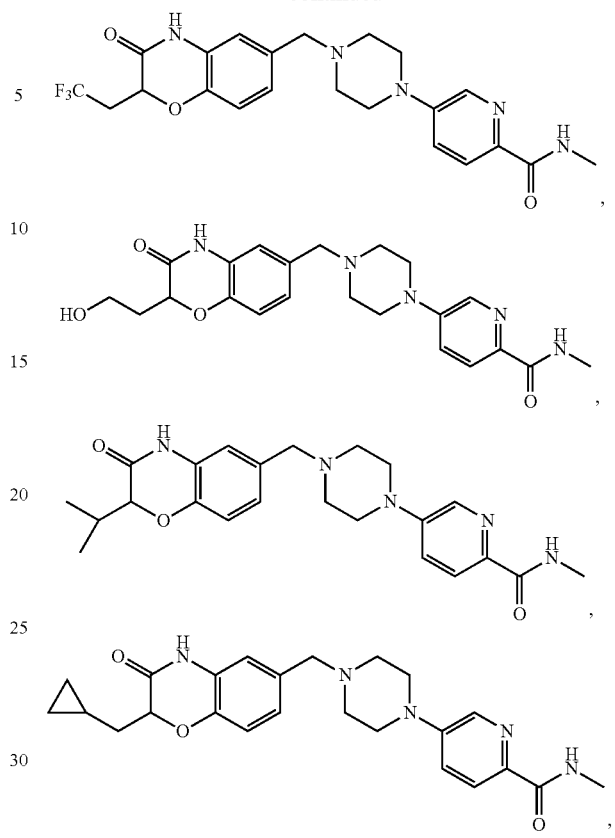
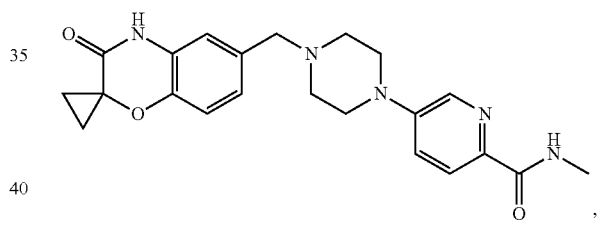
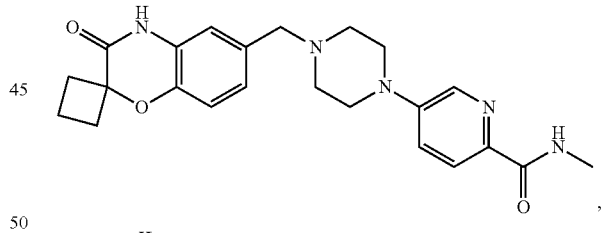
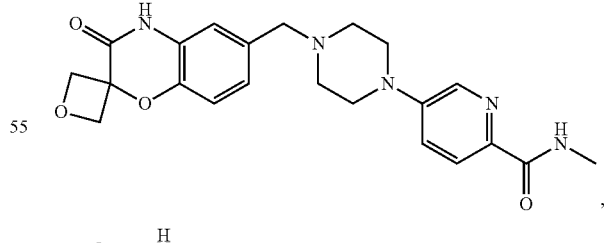
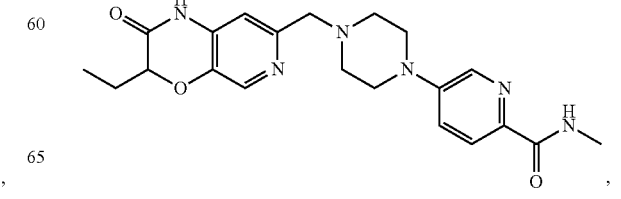

41
-continued
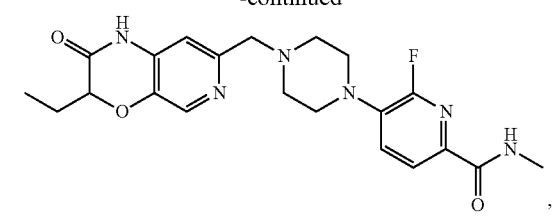
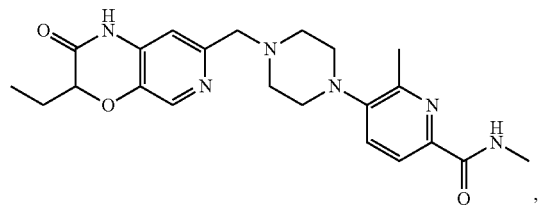
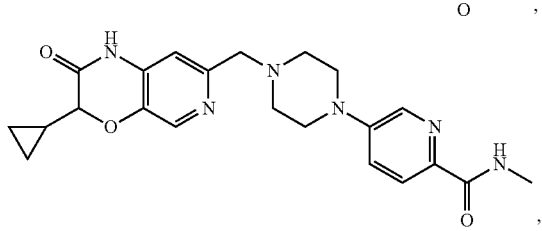
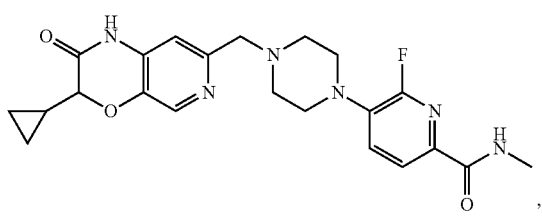
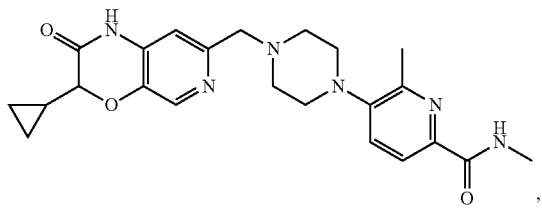
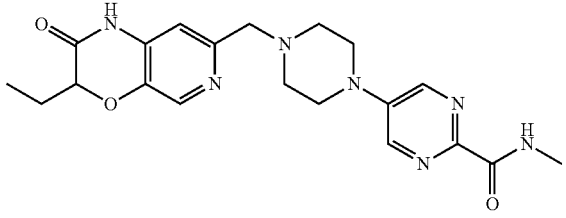
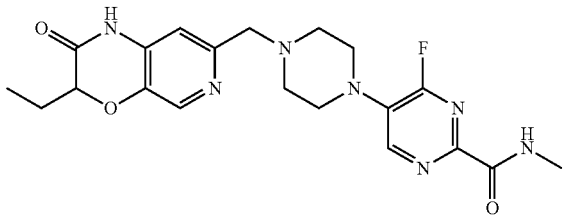
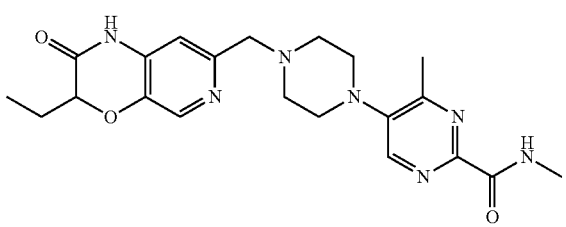
42
-continued
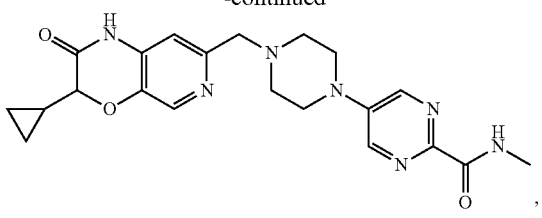
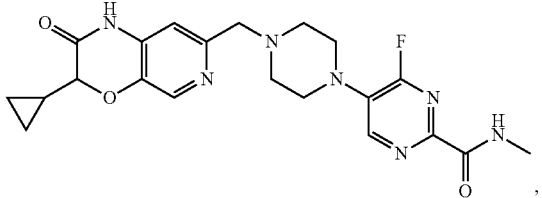
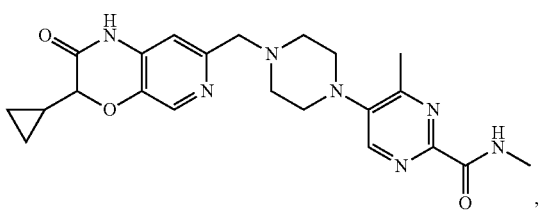
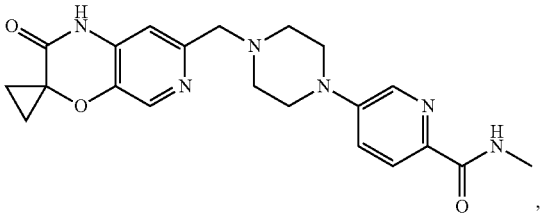
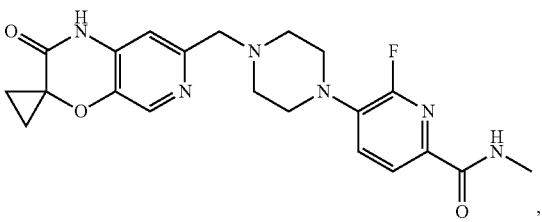
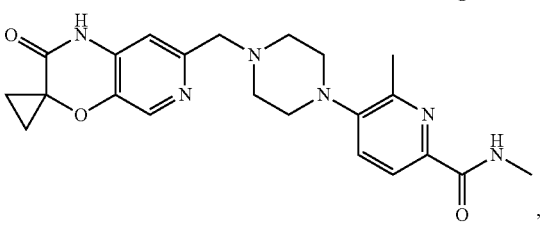
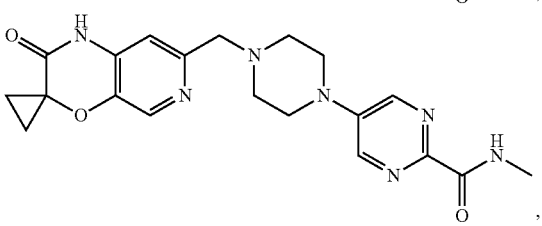
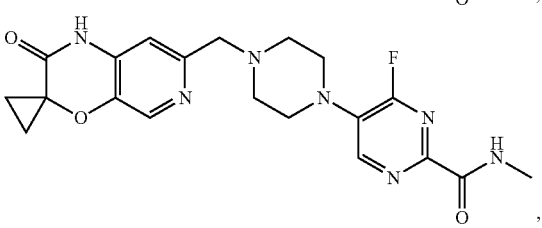

-continued

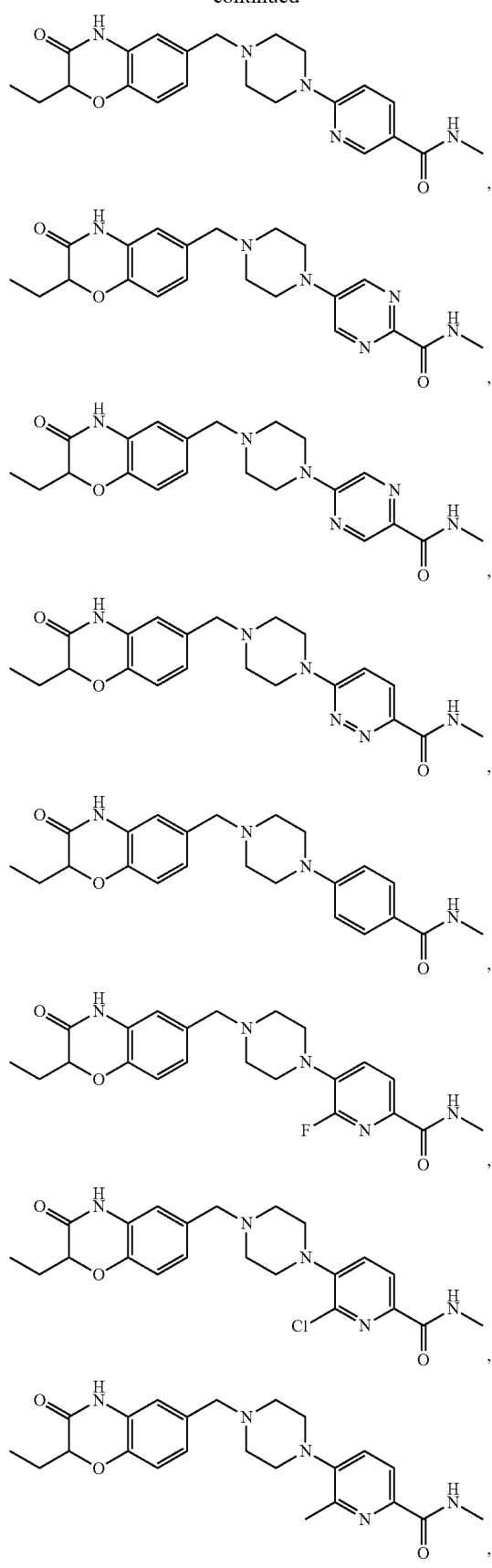
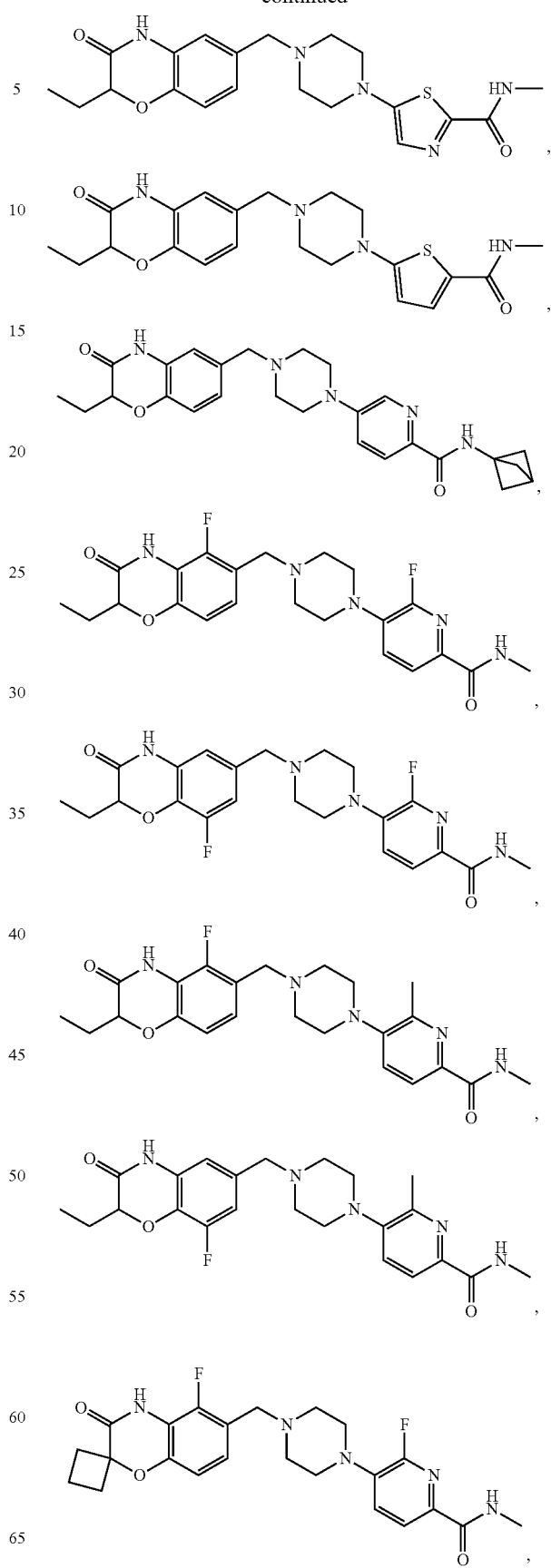

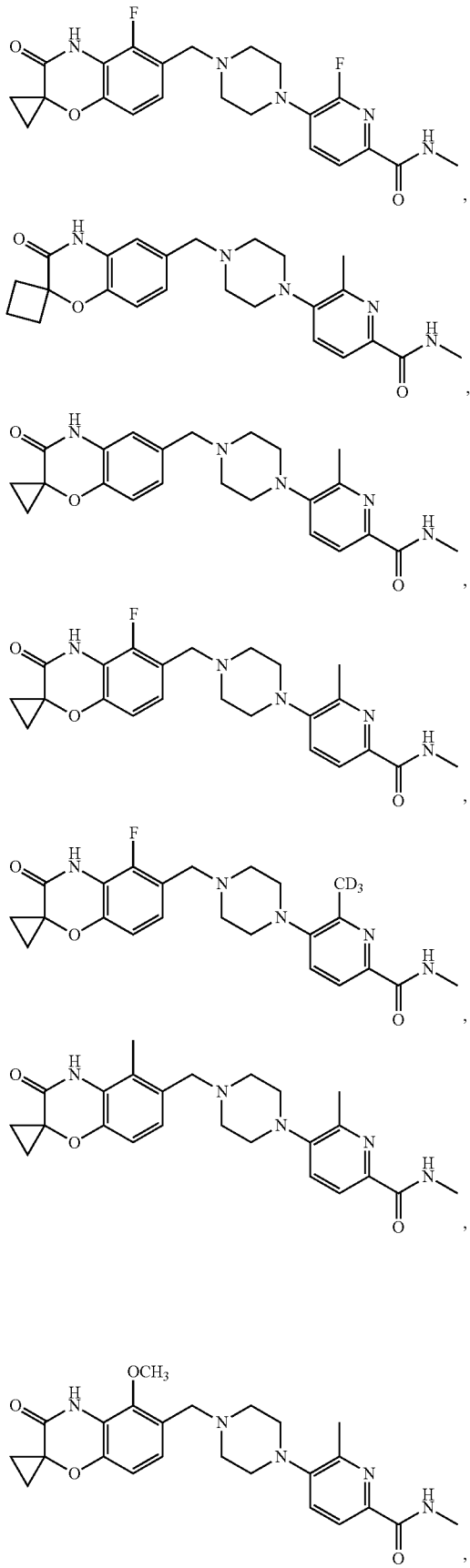
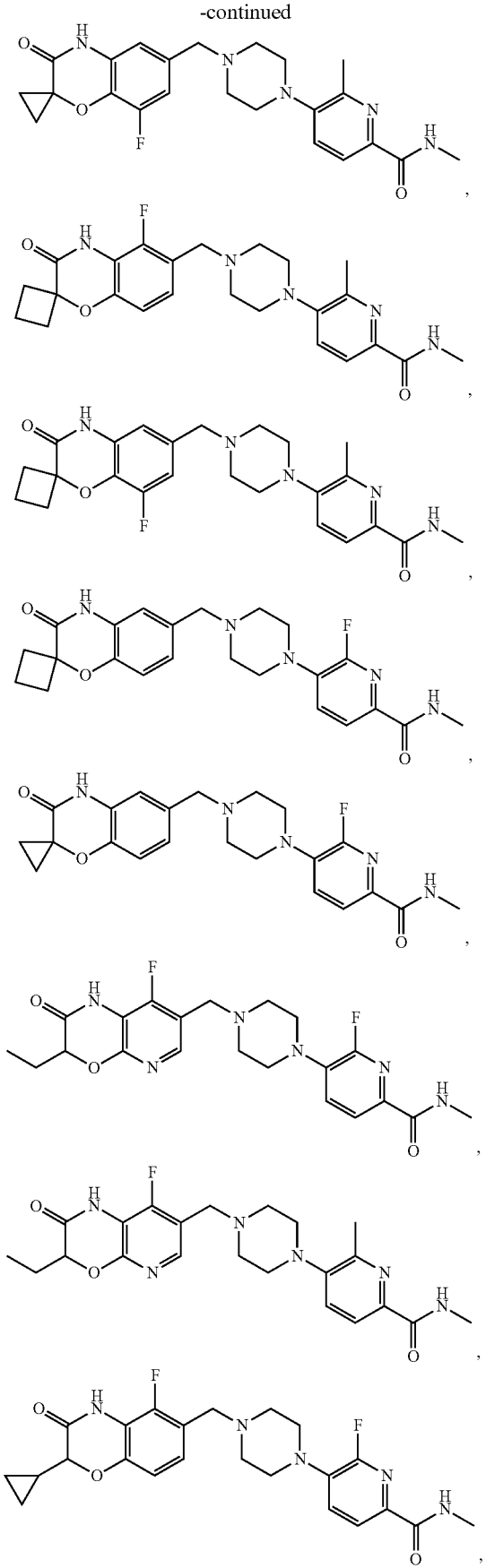

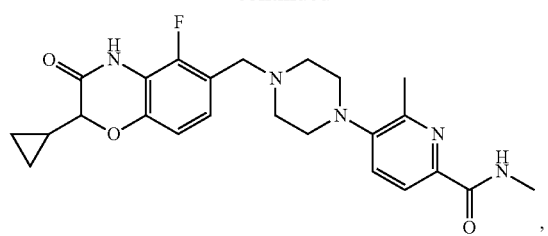
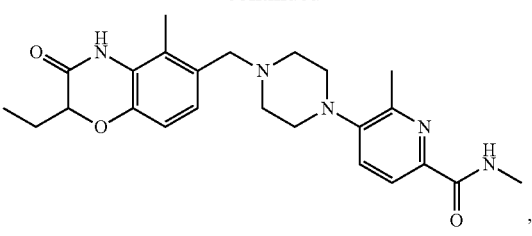
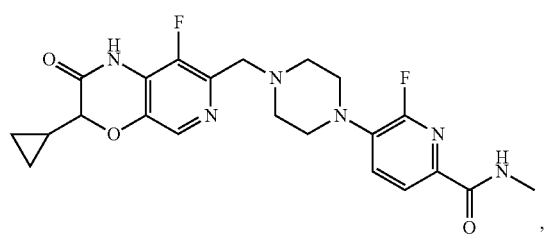
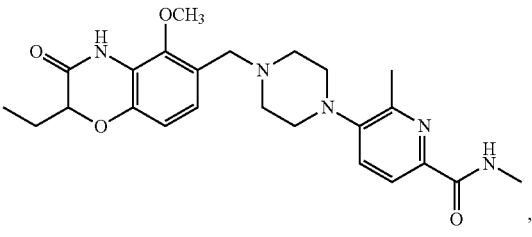
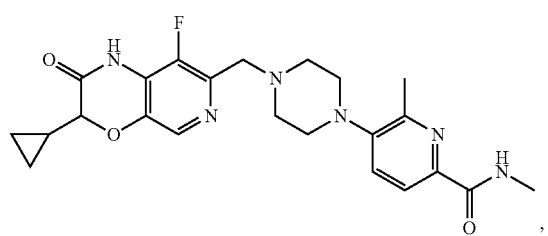
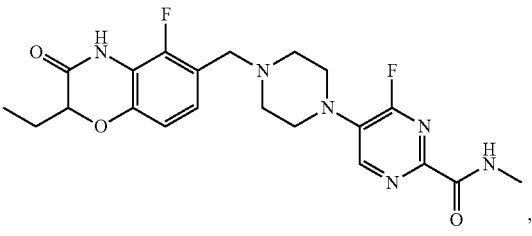
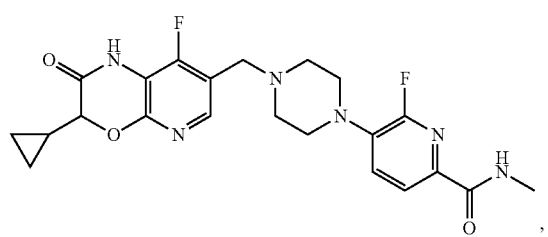
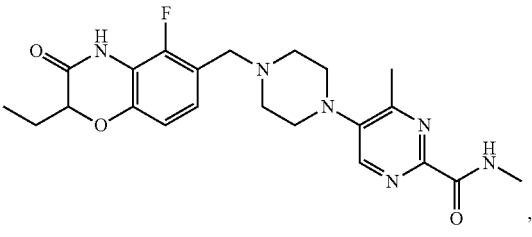
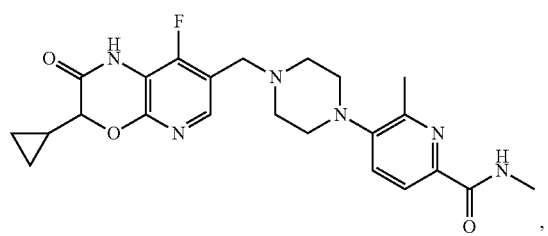
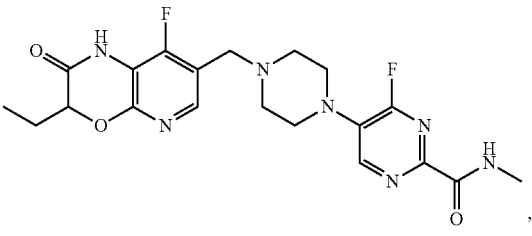
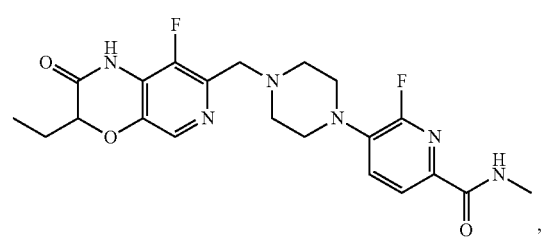
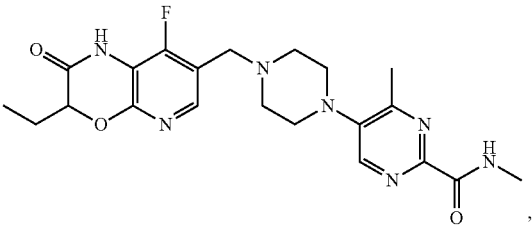
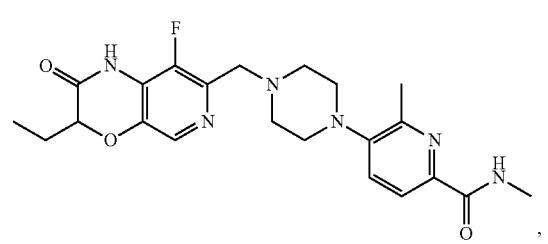
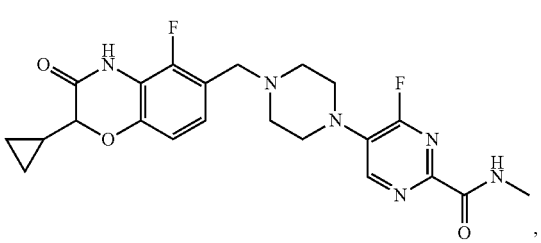

-continued
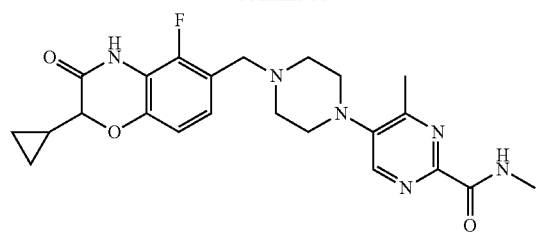
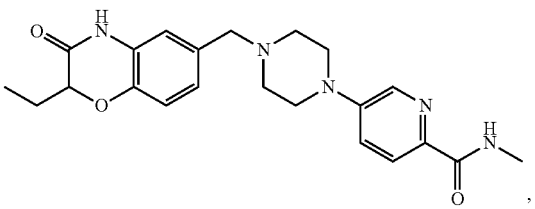
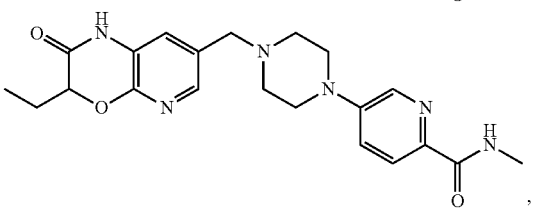
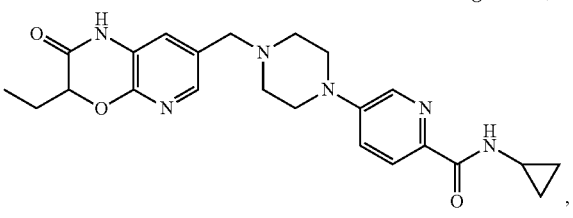
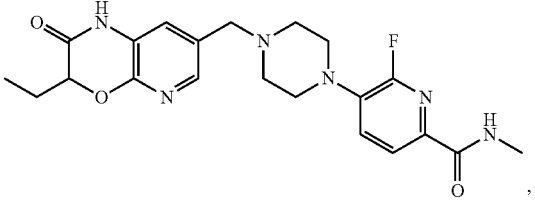
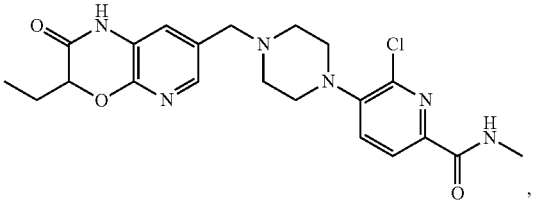
or a pharmaceutically acceptable salt of any of the foregoing.
In some embodiments, a compound of Formula (I) or a pharmaceutically acceptable salt thereof, cannot be selected from:
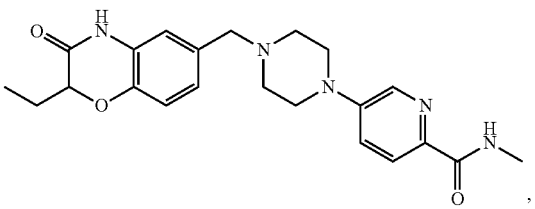
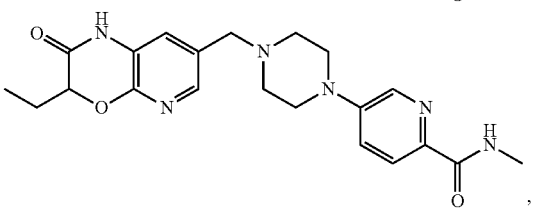
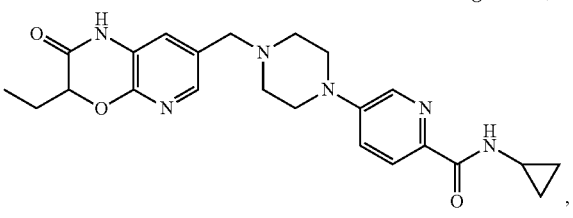
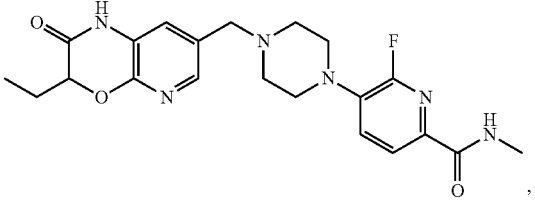
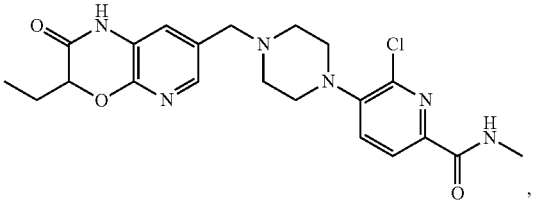
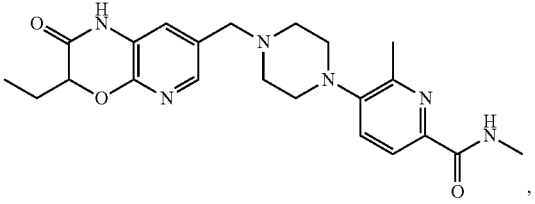
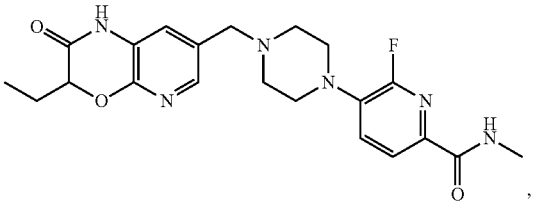
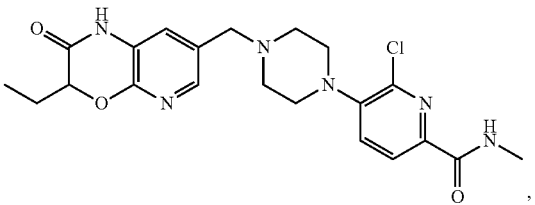

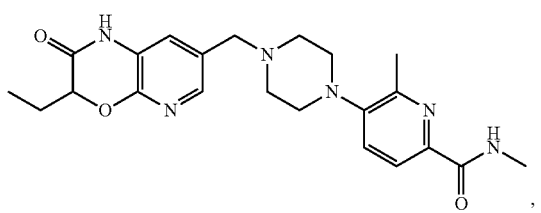

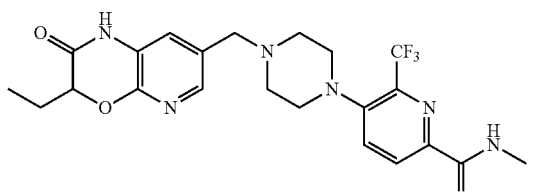

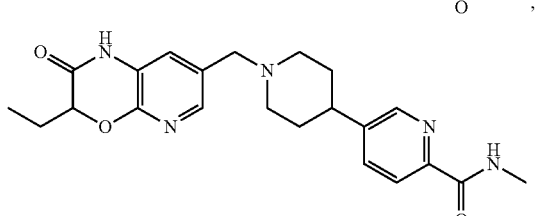

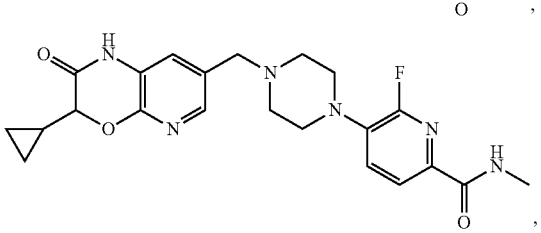

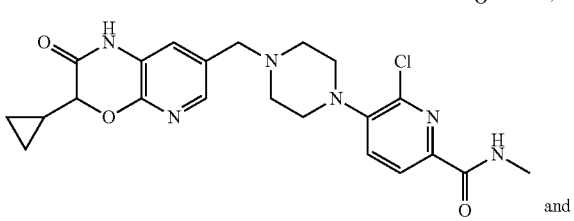

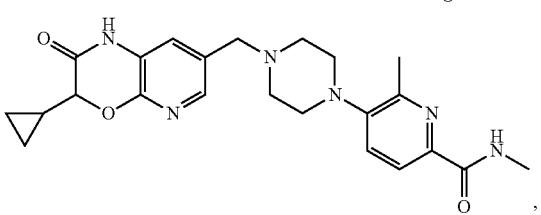

or a pharmaceutically acceptable salt of any of the foregoing. In some embodiments, a compound of Formula (I) or a pharmaceutically acceptable salt thereof, cannot be provided in WO 2022/222921, WO 2022/223025 and/or WO 2010/111626. In some embodiments, Ring A cannot be phenyl. In some embodiments, Ring A cannot be

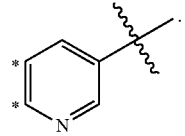 [SMILES: *c1cccnc1]

In some embodiments, Ring A cannot be phenyl. In some embodiments, Ring C cannot be

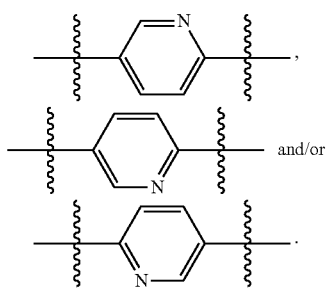

In some embodiments, Ring C cannot be

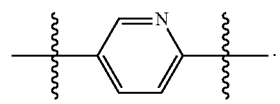 [SMILES: *c1ccc(*)nc1]

In some embodiments, Ring A and Ring C cannot be each unsubstituted. In some embodiments, Ring A cannot be unsubstituted and Ring C cannot be substituted (for example, mono-substituted). In other embodiments, Ring A cannot be substituted (for example, mono-substituted) and Ring C cannot be unsubstituted.

Synthesis

Compounds of Formula (I) along with those described herein may be prepared in various ways. General synthetic routes for preparing compounds of Formula (I) are shown and described herein along with some examples of starting materials used to synthesize compounds described herein. Additionally, for the purpose of the general synthetic routes, the structures depicted are appropriately protected, as known by one skilled in the art and the generic structures are meant to include these protecting groups. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Scheme 1

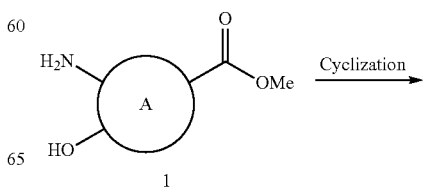

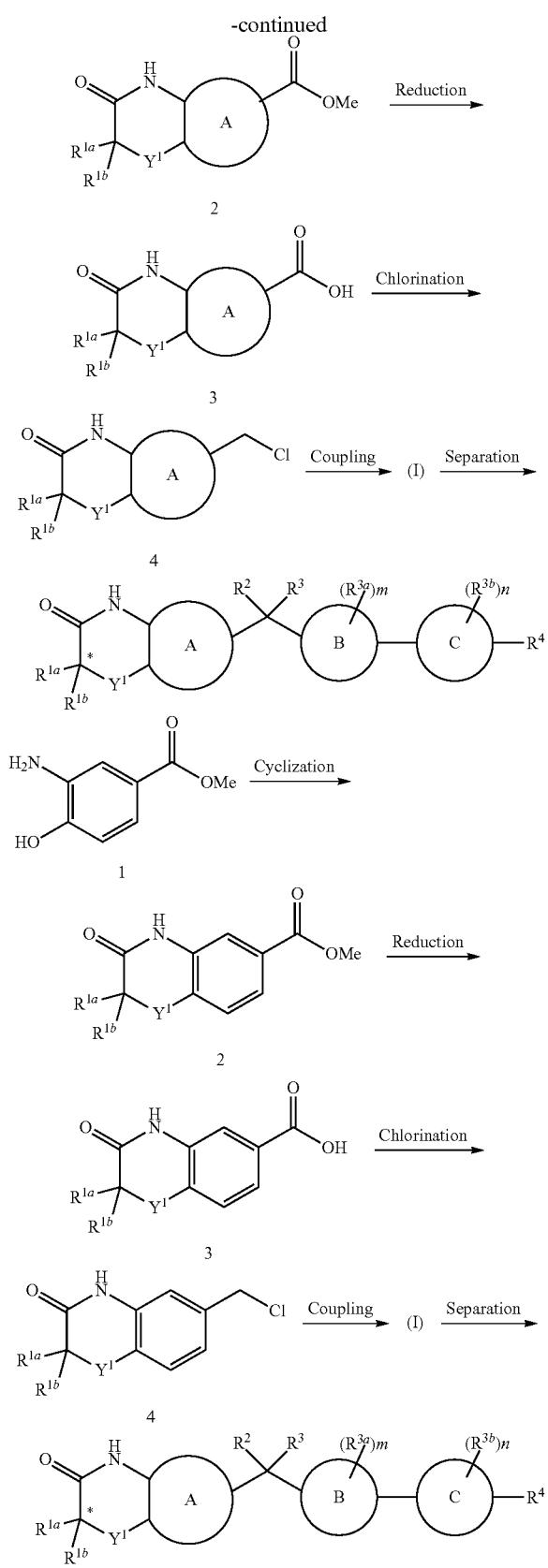

Scheme 1 provides an exemplary method for preparing a compound of Formula (I), including pharmaceutically acceptable salts thereof. In Scheme 1, the separation can be accomplished by methods known to those skilled in the art, such as supercritical fluid chromatography, to provide compounds of Formula (I) where the compound indicated with an asterisk is in the (R)- or (S)-configuration.

Pharmaceutical Compositions

Some embodiments described herein relate to a pharmaceutical composition, which can include an effective amount of a compound described herein (e.g., a compound, or a pharmaceutically acceptable salt thereof, as described herein) and a pharmaceutically acceptable carrier, excipient or combination thereof. A pharmaceutical composition described herein is suitable for human and/or veterinary applications.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

Proper formulation is dependent upon the route of administration chosen. Techniques for formulation and administration of the compounds described herein are known to those skilled in the art. Multiple techniques of administering a compound exist in the art including, but not limited to, oral, rectal, topical, aerosol, injection, inhalation and parenteral delivery, including intramuscular, subcutaneous, intravenous, intramedullary injections, intrathecal, direct intraventricular, intraperitoneal, intranasal and intraocular injections. Pharmaceutical compositions will generally be tailored to the specific intended route of administration.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes may be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

Methods of Use

Some embodiments described herein relate to a method for treating a cancer described herein that can include administering an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for treating a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for treating a cancer described herein.

Some embodiments described herein relate to a method for inhibiting growth of a malignant growth or a tumor that can include contacting the growth or the tumor with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof), wherein the malignant growth or tumor is due to a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for inhibiting growth of a malignant growth or a tumor, wherein the malignant growth or tumor is due to a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for inhibiting growth of a malignant growth or a tumor, wherein the malignant growth or tumor is due to a cancer described herein.

Some embodiments described herein relate to a method for treating a cancer described herein that can include contacting a malignant growth or a tumor with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for treating a cancer that can include contacting a malignant growth or a tumor, wherein the malignant growth or tumor is due to a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for treating a cancer that can include contacting a malignant growth or a tumor, wherein the malignant growth or tumor is due to a cancer described herein.

Some embodiments described herein relate to a method for inhibiting the activity of PARP1 that can include providing an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a cancer cell from a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for inhibiting the activity of PARP1. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for inhibiting the activity of PARP1. Some embodiments described herein relate to a method for inhibiting the activity of PARP1 that can include providing an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a cancer cell from a cancer described herein. Other embodiments described herein relate to a method for inhibiting the activity of PARP1 that can include contacting a cancer cell from a cancer described herein with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof), and thereby inhibiting the activity of PARP1.

Some embodiments described herein relate to a method for treating a cancer described herein that can include inhibiting the activity of PARP1 using an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof). Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for treating a cancer described herein by inhibiting the activity of PARP1. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for treating a cancer described herein by inhibiting the activity of PARP1. Some embodiments described herein relate to a method for treating a cancer described herein that can include contacting a cancer cell with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof), wherein the compound inhibits the activity of PARP1.

Some embodiments disclosed herein relate to a method for inhibiting the activity of PARP1 that can include providing an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a subject having a cancer described herein or a cancer cell from a cancer described herein. Other embodiments disclosed herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for inhibiting the activity of PARP1. Still other embodiments disclosed herein relate to a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for inhibiting the activity of PARP1.

Examples of suitable cancers include, but are not limited to: a lung cancer, a pancreatic cancer, a colon cancer (e.g., colorectal cancer), a myeloid leukemia (e.g., AML, CML, and CMML), a thyroid cancer, a myelodysplastic syndrome (MDS), a bladder carcinoma, an epidermal carcinoma, a melanoma, a breast cancer, a prostate cancer, a head and neck cancers (e.g., squamous cell cancer of the head and neck), an ovarian cancer, a brain cancer (e.g., gliomas, such as glioma blastoma multiforme), a cancer of mesenchymal origin (e.g., fibrosarcomas and rhabdomyosarcomas), a sarcoma, a tetracarcinoma, a nuroblastoma, a kidney carcinoma, a hepatoma, non-Hodgkin's lymphoma, multiple myeloma or an anaplastic thyroid carcinoma.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, camels, non-human primates, such as monkeys, chimpanzees, and apes, and, in particular, humans. In some embodiments, the subject can be human, for example a human subject that is 18 years old or older.

The term "effective amount" is used to indicate an amount of an active compound, or pharmaceutical agent, which elicits the biological or medicinal response indicated. For example, an effective amount of compound can be the amount needed to alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

EXAMPLES

Additional embodiments are disclosed in further detail in the following examples, which are not in any way intended to limit the scope of the claims.

| Abbreviation | |
|---|---|
| ACN | Acetonitrile |
| h | hour |
| EA | Ethyl acetate |
| PE | Petroleum ether |
| Rt | Retention Time |
| SFC | Supercritical Fluid Chromatography |
| THF | Tetrahydrofuran |

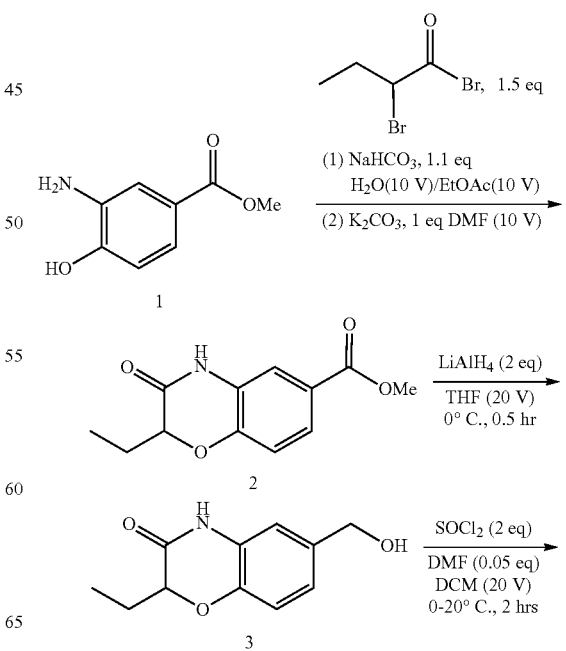

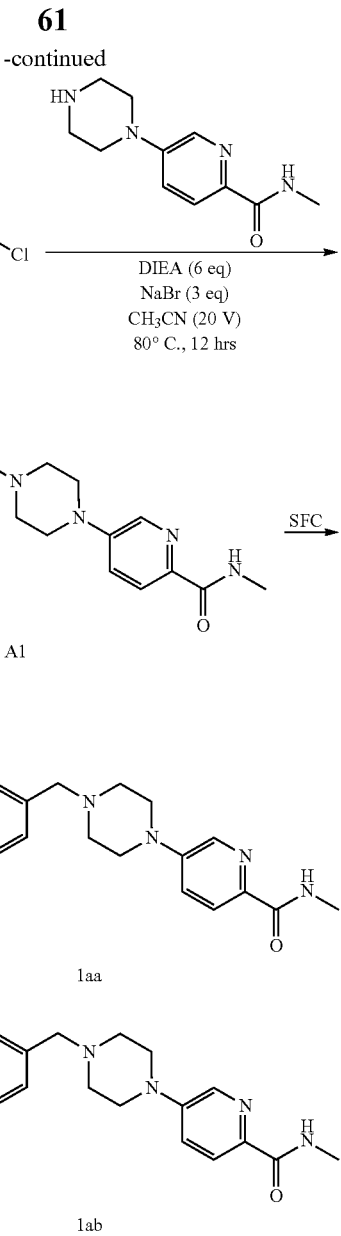

To a solution of 1 (1 g, 5.98 mmol) and NaHCO$_3$ (552.80 mg, 6.58 mmol) in EA (10 mL) and H$_2$O (10 mL) was added 2-bromobutanoyl bromide (2.06 g, 8.97 mmol). The mixture was stirred under at 25° C. for 16.5 h. The mixture was extracted with EA (3×30 mL). The combined organic phase was washed with brine (50 mL), dried over Na$_2$SO$_4$ and concentrated to give a residue. The residue was dissolved in N,N-dimethyl formamide (10 mL) and K$_2$CO$_3$ (826.78 mg, 5.98 mmol) was added to the mixture at 25° C. The mixture was stirred under at 25° C. for 16 h. The solution was poured into the ice water (30 mL). The resulting solid was collected by filtration and the cake was dried under high vacuum to give the crude product. The crude product was triturated with PE:EA (3:1) at 25° C. for 30 min and filtered. Compound 2 (1.01 g, 71.77% yield) was obtained as a white solid.

To a solution of 2 (1 g, 4.25 mmol) in THF (20 mL) was added LiAlH$_4$ (322.69 mg, 8.50 mmol) at 0° C. The mixture was stirred at 0° C. for 0.5 h. The mixture was cooled to 0° C. H$_2$O (0.3 mL) was added dropwise to the mixture at 0° C. followed by 15% NaOH (0.3 mL) and H$_2$O (0.9 mL). The mixture was stirred for 20 mins and then filtered. The filtrate was dried over Na$_2$SO$_4$ and concentrated to give the crude product. The crude product was triturated with EA (20 mL) at 20° C. for 30 mins and then filtered. Compound 3 (440 mg, 47.45% yield) was obtained as a white solid.

To a solution of 3 (396.22 mg, 1.91 mmol) in dichloromethane (8 mL) and N,N-dimethyl formamide (0.01 mL) was added SOCl$_2$ (454.95 mg, 3.82 mmol, 277.41 uL) at 20° C. The mixture was stirred at 20° C. for 2 h. The mixture was filtered. The filter cake was dried in high vacuum to give a residue and that stirred in EA (3 mL) for 1 h to form a slurry and then filtered. Compound 4 (420 mg, 97.34% yield) was obtained as a yellow solid.

To a solution of 4 (350 mg, 1.55 mmol) and N-methyl-5-piperazin-1-yl-pyridine-2-carboxamide (341.62 mg, 1.55 mmol) in acetonitrile (8 mL) was added N.N-diisopropyl-ethylamine (1.62 mL) and NaBr (478.74 mg, 4.65 mmol) at 20° C. The mixture was stirred at 80° C. for 12 h. The mixture was filtered, and the cake was dried under reduced pressure to give a residue (630 mg, 99.20% yield). The residue (100 mg) was purified by prep-HPLC to give pure 1A (19.4 mg, 19.4% yield) as a white solid. The residue (100 mg) was separated by SFC to give two enantiomers: 1aa (13.3 mg, 26% yield) and 1ab (16.2 mg, 32% yield) were obtained as white solids. The absolute configurations of 1aa and 1ab have not yet been determined. The relative configurations are shown above, and the configurations were assigned arbitrarily.

LC/MS: The gradient was 5% B in 0.40 min and 5-95% B at 0.40-3.00 min, hold on 95% B for 1.00 min, and then 95-5% B in 0.01 min, the flow rate was 1.0 mL/min. Mobile phase A was 0.04% trifluoroacetic acid in water, mobile phase B was 0.02% trifluoroacetic acid in acetonitrile. The column used for chromatography was a Luna C18 50*2.0 mm column (5 um particles). Detection methods are diode array (DAD) and evaporative light scattering (ELSD) detection. MS mode was positive electrospray ionization. MS range was 100-1000.

SFC: column: Phenomenex Luna C18 75*30 mm*3 um; mobile phase: [water(FA)-ACN]; B %: 15%-45%,&min.

Compound 1A: $^1$H NMR: (400 MHz, DMSO-d$_6$) δ 0.99 (br d, J=4.88 Hz, 3H) 1.66-1.91 (m, 2H) 2.54 (br d, J=3.75 Hz, 4H) 2.68-2.89 (m, 3H) 3.32-3.39 (m, 4H) 3.43 (br d, J=7.00 Hz, 2H) 4.41-4.59 (m, 1H) 6.75-7.07 (m, 3H) 7.25-7.54 (m, 1H) 7.64-7.99 (m, 1H) 8.09-8.51 (m, 3H) 10.46-10.81 (m, 1H). LCMS (ESI+):410.2 [M+H]$^+$, RT: 1.748 min.

Compound 1aa: $^1$H NMR (400 MHz, DMSO-d$_6$) δ 0.98 (t, J=7.38 Hz, 3H) 1.67-1.89 (m, 2H) 2.47-2.49 (m, 2H) 2.51-2.53 (m, 2H) 2.78 (d, J=4.88 Hz, 3H) 3.32 (br s, 4H) 3.42 (s, 2H) 4.48 (dd, J=7.75, 4.50 Hz, 1H) 6.82-6.94 (m, 3H) 7.37 (dd, J=8.82, 2.81 Hz, 1H) 7.82 (d, J=8.75 Hz, 1H) 8.11-8.18 (m, 1H) 8.14 (s, 1H) 8.25 (d, J=2.75 Hz, 1H) 8.39 (q, J=4.50 Hz, 1H) 10.61 (s, 1H). LCMS (ESI+): 410.1 [M+H]$^+$, RT: 1.721 min.

Compound 1ab: $^1$H NMR (400 MHz, DMSO-d$_6$) δ 0.98 (t, J=7.38 Hz, 3H) 1.68-1.87 (m, 2H) 2.52 (br s, 4H) 2.77 (d, J=4.88 Hz, 3H) 3.34 (br s, 4H) 3.40-3.45 (m, 2H) 4.48 (dd, J=7.75, 4.50 Hz, 1H) 6.82-6.93 (m, 3H) 7.35-7.41 (m, 1H) 7.82 (d, J=8.88 Hz, 1H) 8.24-8.27 (m, 1H) 8.35-8.42 (m, 1H) 10.58-10.64 (m, 1H). LCMS (ESI+): 410.2 [M+H]$^+$, RT: 1.766 min.

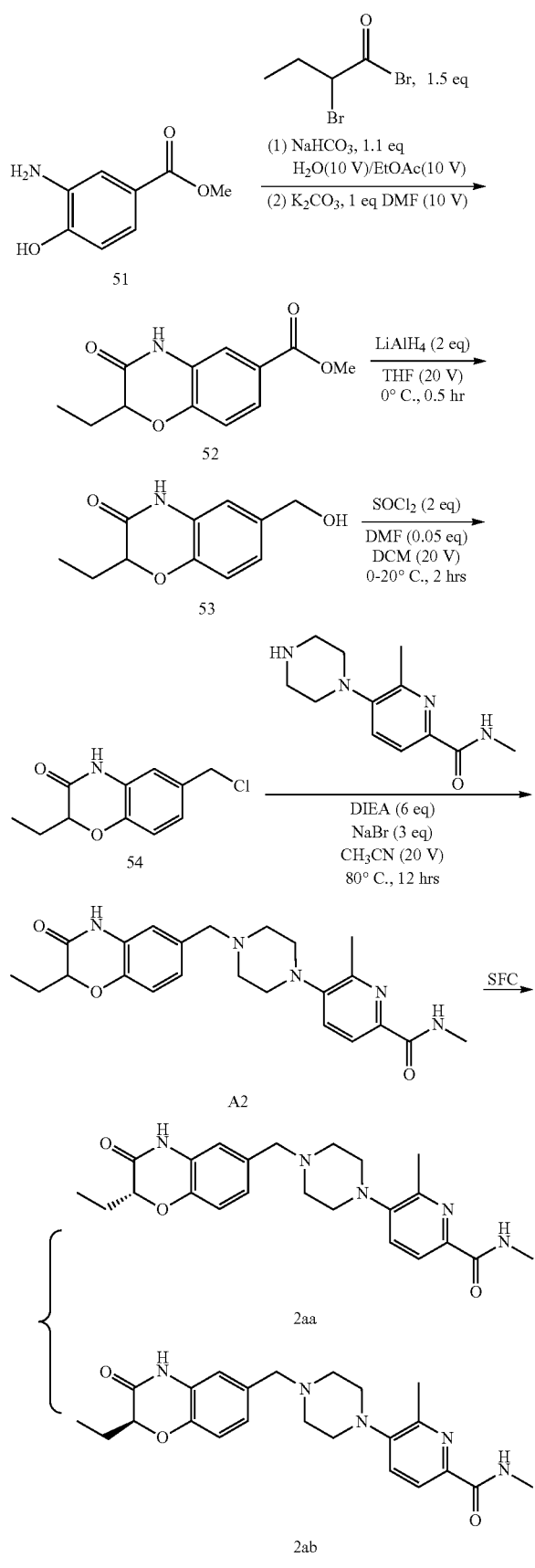

To a solution of 51 (1 g, 5.98 mmol) and 2-bromobutanoyl bromide (1.65 g, 7.18 mmol) in EtOAc (10 mL) and H₂O (10 mL) was added NaHCO₃ (552.80 mg, 6.58 mmol, 255.93 uL) at 25° C. The mixture was stirred at 25° C. for 12 h and then extracted with EA (3×20 mL). The combined organic phase was washed with brine (30 mL), dried over Na₂SO₄ and concentrated to give a residue. The residue was dissolved in DMF (10 mL) and then K₂CO₃ (826.78 mg, 5.98 mmol) was added. The mixture and stirred at 25° C. for 16 h. The mixture was poured into ice-water (30 mL), stirred for 30 min and then filtered. The cake was concentrated under high vacuum to give the crude product, which was used in the next step without further purification. Compound 52 (1 g, 71.06% yield) was obtained as yellow solid. ¹H NMR (400 MHz, DMSO-d₆) δ 10.85 (s, 1H), 7.62-7.47 (m, 2H), 7.06 (d, J=8.4 Hz, 1H), 4.65 (dd, J=4.6, 7.5 Hz, 1H), 3.81 (s, 3H), 1.96-1.70 (m, 2H), 0.98 (t, J=7.3 Hz, 3H).

To a solution of 52 (0.5 g, 2.13 mmol) in THF (10 mL) was added LiAlH₄ (161.35 mg, 4.25 mmol) at 0° C. The mixture was stirred at 0° C. for 0.5 h and then cooled to 0° C. Water (0.22 mL) was added to the mixture at 0° C. dropwise. The mixture was stirred for 5 mins. 15% NaOH (0.0.22 mL) was added to the mixture was at 0° C. and the mixture was stirred for 20 mins. Water (0.66 mL) was added to the mixture at 0° C. dropwise and the mixture was stirred for 5 mins. The mixture was dried over Na₂SO₄ and concentrated to give the crude product. The crude product was triturated with EA (5 mL) for 30 min to give 53 (0.2 g, 45.41% yield) as a white solid.

To a solution of 53 (200 mg, 965.13 umol) and in DCM (4 mL) was added SOCl₂ (229.64 mg, 1.93 mmol, 140.03 uL) at 20° C. The mixture was stirred at 20° C. for 2 h and then concentrated under reduced pressure to give the crude product. The crude product was used in the next step directly without further purification. Compound 54 (150 mg, 68.87% yield) was obtained as a white solid.

To a solution of 54 (150 mg, 572.23 umol, HCl), N,6-dimethyl-5-piperazin-1-yl-pyridine-2-carboxamide (185.92 mg, 686.68 umol, HCl) and NaBr (117.75 mg, 1.14 mmol, 36.80 uL) in MeCN (1 mL) was added DIEA (443.73 mg, 3.43 mmol, 598.02 uL) at 20° C. The mixture was stirred at 80° C. for 2 h. The mixture was filtered and the cake was collected. The filtered cake was separated by SFC to give two product. Compounds 2aa (20.2 mg, 8.34% yield) and 2ab (25.4 mg, 10.48% yield) were obtained as white solids. The absolute configurations of 2aa and 2ab have not yet been determined. The relative configurations are shown above, and the configurations were assigned arbitrarily.

SFC Method: column: ChiralPak IH, 250*30 mm, 10 um; mobile phase: [0.1% NH₃ H₂O EtOH]; B %: 50%-50%, 12 min.

Compound 2aa: ¹H NMR (400 MHz, DMSO-d₆) δ 10.61 (s, 1H), 8.41 (q, J=4.8 Hz, 1H), 7.79 (d, J=8.3 Hz, 1H), 7.47 (d, J=8.4 Hz, 1H), 6.98-6.78 (m, 3H), 4.48 (dd, J=4.6, 7.7 Hz, 1H), 3.44 (s, 2H), 2.93 (br s, 4H), 2.80 (d, J=4.9 Hz, 3H), 2.52 (br s, 4H), 2.48 (s, 3H), 1.89-1.68 (m, 2H), 0.98 (t, J=7.4 Hz, 3H).

Compound 2ab: ¹H NMR (400 MHz, DMSO-d₆) δ 10.63 (s, 1H), 8.43 (q, J=4.7 Hz, 1H), 7.80 (d, J=8.3 Hz, 1H), 7.48 (d, J=8.3 Hz, 1H), 6.99-6.81 (m, 3H), 4.50 (dd, J=4.5, 7.8 Hz, 1H), 3.46 (s, 2H), 2.95 (br s, 4H), 2.81 (d, J=4.9 Hz, 3H), 2.58-2.53 (m, 4H), 2.50 (s, 3H), 1.91-1.69 (m, 2H), 1.00 (t, J=7.4 Hz, 3H).

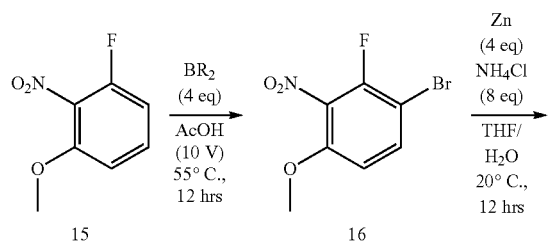
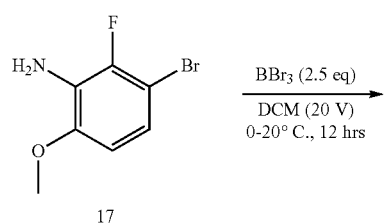
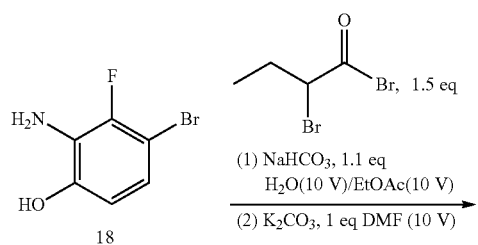
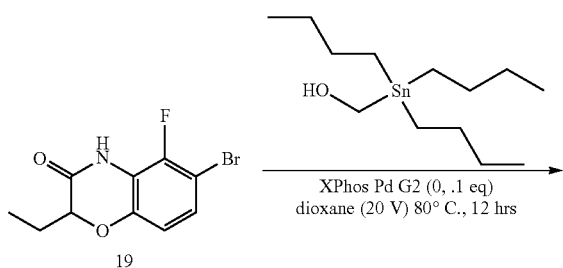
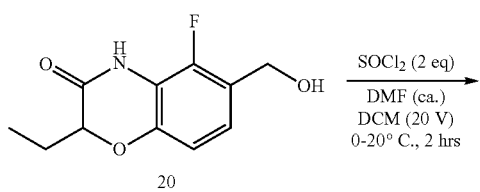
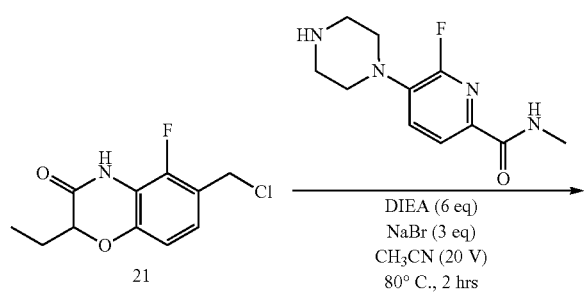

-continued

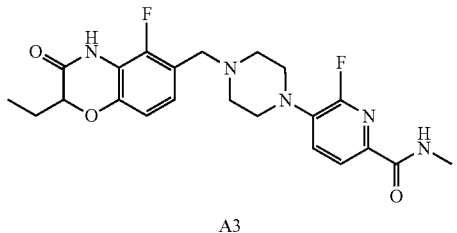

A3

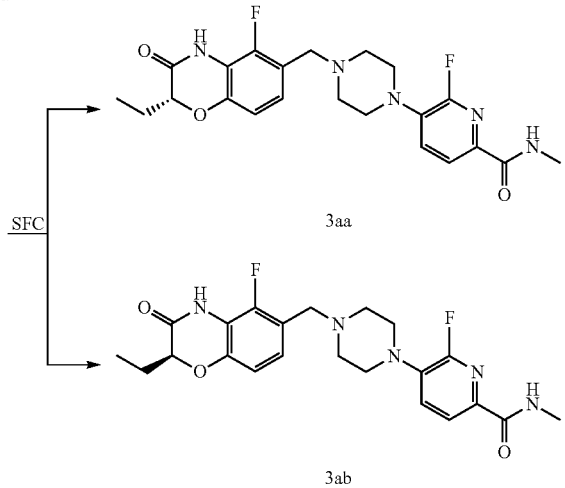

3aa

3ab

To 15 (20 g, 116.87 mmol) in AcOH (200 mL) was added Br$_2$ (74.71 g, 467.49 mmol, 24.10 mL) at 25° C. The mixture was stirred at 55° C. for 12 h and then concentrated under reduced pressure to remove the AcOH. The mixture was extracted with EA (3×40 mL). The combined organic layers were washed with brine (3×30 mL), dried over Na2SO$_4$, filtered and concentrated under reduced pressure to give a residue. The residue was used in the next step, without purification. Compound 16 (24.5 g, 83.84% yield) was obtained as a white solid. $^1$H NMR (400 MHz, DMSO-d$_6$) δ 8.06-7.80 (m, 1H), 7.22 (d, J=9.3 Hz, 1H), 3.95 (s, 3H).

To a solution of 16 (24.5 g, 97.99 mmol) in MeOH (500 mL) was added Zn (25.63 g, 391.97 mmol) in portions (0.5 gram at a time in batches) at 25° C. The mixture was stirred at 25° C. for 2 h. The mixture was filtered and the filtrate was concentrated under reduced pressure to give a residue. The filter cake was with 0.1 N HCl (1 g scale each time) and stirred at 25° C. for 1 h. The mixture was basified by solid NaHCO$_3$ to pH 9. The residue was purified by column chromatography (SiO$_2$, PE:EA=20:1 to 5:1). Compound 17 (19.6 g 90.90% yield) was obtained as a white solid. $^1$H NMR (400 MHz, DMSO-d$_6$) δ 6.80-6.73 (m, 1H), 6.65 (dd, J=1.3, 8.8 Hz, 1H), 4.96 (s, 2H), 3.79 (s, 3H).

To 17 (10 g, 45.45 mmol) in DCM (300 mL) was added BBr$_3$ (28.46 g, 113.62 mmol, 79.53 mL) at 25° C. The mixture was stirred at 25° C. for 12 h and then was poured into NaHCO$_3$ (100 mL). The mixture was stirred at 0° C. for 0.5 h. The mixture was extracted with dichloromethane (3×50 mL). The combined organic layers were washed with brine (3×50 mL), dried over Na$_2$SO$_4$, filtered and concentrated under reduced pressure to give a residue. The residue was purified by column chromatography (SiO$_2$, PE:EA=20:1 to 5:1). Compound 18 (8.3 g, 88.65% yield) was obtained as a white solid. $^1$H NMR (400 MHz, DMSO-d$_6$) δ 9.74 (br s, 1H), 6.63 (dd, J=7.6, 8.7 Hz, 1H), 6.50-6.45 (m, 1H), 4.72 (br s, 2H).

To a solution 18 (10.88 g, 47.33 mmol) in H$_2$O (120 mL) and EA (120 mL) was added NaHCO$_3$ (2.92 g, 34.71 mmol, 1.35 mL) and 2-amino-4-bromo-3-fluoro-phenol (6.5 g, 31.55 mmol) at 25° C. The mixture was stirred at 25° C. for 12 h and then concentrated under reduced pressure to give a residue. The residue in DMF (120 mL) was added K$_2$CO$_3$ (4.36 g, 31.55 mmol) at 25° C. The mixture was stirred at 25° C. for 12 h. The mixture was poured into ice-water (360 mL) and then filtered. The filter cake was dried under high vacuum to give the product. The residue was used in next step directly without further purification. Compound 19 (8.4 g, 97.13% yield) was obtained as a white solid. $^1$H NMR (400 MHz, DMSO-d$_6$) δ 11.05 (br s, 1H), 7.20 (dd, J=7.5, 8.6 Hz, 1H), 6.83 (dd, J=1.5, 8.8 Hz, 1H), 4.58 (dd, J=4.6, 7.8 Hz, 1H), 1.97-1.64 (m, 2H), 0.98 (t, J=7.4 Hz, 3H).

A mixture of 19 (8.79 g, 27.36 mmol) 6-bromo-2-ethyl-5-fluoro-4H-1,4-benzoxazin-3-one (5 g, 18.24 mmol) and [2-(2-aminophenyl)phenyl]-chloro-palladium; dicyclohexyl-[3-(2,4,6-triisopropylphenyl)phenyl]phosphane (1.44 g, 1.82 mmol) in dioxane (100 mL) was degassed and purged with N$_2$ (3×). The mixture was stirred at 80° C. for 12 h under N$_2$ atmosphere. The mixture was filtered and the filtrate was concentrated under reduced pressure to give a residue. The residue was purified by column chromatography (SiO$_2$, PE:EA=50:1 to 1:1). Compound 20 (3.7 g, 90.06% yield) was obtained as a white solid. $^1$H NMR (400 MHz, DMSO-d$_6$) δ 10.83 (s, 1H), 6.97 (t, J=8.1 Hz, 1H), 6.80 (d, J=8.5 Hz, 1H), 5.18 (t, J=5.7 Hz, 1H), 4.52 (dd, J=4.6, 7.9 Hz, 1H), 4.45 (d, J=5.7 Hz, 2H), 1.91-1.63 (m, 2H), 0.98 (t, J=7.4 Hz, 3H).

A mixture of 20 (6.3 g, 27.97 mmol) and SOCl$_2$ (6.66 g, 55.95 mmol, 4.06 mL) in DCM (120 mL) was degassed and purged with N$_2$ (3×). The mixture was stirred at 25° C. for 2 h under N$_2$ atmosphere. The mixture was filtered and the filter cake was concentrated under reduced pressure to give a residue. The residue was used in the next step directly without further purification. Compound 21 (6.5 g, 95.36% yield) was obtained as a white solid.

A mixture of 21 (3.10 g, 12.74 mmol), 6-fluoro-N-methyl-5-piperazin-1-yl-pyridine-2-carboxamide (3.5 g, 12.74 mmol, HCl), DIEA (9.88 g, 76.44 mmol, 13.31 mL) and NaBr (3.93 g, 38.22 mmol, 1.23 mL) in CH$_3$CN (100 mL) was degassed and purged with N$_2$ (3×). The mixture was stirred at 25° C. for 2 h under N$_2$ atmosphere. The mixture was filtered and the filter cake was concentrated under reduced pressure to give a residue that was separated by SFC and concentrated to give two products (Rt$_1$=1.518 min, Rt$_2$=1.747 min). The residue was purified by prep-HPLC FA condition). Compounds 3aa (0.97 g, 17.09% yield) and 3ab (1.7 g, 29.95% yield) were obtained as white solids. The absolute configurations of 3aa and 3ab have not yet been determined. The relative configurations are shown above, and the configurations were assigned arbitrarily.

Prep-HPLC Method: column: ChiralPak IH, 250*30 mm, 10 um; mobile phase: [0.1% NH₃ H₂O EtOH]; B %: 50%-50%, 12 min. SFC Method: column: ChiralPak IH, 250*30 mm, 10 um; mobile phase: [0.1% NH₃ H₂O EtOH]; B %: 50%-50%, 12 min Compound 3aa: $^1$H NMR (400 MHz, DMSO-$d_6$) δ 1.00 (t, J=7.38 Hz, 3H) 1.68-1.93 (m, 2H) 2.55 (br s, 4H) 2.77 (d, J=4.75 Hz, 3H) 3.15 (br s, 4H) 3.54 (br s, 2H) 4.55 (dd, J=7.69, 4.57 Hz, 1H) 6.82 (d, J=8.38 Hz, 1H) 6.95 (t, J=7.94 Hz, 1H) 7.55 (dd, J=10.51, 8.13 Hz, 1H) 7.84 (d, J=7.88 Hz, 1H) 8.40 (q, J=4.38 Hz, 1H) 10.84 (s, 1H).

Compound 3ab: $^1$H NMR (400 MHz, DMSO-$d_6$) δ 0.99 (t, J=7.38 Hz, 3H) 1.67-1.92 (m, 2H) 2.54 (br d, J=4.25 Hz, 4H) 2.76 (d, J=4.88 Hz, 3H) 3.14 (br s, 4H) 3.53 (br s, 2H) 4.55 (dd, J=7.69, 4.57 Hz, 1H) 6.81 (d, J=8.38 Hz, 1H) 6.90-6.98 (m, 1H) 7.54 (dd, J=10.57, 8.19 Hz, 1H) 7.72-8.04 (m, 1H) 8.39 (q, J=4.42 Hz, 1H) 10.83 (s, 1H).

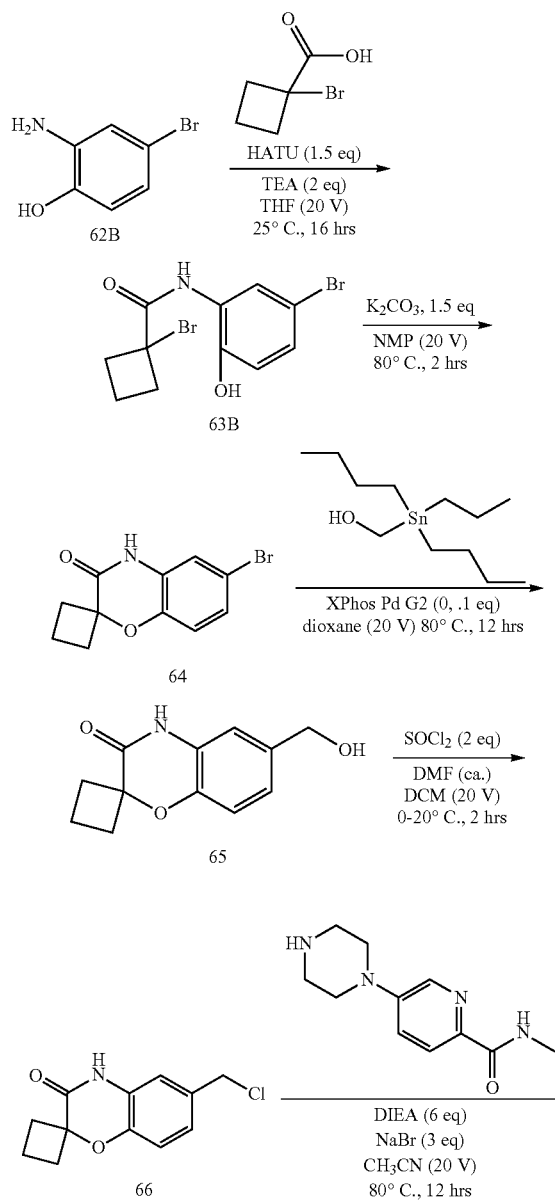

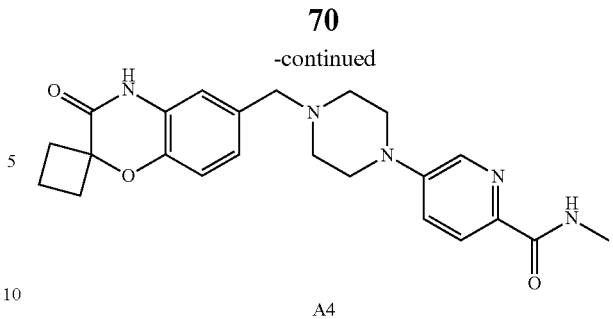

A4

To a solution of 1-bromocyclobutanecarboxylic acid (2 g, 11.17 mmol) in THF (20 mL) were added TEA (2.26 g, 22.34 mmol, 3.11 mL) and HATU (6.37 g, 16.76 mmol) at 25° C. The mixture was stirred at 25° C. for 0.5 h. Compound 62B (2.10 g, 11.17 mmol) was added to the mixture. The mixture was stirred at 25° C. for 12 h. The mixture was extracted with EA (3×10 mL). The combined organic layers were washed with brine (3×10 mL), dried over Na₂SO₄, filtered and concentrated under reduced pressure to give a residue. The residue was purified by column chromatography (SiO₂, PE:EA=50:1 to 2:1). Compound 63 B (3.1 g, 79.50% yield) was obtained as a white solid. $^1$H NMR ET59875-73-P1A (400 MHz, DMSO-$d_6$) δ 1.73-1.93 (m, 1H) 2.12-2.28 (m, 1H) 2.54-2.69 (m, 2H) 2.91-3.04 (m, 2H) 6.86 (d, J=8.63 Hz, 1H) 7.16 (dd, J=8.57, 2.44 Hz, 1H) 7.96 (d, J=2.38 Hz, 1H) 9.01 (s, 1H) 10.33 (br s, 1H)

A mixture of 63B (1 g, 2.87 mmol) and K₂CO₃ (593.99 mg, 4.30 mmol) in NMP (20 mL) was degassed and purged with N₂ (3×). The mixture was stirred at 80° C. for 2 h under N₂ atmosphere. The mixture was filtered and the filtrate concentrated under reduced pressure to give a residue. The residue was used in the next step directly without purification. Compound 64 (680 mg, 88.52% yield) was obtained as a white solid.

To a mixture of [dibutyl(propyl)stannyl]methanol (171.79 mg, 559.48 umol) and 64 (100 mg, 372.99 umol) in dioxane (6 mL) was added XPhos-Pd-G2 (29.35 mg, 37.30 umol) at 25° C. The mixture was degassed and purged with N₂ (3×). The mixture was stirred at 80° C. for 12 h under N₂ atmosphere. The mixture was filtered and the filtrate was concentrated under reduced pressure to give a residue. The residue was purified by column chromatography (SiO₂, PE:EA=50:1 to 2:1). Compound 65 (98 mg, 97.83% yield) was obtained as a white solid.

To a solution of 65 (98 mg, 456.13 umol) in DCM (5 mL) was added SOCl₂ (108.53 mg, 912.26 umol, 66.18 uL) at 25° C. The mixture was stirred at 25° C. for 2 h. The mixture was filtered and the filter cake was concentrated under reduced pressure to give a residue. The residue was used in the next step directly without purification. Compound 66 (95 mg, 98.4% yield) was obtained as a white solid.

To a mixture of N-methyl-5-piperazin-1-yl-pyridine-2-carboxamide (111.21 mg, 433.17 umol, HCl) 66 (80 mg, 336.58 umol) in ACN (2 mL) were added NaBr (103.90 mg, 1.01 mmol, 32.47 uL) and DIEA (261.01 mg, 2.02 mmol, 351.76 uL) at 25° C. The mixture was degassed and purged with N₂ (3×). The mixture was stirred at 80° C. for 2 h under N₂ atmosphere. The mixture was filtered and the filtrate was concentrated under reduced pressure to give a residue. The residue was purified by prep-HPLC (FA condition). Compound A4 (92 mg, 55.54% yield, 95.0% purity, FA) was obtained as a yellow solid. Prep-HPLC Method: column: Phenomenex C18 75*30 mm*3 um; mobile phase: [water (FA)-ACN]; B %: 20%-45%, 8 min. $^1$H NMR (400 MHz, DMSO-d$_6$) δ 11.03 (s, 1H), 8.41 (br d, J=4.8 Hz, 1H), 8.28 (br s, 1H), 8.13 (s, 1H), 7.85 (br d, J=8.8 Hz, 1H), 7.41 (br d, J=7.6 Hz, 1H), 7.10-6.86 (m, 3H), 4.45-3.72 (m, 2H), 3.28-2.92 (m, 4H), 2.78 (d, J=4.8 Hz, 3H), 2.55-2.50 (m, 4H), 2.49-2.45 (m, 2H), 2.28-2.13 (m, 2H), 1.99-1.85 (m, 1H), 1.85-1.71 (m, 1H).

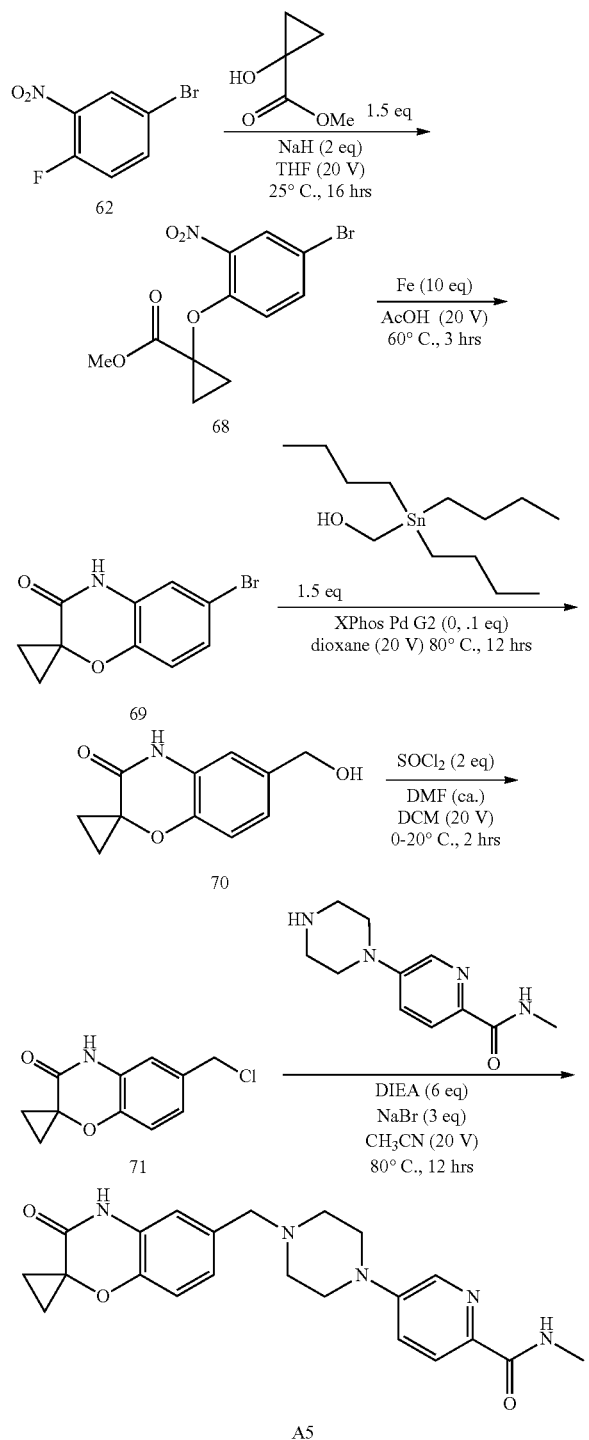

g, 4.55 mmol, 558.66 uL) was added to the mixture at 25° C. The mixture was degassed and purged with Ar (3×). The mixture was stirred at 25° C. for 12 h under Ar atmosphere. The mixture was poured into NH$_4$Cl and then filtered. The filter cake was concentrated under reduced pressure to give a residue. The residue was used in the next step directly without purification. Compound 68 (0.9 g, 62.64% yield) was obtained as a white solid. $^1$H NMR (400 MHz, DMSO-d$_6$) δ 1.34-1.50 (m, 2H) 1.56-1.70 (m, 2H) 3.66 (s, 3H) 7.22-7.38 (m, 1H) 7.74-7.90 (m, 1H) 8.05-8.21 (m, 1H).

A solution 68 (810 mg, 2.56 mmol) and Fe (1.43 g, 25.62 mmol) in HOAc (18 mL) was degassed and purged with N$_2$ (3×). The mixture was stirred at 60° C. for 3 h under N$_2$ atmosphere. The mixture was filtered and the filtrate concentrated under reduced pressure to give a residue. The residue was used in the next step directly without purification. Compound 69 (580 mg, 89.08% yield) was obtained as a white solid. $^1$H NMR (400 MHz, DMSO-d$_6$) δ 1.15-1.21 (m, 2H) 1.21-1.29 (m, 2H) 3.33 (s, 1H) 6.84 (d, J=8.25 Hz, 1H) 7.01-7.14 (m, 1H) 10.87 (s, 1H).

To a solution of tributylstannylmethanol (947.79 mg, 2.95 mmol) and 69 (500 mg, 1.97 mmol) in dioxane (10 mL) was added XPhos-Pd-G2 (154.83 mg, 196.79 umol) at 25° C. The mixture was degassed and purged with N$_2$ (3×). The mixture was stirred at 80° C. for 12 h under N$_2$ atmosphere. The mixture was filtered and the filter cake concentrated under reduced pressure to give a residue. The residue was used in the next step directly without purification. Compound 70 (180 mg, 44.57% yield) was obtained as a white solid. $^1$H NMR (400 MHz, DMSO-d$_6$) δ 1.10-1.18 (m, 2H) 1.19-1.26 (m, 2H) 4.39 (d, J=5.75 Hz, 2H) 5.14 (t, J=5.69 Hz, 1H) 6.77-6.96 (m, 3H) 10.74 (s, 1H).

To a solution of 70 (100 mg, 487.31 umol) in DCM (2 mL) was added SOCl$_2$ (115.95 mg, 974.61 umol, 70.70 uL) at 0° C. The mixture was stirred at 20° C. for 2 h. The mixture was filtered and the filter cake concentrated under reduced pressure to give a residue. The residue was used in the next step directly without purification. Compound 71 (100 mg, 91.75% yield) was obtained as a white solid.

To a mixture of N-methyl-5-piperazin-1-yl-pyridine-2-carboxamide (154.96 mg, 603.61 umol, HCl) and 71 (90 mg, 402.41 umol) in ACN (1.8 mL) were added DIEA (312.05 mg, 2.41 mmol, 420.55 uL) and NaBr (124.22 mg, 1.21 mmol, 38.82 uL) at 25° C. The mixture was degassed and purged with N$_2$ (3×). The mixture was stirred at 80° C. for 2 h under N$_2$ atmosphere. The mixture was concentrated under reduced pressure to give a residue. The residue was purified by prep-HPLC (neutral condition). Compound A4 (44.4 mg, 27.08% yield) was obtained as a yellow solid. Prep-HPLC Method: column: Waters Xbridge BEH C18 100*30 mm*10 um; mobile phase: [water (NH$_4$HCO$_3$)-ACN]; B %: 25%-55%, 8 min. $^1$H NMR (400 MHz, DMSO-d$_6$) δ 1.13-1.19 (m, 2H) 1.20-1.26 (m, 2H) 2.51 (br s, 4H) 2.78 (d, J=4.88 Hz, 3H) 3.32-3.34 (m, 4H) 3.44 (s, 2H) 6.80-6.88 (m, 2H) 6.92 (d, J=1.63 Hz, 1H) 7.38 (dd, J=8.82, 2.94 Hz, 1H) 7.77 (br d, J=4.13 Hz, 1H) 8.25 (d, J=2.75 Hz, 1H) 8.32-8.43 (m, 1H) 10.72 (s, 1H).

To a mixture of methyl 1-hydroxycyclopropanecarboxylate (791.71 mg, 6.82 mmol) in THF (20 mL) was added NaH (363.61 mg, 9.09 mmol, 60% purity) at 0° C. The mixture was stirred at 25° C. for 15 mins. Compound 62 (1

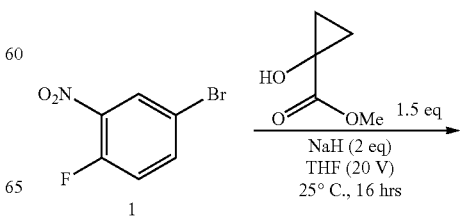

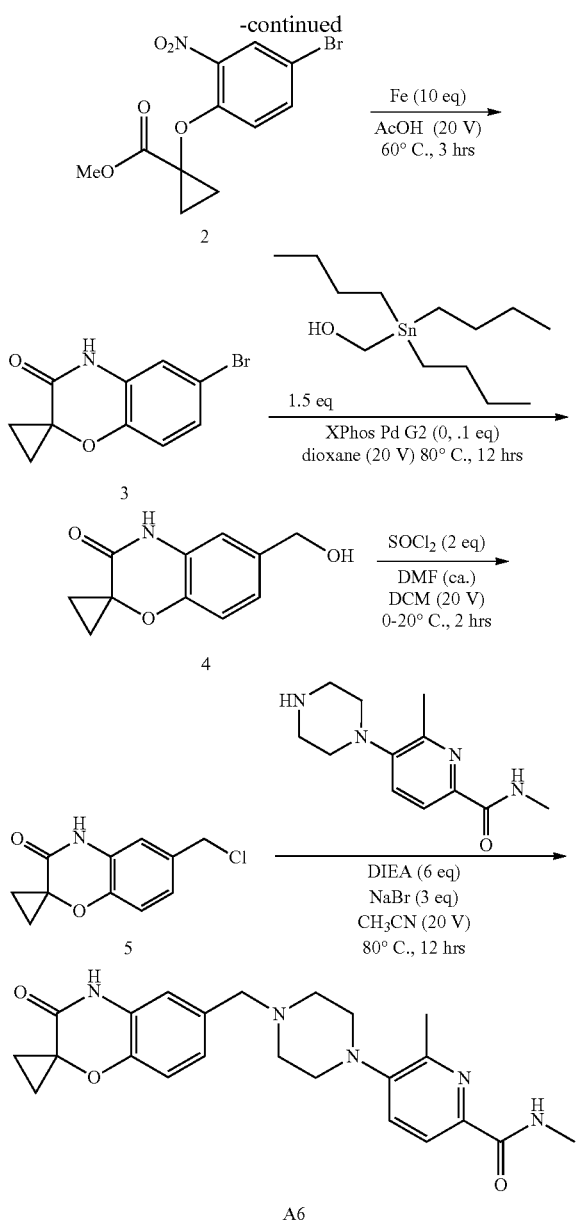

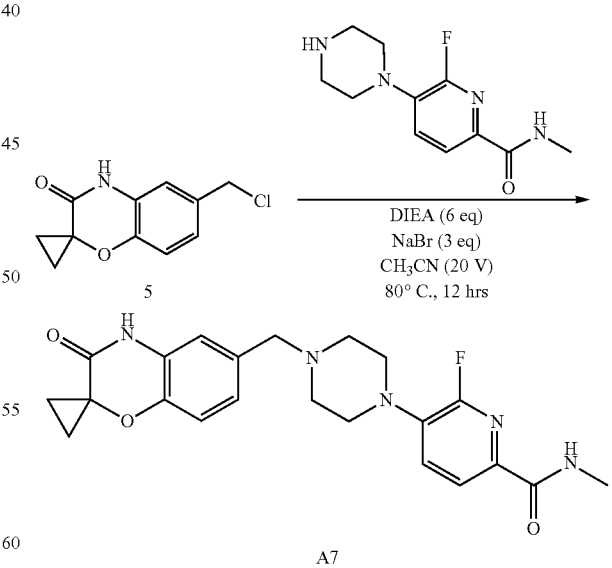

To a solution of 1 (1 g, 4.55 mmol) and ethyl 1-hydroxy-cyclopropanecarboxylate (887.34 mg, 6.82 mmol) in THF (20 mL) was added NaH (363.64 mg, 9.09 mmol, 60% purity) at 0° C. under $N_2$. The mixture was stirred at 20° C. for 12 h. The mixture was poured into aq·$NH_4Cl$ (20 mL) at 0° C. and then extracted with EA (3×20 mL). The combined organic phase was washed with brine (20 mL), dried over $Na_2SO_4$ and concentrated to give the crude product. The residue was purified by column chromatography ($SiO_2$, PE:EA=50:1 to 3:1). Compound 2 (1.2 g, 79.97% yield) was obtained as a yellow solid. $^1$H NMR (400 MHz, DMSO-$d_6$) δ 8.16 (d, J=2.4 Hz, 1H), 7.83 (dd, J=2.5, 9.0 Hz, 1H), 7.31 (d, J=9.0 Hz, 1H), 4.14 (q, J=7.1 Hz, 2H), 1.66-1.58 (m, 2H), 1.48-1.39 (m, 2H), 1.13 (t, J=7.1 Hz, 3H).

A mixture of 2 (1.2 g, 3.63 mmol), Fe (2.03 g, 36.35 mmol), in AcOH (20 mL) was degassed and purged with $N_2$ (3×). The mixture was stirred at 60° C. for 3 h under $N_2$ atmosphere. The mixture was filtered and the filtrate was concentrated to give the crude product. The residue was purified by column chromatography ($SiO_2$, PE:EA=50:1 to 1:1). Compound 3 (530 mg, 57.39% yield) was obtained as a yellow solid. $^1$H NMR (400 MHz, DMSO-$d_6$) δ 10.87 (br s, 1H), 7.11-7.02 (m, 2H), 6.85 (d, J=8.5 Hz, 1H), 3.32 (s, 18H), 1.29-1.22 (m, 2H), 1.21-1.16 (m, 2H).

To a solution of tributylstannylmethanol (1.00 g, 3.13 mmol) and XPhos-Pd-G2 (164.12 mg, 208.60 umol) in dioxane (10 mL) was added 3 (530 mg, 2.09 mmol) at 25° C. The mixture was stirred at 80° C. for 12 h. The mixture was filtered and the filtrate was concentrated to give the crude product. The residue was purified by column chromatography ($SiO_2$, PE:EA=3:1 to 2:1). Compound 4 (390 mg, 91.11% yield) was obtained as a white solid.

A solution of 4 (390 mg, 1.90 mmol) and $SOC_2$ (452.20 mg, 3.80 mmol, 275.73 uL) in DCM (5 mL) was stirred at 25° C. for 2 h. The mixture was filtered and the filtrate was concentrated to give the crude product. The crude product was used in the next step directly without further purification. Compound 5 (300 mg, 70.58% yield) was obtained as a white solid. $^1$H NMR (400 MHz, DMSO-$d_6$) δ 10.94-10.79 (m, 1H), 7.11-6.91 (m, 2H), 6.86 (d, J=7.9 Hz, 1H), 4.82-4.53 (m, 2H), 1.35-1.05 (m, 4H).

To a solution of N,6-dimethyl-5-piperazin-1-yl-pyridine-2-carboxamide (80 mg, 341.45 umol) and DIEA (173.36 mg, 1.34 mmol, 233.64 uL) in $CH_3CN$ (1 mL) were added 5 (50 mg, 223.56 umol) and NaBr (69.01 mg, 670.68 umol, 21.57 uL) at 25° C. The mixture was stirred at 80° C. for 12 h. The mixture was filtered and the filtrate was concentrated to give the crude product. The residue was purified by prep-HPLC (neutral condition). Compound A6 (58.1 mg, 61.66% yield) was obtained as a white solid. Prep-HPLC Method: column: Waters Xbridge BEH C18 100*30 mm*10 um; mobile phase: [water($NH_4HCO_3$)-ACN]; B %: 35%-65%, 8 min $^1$H NMR (400 MHz, DMSO-$d_6$) δ 10.87-10.53 (m, 1H), 8.47-8.37 (m, 1H), 7.79 (d, J=8.3 Hz, 1H), 7.47 (d, J=8.3 Hz, 1H), 6.92 (d, J=1.8 Hz, 1H), 6.89-6.80 (m, 2H), 3.45 (s, 2H), 3.01-2.73 (m, 7H), 2.68-2.50 (m, 7H), 1.26-1.20 (m, 2H), 1.19-1.12 (m, 2H).

To a solution of 5 (80 mg, 335.77 umol) and DIEA (260.37 mg, 2.01 mmol, 350.90 uL) in $CH_3CN$ (1.6 mL) were added 6-(chloromethyl)spiro[4H-1,4-benzoxazine-2,1'-cyclopropane]-3-one (75.10 mg, 335.77 umol) and NaBr (103.64 mg, 1.01 mmol, 32.39 uL). The mixture was stirred at 80° C. for 12 h. The mixture was filtered and the filtrate was concentrated to give the crude product. The residue was purified by prep-HPLC (neutral condition). Compound A7 (67.5 mg, 47.70% yield) was obtained as a white solid. Prep-HPLC Method: column: Waters Xbridge BEH C18 100*30 mm*10 um; mobile phase: [water(NH₄HCO₃)-ACN]; B %: 35%-65%, 8 min. ¹H NMR (400 MHz, DMSO-d₆) δ 10.81-10.61 (m, 1H), 8.39 (q, J=4.5 Hz, 1H), 7.84 (dd, J=1.1, 8.0 Hz, 1H), 7.55 (dd, J=8.2, 10.6 Hz, 1H), 6.96-6.75 (m, 3H), 3.44 (s, 2H), 3.15 (br d, J=4.5 Hz, 4H), 2.76 (d, J=4.8 Hz, 3H), 1.27-1.20 (m, 2H), 1.19-1.11 (m, 2H).

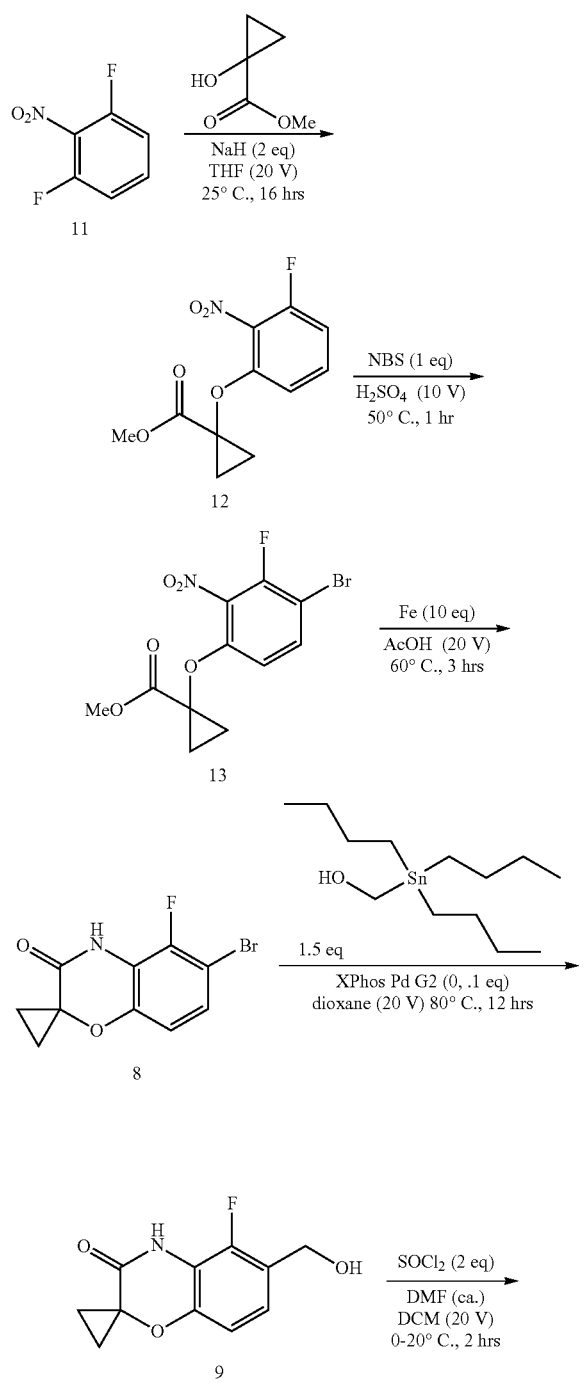

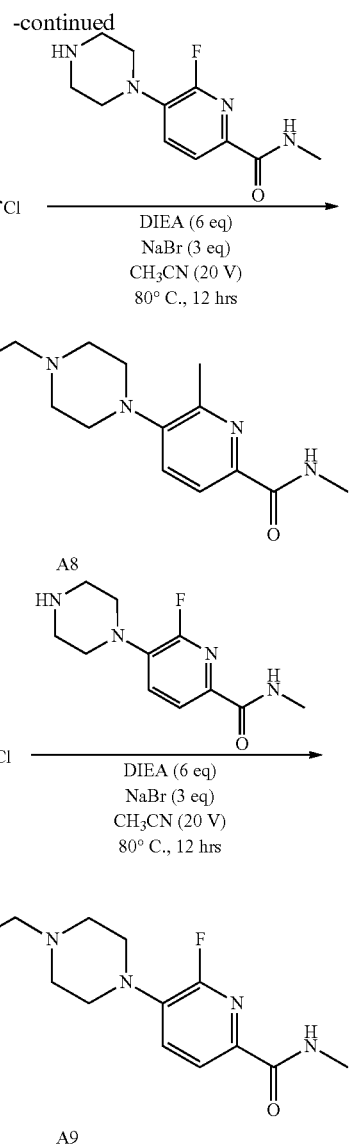

To a solution of 11 (1 g, 6.29 mmol, 666.67 uL) and methyl 1-hydroxycyclopropanecarboxylate (696.69 mg, 6.00 mmol) in THF (20 mL) was added NaH (342.86 mg, 8.57 mmol, 60% purity) at 0° C. under N₂. The mixture was stirred at 20° C. for 12 h. The mixture was poured into a·NH₄Cl (50 mL) at 0° C. The mixture was extracted with EA (3×10 mL). The combined organic phase was washed with brine (20 mL), dried over Na₂SO₄ and concentrated to give the crude product. The residue was purified by column chromatography (SiO₂, PE:EA=50:1 to 1:50). Compound 12 (1 g, 68.57% yield) was obtained as a yellow solid. ¹H NMR (400 MHz, DMSO-d₆) δ 7.63 (dt, J=6.5, 8.6 Hz, 1H), 7.29-7.15 (m, 2H), 3.68 (s, 3H), 1.67-1.60 (m, 2H), 1.48-1.40 (m, 2H).

To a solution of 12 (1 g, 3.92 mmol) in H₂SO₄ (10 mL) was added NBS (697.43 mg, 3.92 mmol) at 0° C. under N₂. The mixture was stirred at 25° C. for 12 h. The mixture was poured into ice-water (20 mL) at 0° C. The mixture was extracted with EA (3×20 mL). The combined organic phase was washed with brine (20 mL), dried over Na₂SO₄ and concentrated to give the crude product. The residue was purified by column chromatography (SiO₂, PE:EA=50:1 to 4:1). Compound 13 (0.7 g, 53.47% yield) was obtained as a yellow solid. $^1$H NMR (400 MHz, DMSO-d$_6$) δ 7.91 (dd, J=7.9, 9.3 Hz, 1H), 7.21 (dd, J=1.7, 9.3 Hz, 1H), 3.67 (s, 3H), 1.65-1.59 (m, 2H), 1.47-1.42 (m, 2H).

To a solution of 13 (700 mg, 2.10 mmol) in AcOH (10 mL) was added Fe (1.17 g, 20.95 mmol) at 25° C. under N$_2$. The mixture was stirred at 60° C. for 3 h. The mixture was poured into aq. NH$_4$Cl (20 mL) at 0° C. The mixture was extracted with EA (3×20 mL). The combined organic phase was washed with brine (20 mL), dried over Na$_2$SO$_4$ and concentrated to give the crude product. The residue was purified by column chromatography (SiO$_2$, PE:EA=50:1 to 1:50). Compound 8 (560 mg, 98.24% yield) was obtained as a yellow solid. $^1$H NMR (400 MHz, DMSO-d$_6$) δ 11.38-11.04 (m, 1H), 7.22 (dd, J=7.5, 8.6 Hz, 1H), 6.75 (dd, J=1.3, 8.8 Hz, 1H), 1.32-1.26 (m, 2H), 1.26-1.19 (m, 2H).

A mixture of 8 (560 mg, 2.06 mmol), tributylstannylmethanol (991.33 mg, 3.09 mmol) in dioxane (10 mL) was degassed and purged with N$_2$ (3×), and then [2-(2-aminophenyl)phenyl]-chloro-palladium; dicyclohexyl-[3-(2,4,6-triisopropylphenyl)phenyl]phosphane (161.95 mg, 205.83 umol) was added to the mixture under N$_2$. The mixture was stirred at 80° C. for 12 h under N$_2$ atmosphere. The mixture was filtered and concentrated to give the crude product. The residue was purified by column chromatography (SiO$_2$, PE:EA=50:1 to 3:1). Compound 9 (320 mg, 69.65% yield) was obtained as a white solid. $^1$H NMR (400 MHz, DMSO-d$_6$) δ 7.80 (br d, J=0.8 Hz, 1H), 6.99 (t, J=8.2 Hz, 1H), 6.68 (dd, J=0.9, 8.4 Hz, 1H), 4.72 (s, 2H), 1.51-1.44 (m, 2H), 1.30-1.24 (m, 2H).

A mixture of 9 (320 mg, 1.43 mmol) in DCM (0.5 mL) was degassed and purged with N$_2$ (3×), and then SOCl$_2$ (341.13 mg, 2.87 mmol, 208.01 uL) was added under N$_2$. The mixture was stirred at 25° C. for 2 h under N$_2$ atmosphere. The mixture was concentrated to give a residue. The residue was used in the next step directly without further purification. Compound 14 (250 mg, 72.16% yield) was obtained as a white solid.

To a solution of N,6-dimethyl-5-piperazin-1-yl-pyridine-2-carboxamide (89.64 mg, 331.06 umol, HCl) and DIEA (256.72 mg, 1.99 mmol, 345.98 uL) in CH$_3$CN (0.5 mL) were added 14 (80 mg, 331.06 umol) and NaBr (102.19 mg, 993.19 umol, 31.93 uL) at 25° C. The mixture was stirred at 80° C. for 12 h. The mixture was filtered and the filtrate was concentrated to give the crude product. The residue was purified by prep-HPLC to give A8 (97.6 mg, 60.11% yield) as a white solid. Column: Phenomenex Luna C18 75*30 mm*3 um; mobile phase: [water(FA)-ACN]; B %: 5%-40%, 8 min. $^1$H NMR (400 MHz, DMSO-d$_6$) δ 10.97 (s, 1H), 8.46-8.35 (m, 1H), 8.15 (s, 1H), 7.78 (d, J=8.3 Hz, 1H), 7.46 (d, J=8.3 Hz, 1H), 6.95 (t, J=7.9 Hz, 1H), 6.73 (d, J=8.4 Hz, 1H), 3.55 (s, 2H), 2.92 (br s, 4H), 2.79 (d, J=4.8 Hz, 3H), 2.57 (br s, 4H), 2.48 (s, 3H), 1.31-1.24 (m, 2H), 1.23-1.17 (m, 2H).

To a solution of 6-fluoro-N-methyl-5-piperazin-1-yl-pyridine-2-carboxamide (90.95 mg, 331.06 umol, HCl) and DIEA (256.72 mg, 1.99 mmol, 345.98 uL) in CH$_3$CN (0.5 mL) were added 10 (80 mg, 331.06 umol) and NaBr (102.19 mg, 993.19 umol, 31.93 uL) at 25° C. The mixture was stirred at 80° C. for 12 h. The mixture was filtered and the filtrate was concentrated to give the crude product. The residue was purified by prep-HPLC (or neutral condition). Compound A9 (72.6 mg, 148.18 umol, 44.76% yield, 99.9% purity, FA salt) was obtained as a white solid. column: Phenomenex Luna C18 75*30 mm*3 um; mobile phase: [water (FA)-ACN]; B %: 5%-40%, 8 min, $^1$H NMR (400 MHz, DMSO-d$_6$) δ 10.97 (s, 1H), 8.39 (q, J=4.4 Hz, 1H), 7.83 (d, J=8.1 Hz, 1H), 7.54 (dd, J=8.3, 10.4 Hz, 1H), 6.95 (t, J=8.0 Hz, 1H), 6.73 (d, J=8.4 Hz, 1H), 3.54 (s, 2H), 3.14 (br s, 4H), 2.76 (d, J=4.9 Hz, 3H), 2.55 (br s, 4H), 1.31-1.24 (m, 2H), 1.23-1.16 (m, 2H).

Example 9

Additional Compounds

Additional compounds of Formula (I) can be prepared using similar materials and methods described herein, such as those described herein.

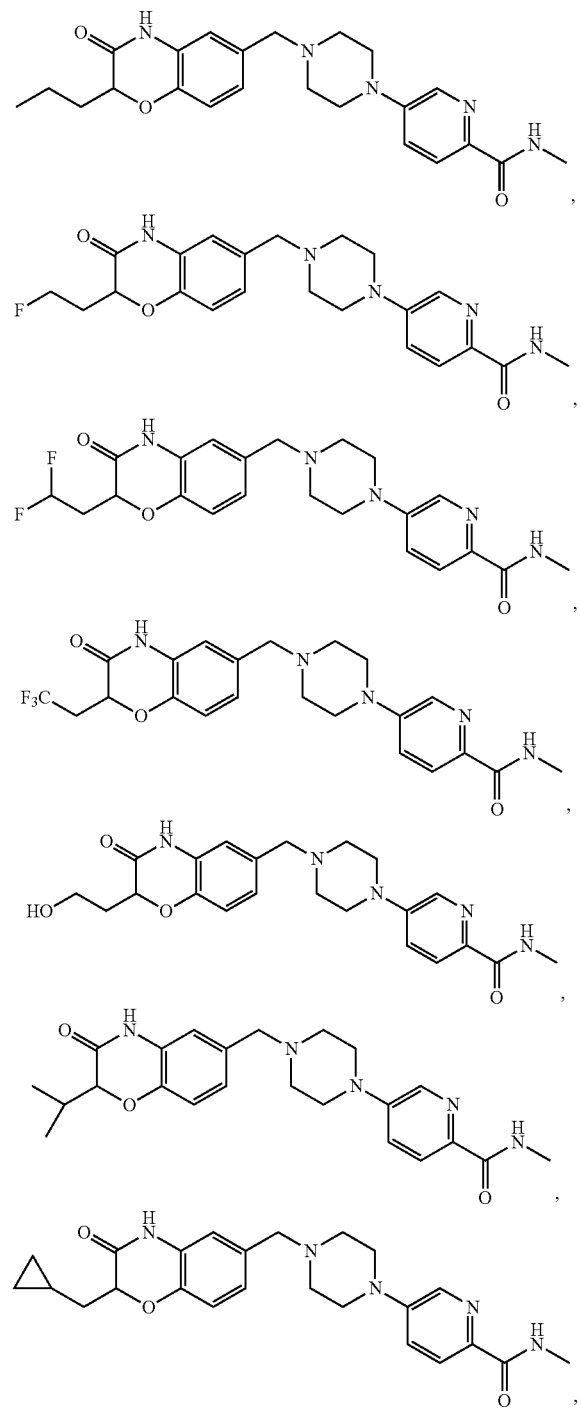

-continued

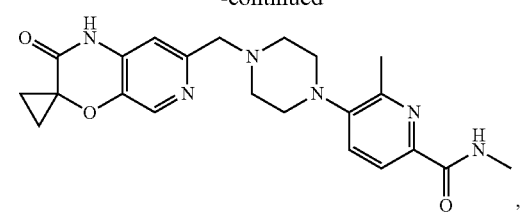
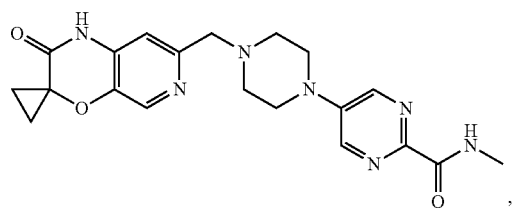
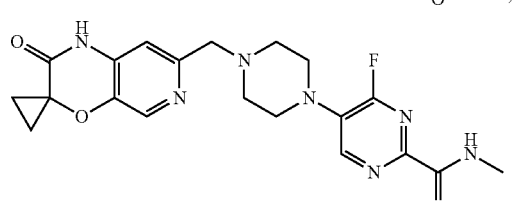
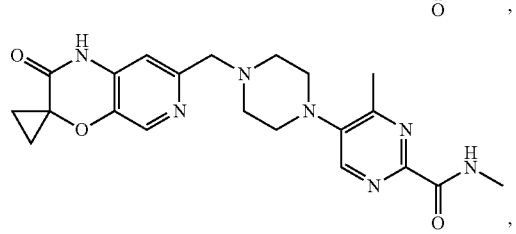
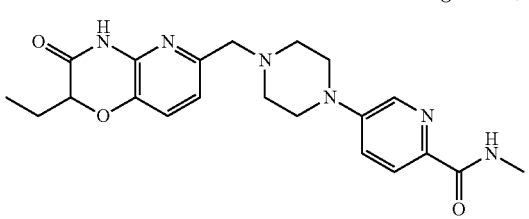
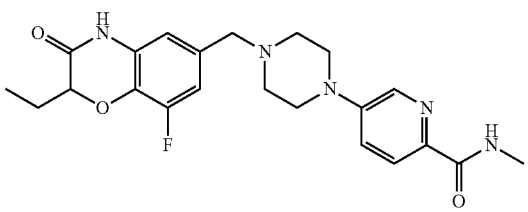
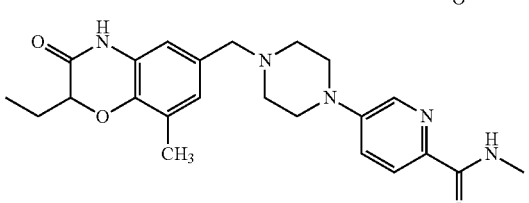
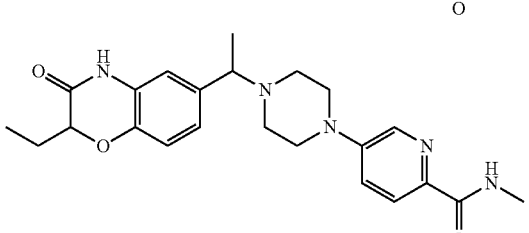
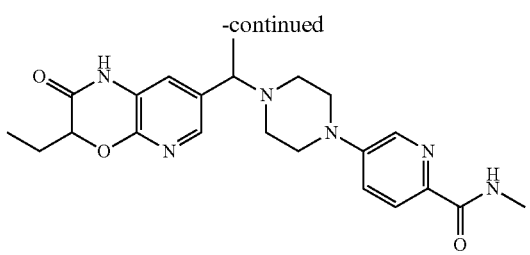
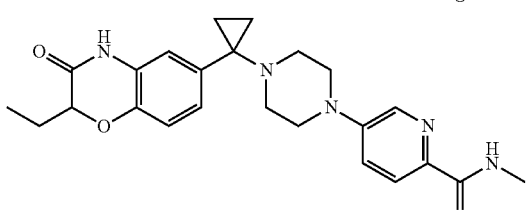
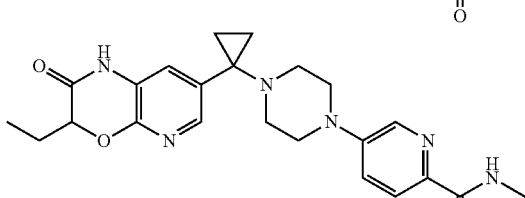
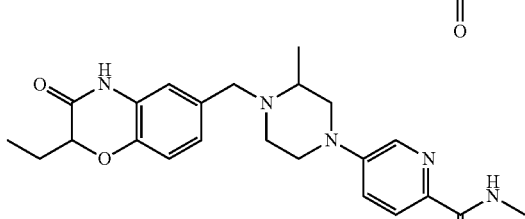
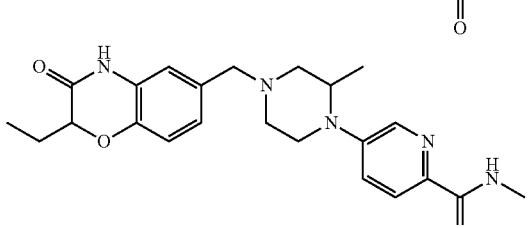
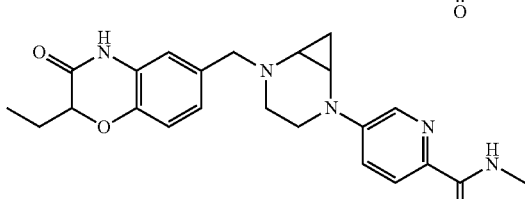
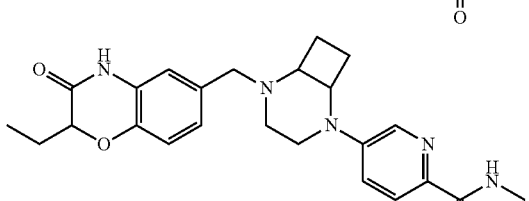
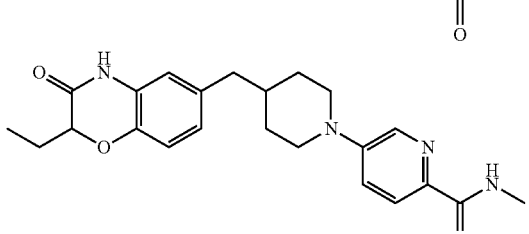

-continued

-continued

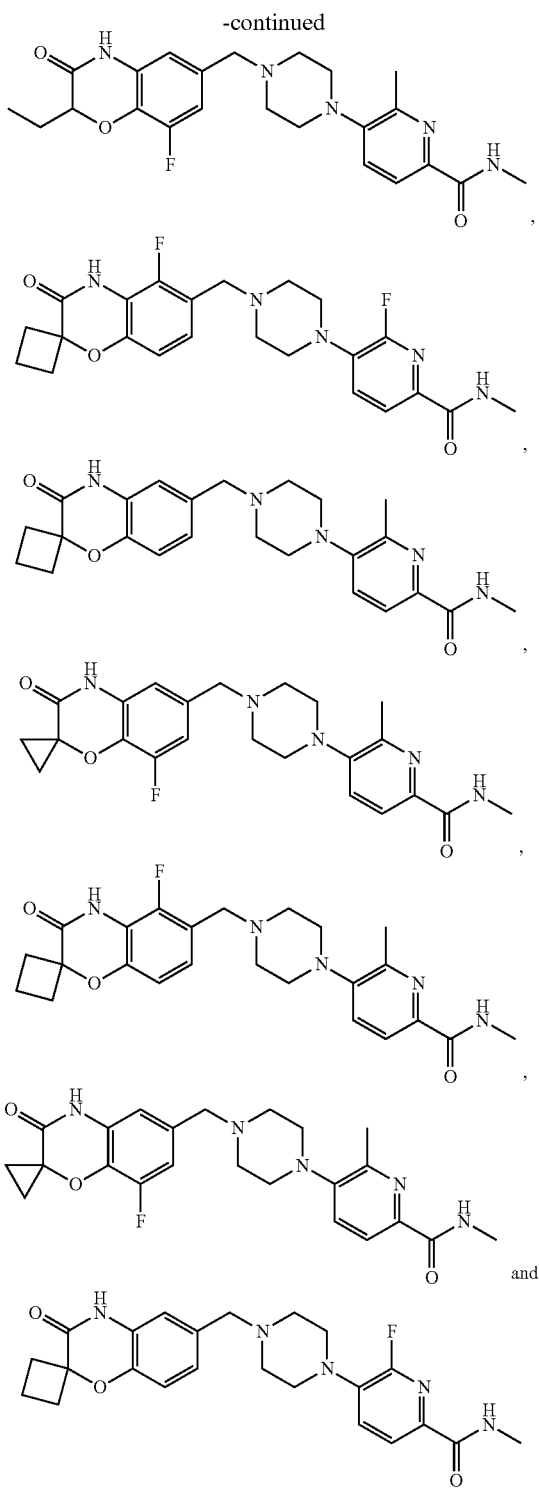

(including stereoisomers and/or pharmaceutically acceptable salts of any of the foregoing).

Example A

PARP Assay

FP Binding Assay (PARP1, PARP2)

The PARP1 and PARP 2 protein and the PARPi-FL were purchased from BPS Bioscience. The assay buffer was 50 mM Tris pH 8.0, 0.001% Triton X-100, 10 mM $MgCl_2$, 150 mM NaCl. The compounds were diluted into top point concentration in 384PP-plate and transferred serially into an Optiplate-384F plate. Compound (20 nL) or DMSO was added to assay plate and then 10 uL of 40 nM PARP1 or PARP2 (diluted using assay buffer) was added. The assay plate was centrifuged at 1000 rpm for 1 min and then incubated for 30 min at rt. 6 nM PARPi-FL (diluted using assay buffer) (10 uL) was added to the plate (final concentration of PARP1 and PARP2 was 20 nM, and PARPi-FL was 3 nM). After centrifuging at 1000 rpm for 1 min, the assay plate was incubated at rt 4 h. The plates were read using Envision with Excitation filter. The data analysis was done by calculating the inhibition rate using mP value using the following equation. Inhibition (%)=(1−mpC−mpL)/ mpH−mpL×100%.

Proliferation Assay (PARP Inhibitors) in DLD-1 wt and DLD-1 BRCA2

DLD-1-wt and DLD-1 mutant cells are cultured in RPMI 1640+10% FBS+1% PS. The cells are harvested into culture media for 2-3 days. The cells are diluted into culture media (density $2\sim3\times10^6$) and 40 uL of cell suspension (50 cells/ well for DLD-1 wt and 50 cells/well for DLD-1 BRCA (−/−). The plates are covered and spun at rt at 1000 rpm, for 1 minute and then transferred. The plates are placed into 37° C. 5% $CO_2$ incubator overnight. Test compounds are dissolved at 10 mM DMSO stock solution and then 40 uL of stock solution is transferred to a 384 PP-plate. A 10-point dilution is carried out by transferring 10 uL compound into 30 μL DMSO by using TECAN (EVO200) liquid handler. The plates are spun at rt at 1000 rpm for 1 minute and then shaken on a plate shaker for 2 minutes. Forty nL of diluted compound is transferred into the cell plate by using a liquid handler. After 7 days of incubation, a CTG detection assay is performed. The CTG detection assay is carried out by removing the plates from the incubators and then equilibrated at rt for 15 minutes. The CellTiter Glo reagents are thawed and equilibrated at rt. CellTiter-Glo reagent (30 μL) is added into each well, and the plates are placed at rt for 30 minutes followed by reading on EnVision. The inhibition activity is calculated using the formula: % Inhibition=100× (LumHC−LumSample)/(LumHC−LumLC).

The results of the cell-based assay are provided in Table 1. In Table 1, 'A' indicates an $IC_{50}$ of <0.1 μM, 'B' indicates an $IC_{50}$ of ≥0.1 μM and <1.0 μM, and 'C' indicates an $IC_{50}$ of ≥1.0 μM. As shown by the results in Table 1, compounds of Formula (I), including pharmaceutically acceptable salts thereof, are effective PARP1 inhibitors.

TABLE 1

| Compound | PARP1 $IC_{50}$ |
|---|---|
| A1 | A |
| 1aa | A |
| 1ab | A |
| 2aa | A |
| 2ab | A |
| 3aa | A |
| 3ab | A |
| A4 | C |
| A5 | A |
| A6 | A |
| A7 | A |
| A8 | A |
| A9 | A |

The results of the biochemical assay are provided in Table 2. In Table 2, 'A' indicates an $IC_{50}$ of <0.005 μM, 'B' indicates an IC$_{50}$ of ≥0.005 µM and <0.01 µM, and 'C' indicates an IC$_{50}$ of ≥0.01 µM. As shown by the results in Table 2, compounds of Formula (I), including pharmaceutically acceptable salts thereof, are effective PARP1 inhibitors.

TABLE 2

| Compound | PARP1 IC$_{50}$ |
| --- | --- |
| 1 enantiomer of A3 | A |
| A6 | A |
| A7 | A |
| A8 | A |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the present disclosure.

What is claimed is:

1. A compound which is 5-(4-((5-fluoro-3-oxo-3,4-dihydrospiro[benzo[b] [1,4]oxazine-2,1'-cyclopropan]-6-yl)methyl)piperazin-1-yl)-N,6-dimethylpicolinamide, or a pharmaceutically acceptable salt thereof, having the structure:

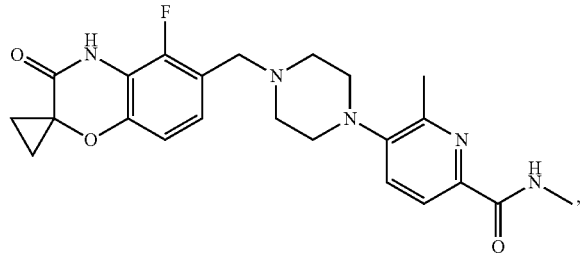 [SMILES: CNC(=O)c1ccc(N2CCN(Cc3ccc4c(c3F)NC(=O)C3(CC3)O4)CC2)c(C)n1]

or a pharmaceutically acceptable salt thereof.

2. The compound of claim 1, which is 5-(4-((5-fluoro-3-oxo-3,4-dihydrospiro[benzo[b][1,4]oxazine-2,1'-cyclopropan]-6-yl)methyl)piperazin-1-yl)-N,6-dimethylpicolinamide.

3. A pharmaceutical composition comprising a compound which is 5-(4-((5-fluoro-3-oxo-3,4-dihydrospiro[benzo[b]1 [1,4]oxazine-2,1'-cyclopropan]-6-yl)methyl)piperazin-1-yl)-N,6-dimethylpicolinamide, or a pharmaceutically acceptable salt thereof, having the structure:

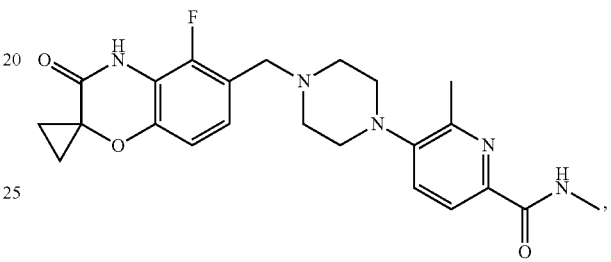

or a pharmaceutically acceptable salt thereof, and a pharmaceutically acceptable carrier, diluent, excipient or combination thereof.

4. The pharmaceutical composition of claim 3, wherein the compound is 5-(4-((5-fluoro-3-oxo-3,4-dihydrospiro [benzo[b][1,4]oxazine-2,1'-cyclopropan]-6-yl)methyl)piperazin-1-yl)-N,6-dimethylpicolinamide.

* * * * *

UNITED STATES PATENT AND TRADEMARK OFFICE
CERTIFICATE OF CORRECTION

PATENT NO. : 12,054,479 B1
APPLICATION NO. : 18/596024
DATED : August 6, 2024
INVENTOR(S) : Sunil Paliwal It is certified that error appears in the above-identified patent and that said Letters Patent is hereby corrected as shown below:

On the Title Page

Page 2, Column 2 (Item (56) Other Publications), Line 2, delete "benzazol" and insert -- benzoxazol --.

In the Specification

Column 6, Line 57, delete "pyrrolidione," and insert -- pyrrolidone, --.

Column 6, Line 59, delete "thiamorpholine," and insert -- thiomorpholine, --.

Column 6, Line 59, delete "thiamorpholine" and insert -- thiomorpholine --.

Column 6, Line 60, delete "thiamorpholine" and insert -- thiomorpholine --.

Column 12, Line 21, delete "$C_{14}$" and insert -- $C_{1-4}$ --.

Column 12, Line 34, delete "$C_{14}$" and insert -- $C_{1-4}$ --.

Column 12, Line 65, delete "$C_{14}$" and insert -- $C_{1-4}$ --.

Column 13, Line 13, delete "$C_{14}$" and insert -- $C_{1-4}$ --.

Column 14, Line 25, delete "0" and insert -- O --.

Column 18, Line 22, delete "$C_{14}$" and insert -- $C_{1-4}$ --.

Column 21, Line 8, delete "Ria" and insert -- R1a --.

Signed and Sealed this
Twenty-sixth Day of November, 2024

Katherine Kelly Vidal
*Director of the United States Patent and Trademark Office*

CERTIFICATE OF CORRECTION (continued)

Column 21, Line 44, delete "$C_{14}$" and insert -- $C_{1-4}$ --.

Column 22, Line 19, delete "$C_{14}$" and insert -- $C_{1-4}$ --.

Column 22, Line 29, delete "Rib" and insert -- $R^{1b}$ --.

Column 23, Line 62, delete "Ria" and insert -- $R^{1a}$ --.

Column 25, Line 25, delete "$C_{14}$" and insert -- $C_{1-4}$ --.

Column 25, Line 28, delete "$C_{14}$" and insert -- $C_{1-4}$ --.

Column 25, Line 38, delete "$C_{14}$" and insert -- $C_{1-4}$ --.

Column 25, Line 60, delete "$C_{14}$" and insert -- $C_{1-4}$ --.

Column 26, Line 25, delete "$C_{14}$" and insert -- $C_{1-4}$ --.

Column 26, Line 28, delete "$C_{14}$" and insert -- $C_{1-4}$ --.

Column 26, Line 38, delete "$C_{14}$" and insert -- $C_{1-4}$ --.

Column 26, Line 60, delete "$C_{14}$" and insert -- $C_{1-4}$ --.

Column 37, Line 28-37, delete " 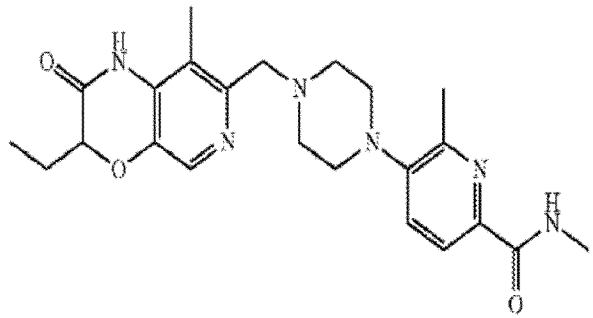 " and insert

-- 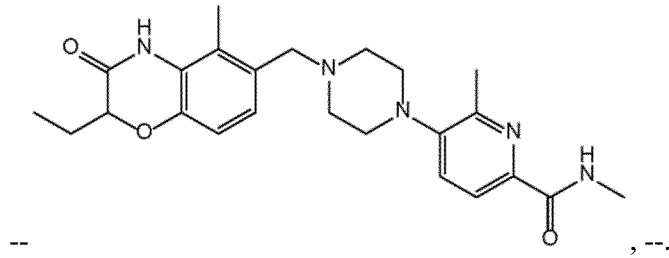 , --.

Column 44, Line 50-59, delete " 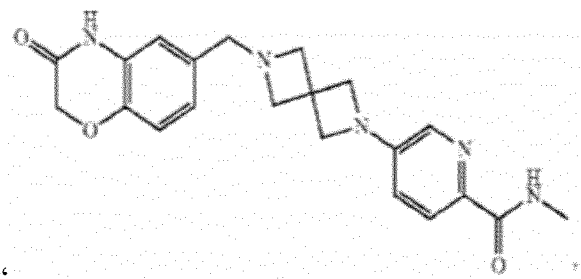 " and insert

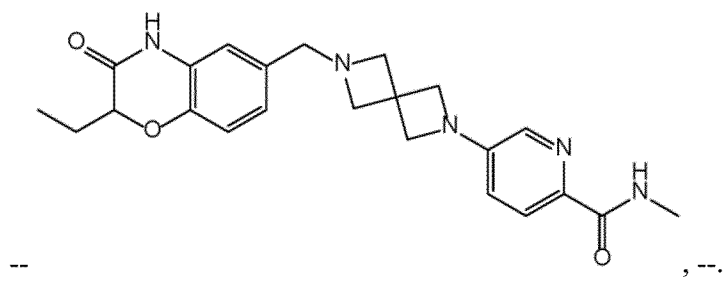 , --.

Column 59, Line 47, delete "tetracarcinoma," and insert -- teratocarcinoma, --.

Column 59, Line 47, delete "nuroblastoma," and insert -- neuroblastoma, --.

Column 60, Line 40 (approx.), line Below "Tetrahydrofuran" insert -- Example 1 Compounds A1, 1aa and 1ab --.

Column 62, Line 19-20, delete "N.N-diisopropylethylamine" and insert
-- N,N-diisopropylethylamine --.

Column 62, Line 68, below "1.766 min." insert -- Example 2 Compounds A2, 2aa and 2ab --.

Column 64, Line 68, line Below "3H)." insert -- Example 3 Compounds A3, 3aa and 3ab --.

Column 65, Line 2 (approx.), delete "BR$_2$" and insert -- Br$_2$ --.

Column 67, Line 28 (approx.), delete "Na2SO$_4$," and insert -- Na$_2$SO$_4$, --.

Column 67, Line 39, delete "was" and insert -- was quenched --.

Column 69, Line 5, delete "min" and insert -- min. --.

Column 69, Line 19 (approx.), below "(s, 1H)." insert -- Example 4 Compound A4 --.

Column 70, Line 29, delete "1H)" and insert -- 1H). --.

Column 71, Line 7 (approx.), line Below "(m, 1H)." insert -- Example 5 Compound A5 --.

Column 71, Line 65, delete "THE" and insert -- THF --.

Column 72, Line 57 (approx.), line Below "(s, 1H)." insert -- Example 6 Compound A6 --.

Column 74, Line 39 (approx.), line Below "(m, 2H)." insert -- Example 7 Compound A7 --.

Column 75, Line 12 (approx.), line Below "(m, 2H)." insert -- Example 8 Compounds A8 and A9 --.

Column 76, Line 2-8 (approx.), delete " 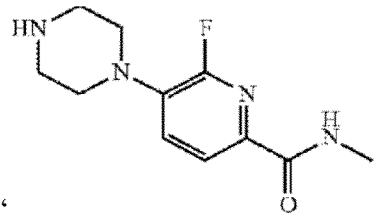 " and insert 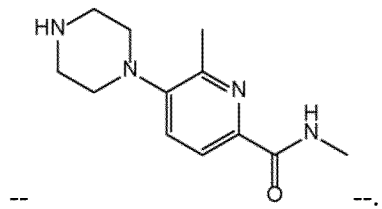 --.

Column 76, Line 13-23 (approx.), delete " 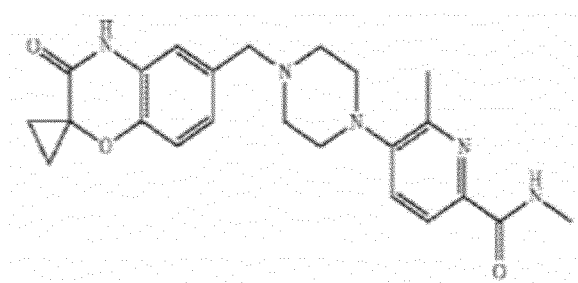 " and insert 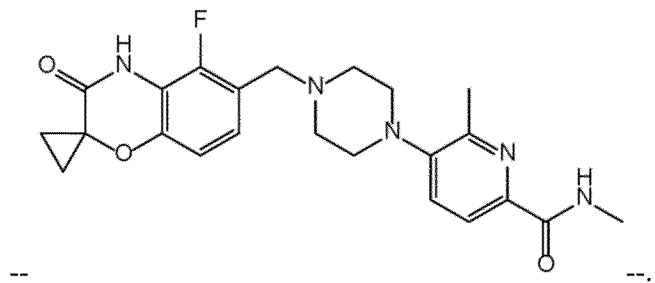 --.

In the Claims

Column 87, Line 26-27, Claim 1, delete "dihydrospiro[benzo[b] [1,4]" and insert -- dihydrospiro[benzo[b][1,4] --.

Column 88, Line 7-8, Claim 3, delete "3,4-dihydrospiro[benzo[b]1[1,4]" and insert -- 3,4-dihydrospiro[benzo[b][1,4] --.